US011851656B2

(12) United States Patent
Turunen et al.

(10) Patent No.: US 11,851,656 B2
(45) Date of Patent: *Dec. 26, 2023

(54) CHEMICALLY MODIFIED SINGLE-STRANDED RNA-EDITING OLIGONUCLEOTIDES

(71) Applicant: ProQR Therapeutics II B.V., Leiden (NL)

(72) Inventors: Janne Juha Turunen, Leiden (NL); Antti Aalto, Leiden (NL); Bart Klein, Leiden (NL); Lenka Van Sint Fiet, Leiden (NL); Julien Auguste Germain Boudet, Leiden (NL)

(73) Assignee: ProQR Therapeutics II B.V., Leiden (NL)

( * ) Notice: Subject to any disclaimer, the term of this patent is extended or adjusted under 35 U.S.C. 154(b) by 281 days.

This patent is subject to a terminal disclaimer.

(21) Appl. No.: 17/152,982

(22) Filed: Jan. 20, 2021

(65) Prior Publication Data

US 2021/0238597 A1 Aug. 5, 2021

Related U.S. Application Data

(63) Continuation of application No. 16/329,787, filed as application No. PCT/EP2017/071912 on Aug. 31, 2017, now Pat. No. 10,941,402.

(30) Foreign Application Priority Data

| Sep. 1, 2016 | (GB) | 1614858 |
| Sep. 27, 2016 | (GB) | 1616374 |
| Dec. 16, 2016 | (GB) | 1621467 |
| Feb. 24, 2017 | (GB) | 1703034 |
| May 10, 2017 | (GB) | 1707508 |

(51) Int. Cl.
*C12N 15/113* (2010.01)

(52) U.S. Cl.
CPC ........ *C12N 15/113* (2013.01); *C12N 2310/11* (2013.01); *C12N 2310/344* (2013.01); *C12N 2310/533* (2013.01); *C12N 2320/34* (2013.01); *C12Y 305/04004* (2013.01)

(58) Field of Classification Search
None
See application file for complete search history.

(56) References Cited

U.S. PATENT DOCUMENTS

| 9,650,627 | B1 | 5/2017 | Rosenthal et al. | |
| 10,676,737 | B2* | 6/2020 | Klein | C12N 15/907 |
| 10,941,402 | B2* | 3/2021 | Turunen | C12N 15/113 |
| 10,988,763 | B2* | 4/2021 | Turunen | A61P 11/08 |
| 11,274,300 | B2* | 3/2022 | Aalto | C12N 15/111 |
| 11,390,865 | B2 | 7/2022 | Fukuda et al. | |
| 2014/0228556 | A1 | 8/2014 | Fukuda et al. | |
| 2014/0357856 | A1 | 12/2014 | Monia et al. | |
| 2017/0355985 | A1 | 12/2017 | Dellinger et al. | |
| 2018/0208924 | A1 | 7/2018 | Fukuda et al. | |
| 2019/0093098 | A1 | 3/2019 | Stafforst et al. | |
| 2019/0330622 | A1 | 10/2019 | Turunen et al. | |
| 2019/0352641 | A1 | 11/2019 | Aalto et al. | |
| 2020/0199586 | A1 | 6/2020 | Klein et al. | |

FOREIGN PATENT DOCUMENTS

| EP | 3323890 A1 | 5/2018 |
| EP | 3353299 B1 | 3/2020 |
| WO | WO-0066604 A2 | 11/2000 |
| WO | WO-2004091515 A2 | 10/2004 |
| WO | WO-2005087949 A1 | 9/2005 |
| WO | WO-2005094370 A2 | 10/2005 |
| WO | WO-2010064146 A2 | 6/2010 |
| WO | WO-2010115206 A2 | 10/2010 |
| WO | WO-2011005761 A1 | 1/2011 |
| WO | WO-2011072082 A2 | 6/2011 |
| WO | WO-2011085271 A2 | 7/2011 |
| WO | WO-2011119887 A1 | 9/2011 |
| WO | WO-2012006241 A2 | 1/2012 |
| WO | WO-2014/011053 A1 | 1/2014 |
| WO | WO-2014010250 A1 | 1/2014 |
| WO | WO-2014012081 A2 | 1/2014 |
| WO | WO-2015107425 A2 | 7/2015 |
| WO | WO-2016062886 A1 | 4/2016 |
| WO | WO-2016079181 A1 | 5/2016 |
| WO | WO-2016/097212 A1 | 6/2016 |
| WO | WO-2016089433 A1 | 6/2016 |
| WO | WO-2016094845 A2 | 6/2016 |

(Continued)

OTHER PUBLICATIONS

Nelwan et al. Journal of Advances in Biology & Biotechnology 16, pp. 1-12 (Year: 2017).*
International Search Report for PCT/EP2017/071912, dated Dec. 15, 2017 (5 pages).
Kumar et al. Microbiology and Molecular Biology Reviews, vol. 62, p. 1415-1434 (Year: 1998).
Lamond et al. (1993) "Antisense oligonucleotides made of 2′-O-alkylRNA: their properties and applications in RNA biochemistry," FEBS Letters, 325(1, 2): 123-127.
Lancaster et al. (2014) "Organogenesis in a Dish: Modeling Development and Disease Using Organoid Technologies," Science, 345(6194): 1247125.

(Continued)

*Primary Examiner* — Brian Whiteman
(74) *Attorney, Agent, or Firm* — Sterne, Kessler, Goldstein & Fox P.L.L.C.

(57) ABSTRACT

The invention relates to antisense oligonucleotides that are capable of bringing about specific editing of a target nucleotide (adenosine) in a target RNA sequence in a eukaryotic cell, wherein said oligonucleotide does not, in itself, form an intramolecular hairpin or stem-loop structure, and wherein said oligonucleotide comprises a non-complementary nucleotide in a position opposite to the nucleotide to be edited in the target RNA sequence.

40 Claims, 18 Drawing Sheets

Specification includes a Sequence Listing.

(56) References Cited

FOREIGN PATENT DOCUMENTS

| | | |
|---|---|---|
| WO | WO-2016096938 A1 | 6/2016 |
| WO | WO-2017010556 A1 | 1/2017 |
| WO | WO-2017015555 A1 | 1/2017 |
| WO | WO-2017015575 A1 | 1/2017 |
| WO | WO-2017050306 A1 | 3/2017 |
| WO | WO-2017062862 A2 | 4/2017 |
| WO | WO-2017192664 A1 | 11/2017 |
| WO | WO-2017198775 A1 | 11/2017 |
| WO | WO-2017/220751 A1 | 12/2017 |
| WO | WO-2017210647 A1 | 12/2017 |
| WO | WO-2018067973 A1 | 4/2018 |
| WO | WO-2018126176 A1 | 7/2018 |
| WO | WO-2018223056 A1 | 12/2018 |
| WO | WO-2018223073 A1 | 12/2018 |
| WO | WO-2018223081 A1 | 12/2018 |
| WO | WO-2018237194 A1 | 12/2018 |
| WO | WO-2019032607 A1 | 2/2019 |
| WO | WO-2019/158475 A1 | 8/2019 |
| WO | WO-2019/219581 A1 | 11/2019 |

OTHER PUBLICATIONS

Martine Nelwan Journal of Advances in Biology & Biotechnology 16: 1-12 (Year: 2017).

Matthews et al. (2016) "Structures of Human ADAR2 Bound to dsRNA Reveal Base-Flipping Mechanism and Basis for Site Selectivity," Nat. Struct. Mol. Biol., 23(5): 426-433.

Mei et al. Trends in Pharmaceological Sciences vol. 41, pp. 475-486 (Year: 2020).

Mizrahi et al. ACS Chem. Biol. 8, 832-839 (Year: 2013).

Mizrahi etal. ACS Chem. Bio. supporting information, pp. 1-4 (Year: 2013).

Montiel-Gonzalez et al. (2013) "Correction of Mutations Within the Cystic Fibrosis Transmembrane Conductance Regulator by Site-Directed RNA Editing," PNAS, 110(45): 18285-18290.

Montiel-Gonzalez et al. (2016) "An Efficient System for Selectively Altering Genetic Information Within mRNAs," Nucleic Acid Research, 44(21): e157 (12 pages).

Rutten et al. Brain 139: 1123-1135 (Year: 2016).

Sala et al. (2009) "Tissue-Engineered Small Intestine and Stomach Form from Autologous Tissue in a Preclinical Large Animal Model," J Surg Res.; 156(2): 205-12.

Sato et al. (2011) "Long-term Expansion of Epithelial Organoids From Human Colon, Adenoma, Adenocarcinoma, and Barrett's Epithelium," Gastroenterology, 141(5): 1762-72.

Schneider et al. (2014) "Optimal GuideRNAs for Re-directing Deaminase Activity of hADAR1 and hADAR2 in Trans," Nucleic Acids Res., 42(10):e87.

Sharma et al. (2015) "Oligonucleotide Therapeutics: Chemistry, Delivery and Clinical Progress," Future Med. Chem., 7:16 (2221-2242.

Stefl et al. (2006) "Structure and Specific RNA Binding of ADAR2 Double-Stranded RNA Binding Motifs," Structure 14(2): 345-355.

Tian et al. (2011) "A Structural Determinant Required for RNA Editing," Nucleic Acids Res. 39(13): 5669-5681.

Vogel et al. (2014) "Improving Site-Directed RNA Editing in Vitro and in Cell Culture by Chemical Modification of the GuideRNA," Angewandte Chemie Int. Ed., 53:6267-6271.

Woolf et al. (1995) "Toward the Therapeutic Editing of Mutated RNA Sequences," PNAS, 92: 8298-8302.

Written Opinion for PCT/EP2017/071912, dated Dec. 15, 2017 (5 pages).

Agrawal, S., et al., "Mixed-backbone Oligonucleotides as Second Generation Antisense Oligonucleotides: in Vitro and in Vivo Studies," Proceedings of the National Academy of Sciences of the United States of America 94:2620-2625, National Academy of Sciences, United States (Mar. 1997).

Agrawal, S., et al., "Mixed-Backbone Oligonucleotides Containing Phosphorothioate and Methylphosphonate Linkages as Second Generation Antisense Oligonucleotide," Nucleosides & Nucleotides 16(7-9):927-936, Taylor & Francis, United Kingdom (Jul. 1997).

Allain, F. H., et al., "Structural Basis of the RNA-binding Specificity of Human U1A Protein," The EMBO Journal 16(18):5764-5772, European Molecular Biology Organization, Germany (Sep. 1997).

Aruscavage, P. J. and Bass, B. L., "A Phylogenetic Analysis Reveals an Unusual Sequence Conservation Within Introns Involved in RNA Editing," RNA 6(2):257-269, Cold Spring Harbor Laboratory Press, United States (Feb. 2000).

Brown, D. A., et al., "Effect of Phosphorothioate Modification of Oligodeoxynucleotides on Specific Protein Binding," The Journal of Biological Chemistry 269(43):26801-26805, Elsevier Inc., United States (Oct. 1994).

Burkard, M. E., and Turner, D. H., "NMR Structures of r(GCAGGCGUGC)$_2$ and Determinants of Stability for Single Guanosine-Guanosine Base Pairs," Biochemistry 39:11748-11762, with Supporting Information (S1-S28), American Chemical Society, United States (Sep. 2000).

Dawson, T. R., et al., "Structure and Sequence Determinants Required for the RNA Editing of ADAR2 Substrates," The Journal of Biological Chemistry 279(6):4941-4951, Elsevier Inc., United States (2004).

Deleavey, G. F., and Damha, M. J., "Designing Chemically Modified Oligonucleotides for Targeted Gene Silencing," Chemistry & Biology 19(8):937-954, Cell Press, United States (Aug. 2012).

Desterro, J. M., et al., "Dynamic Association of RNA-editing Enzymes with the Nucleolus," Journal of Cell Science 116(9):1805-1818, The Company of Biologists, United Kingdom (May 2003).

Eggington, J. M., et al., "Predicting Sites of ADAR Editing in Double-stranded RNA," Nature Communications 2(1):319, pp. 1-9, Nature Publishing Group, United Kingdom (May 2011).

Flur, S. and Micura, R., "Chemical Synthesis of RNA With Site-specific Methylphosphonate Modifications," Methods 107:79-88, Academic Press, United States (Sep. 2016).

Garncarz, W., et al., "A High-throughput Screen to Identify Enhancers of ADAR-mediated RNA-editing," RNA Biology 10(2):192-204, Landes Bioscience, United States (Feb. 2013).

Glen Research, "Phosphonoacetate (PACE) Oligonucleotides," Glen Report 20.21 20(2):1-16, GlenResearch.com, accessed at URL:[https://www.glenresearch.com/media/contentmanager/content/glenreport/GR20-2.pdf], Glen Research and Maravai LifeSciences, United States (Oct. 2008).

Grunewald, A., et al., "Does Uncoupling Protein 2 Expression Qualify as Marker of Disease Status in LRRK2-associated Parkinson's Disease?" Antioxidants & Redox Signaling 20(13):1955-1960, Mary Ann Liebert, Inc., United States (2014).

Hallegger, M., et al., "RNA Aptamers Binding the Double-stranded RNA-binding Domain," RNA 12(11):1993-2004, Cold Spring Harbor Laboratory Press, United States (2006).

Hamma, T., and Miller, P.S., "Syntheses of Alternating Oligo-2'-O-methylribonucleoside Methylphosphonates and their Interactions with HIV TAR RNA," Biochemistry 38(46):15333-15342, American Chemical Society, United States (Nov. 1999).

Haudenschild, B. L., et al., "A Transition State Analogue for an RNA-editing Reaction," Journal of the American Chemical Society 126(36):11213-11219, American Chemical Society, United States (Sep. 2004).

Higuchi, M., et al., "RNA Editing of AMPA Receptor Subunit GluR-B: a Base-paired Intron-exon Structure Determines Position and Efficiency," Cell 75:1361-1370, Cell Press, United States (Dec. 1993).

Ikehara, M., et al., "Nucleosides and Nucleotides. XLVII. Conformation of Purine Nucleosides and their 5'-phosphates" Biochemistry 11(5):830-836, American Chemical Society, United States (Feb. 1972).

Jiang, F., et al., "Structural Basis of RNA Folding and Recognition in an AMP-RNA Aptamer Complex," Nature 382:183-186, Nature Publishing Group, Germany (Jul. 1996).

Juliano, R. L., et al., "Cellular Uptake and Intracellular Trafficking of Antisense and siRNA Oligonucleotides," Bioconjugate Chemistry 23(2):147-157, American Chemical Society, United States (Feb. 2012).

(56) References Cited

OTHER PUBLICATIONS

Juliano, R. L., "The Delivery of Therapeutic Oligonucleotides," Nucleic Acids Research 44(14):6518-6548, Oxford University Press, United Kingdom (2016).
Kean, J. M., et al., "Inhibition of Herpes Simplex Virus Replication by Antisense Oligo-2'-0-methylribonucleoside Methylphosphonates," Biochemistry 34(45): 14617-14620, American Chemical Society, United States (Nov. 1995).
Kuttan, A., and Bass, B. L., "Mechanistic Insights Into Editing-site Specificity of ADARs," Proceedings of the National Academy of Sciences of the United States of America 109(48):E3295-E3304, National Academy of Sciences, United States (Nov. 2012).
Lennox, K. A., and Behlke, M. A., "Chemical Modification and Design of Anti-miRNA Oligonucleotides," Gene Therapy 18(12):1111-1120, Nature Publishing Group, United Kingdom (Dec. 2011).
Lomeli, H., et al., "Control of kinetic properties of AMPA receptor channels by nuclear RNA editing," Science 266(5191):1709-1713, American Association for the Advancement of Science, United States (Dec. 1994).
Lu, J., et al., "Synthesis of Pyridine, Pyrimidine and Pyridinone C-nucleoside Phosphoramidites for Probing Cytosine Function in RNA," The Journal of Organic Chemistry 74:8021-8030, American Chemical Society, United States (Nov. 2009).
Macbeth, M. R., and Bass, B. L., "Large-scale Overexpression and Purification of ADARs from *Saccharomyces cerevisiae* for Biophysical and Biochemical Studies," Methods in Enzymology 424:319-331, Elsevier, Netherlands (Jan. 2007).
Macbeth, M. R., et al., "Evidence for Auto-inhibition by the N Terminus of hADAR2 and Activation by dsRNA Binding," RNA 10:1563-1571, Cold Spring Harbor Laboratory Press, United States (Oct. 2004).
Masliah, G., et al., "RNA Recognition by Double-stranded RNA Binding Domains: a Matter of Shape and Sequence," Cellular and Molecular Life Sciences 70(11):1875-1895, Springer, Switzerland (2013).
Matsui, M., et al., "Effect of 2'-O-methyl/thiophosphonoacetate-modified Antisense Oligonucleotides on Huntingtin Expression in Patient-derived Cells," Artificial DNA: PNA & XNA 5(3):e1146391, Taylor & Francis, United Kingdom (Dec. 2014).
Maydanovych, O., et al., "Probing Adenosine-to-inosine Editing Reactions Using RNA-containing Nucleoside Analogs," Methods in Enzymology 424:369-386, Elsevier, Netherlands (Jan. 2007).
Murayama, K., et al., "Highly Stable Duplex Formation by Artificial Nucleic Acids Acyclic Threoninol Nucleic Acid (aTNA) and Serinol Nucleic Acid (SNA) with Acyclic Scaffolds," Chemistry—A European Journal 19:14151-14158, Wiley-VCH Verlag, Germany (Oct. 2013).
Nishikura, K., "Functions and Regulation of RNA Editing by ADAR Deaminases," Annual Review of Biochemistry 79:321-349, Annual Reviews, United States (Oct. 2010).
Pan, B., et al., "Crystal Structure of an RNA 16-mer Duplex R(GCAGAGUUAAAUCUGC)2 With Nonadjacent G(Syn) A+(Anti) Mispairs," Biochemistry 38(9):2826-2831, American Chemical Society, United States (Mar. 1999).
Papkovskaia, T. D., et al., "G2019S Leucine-rich Repeat Kinase 2 Causes Uncoupling Protein-mediated Mitochondrial Depolarization," Human Molecular Genetics 21(19):4201-4213, IRL Press at Oxford University Press, United Kingdom (2012).
Pasternak, A., and Wengel, J., "Unlocked Nucleic Acid—an RNA Modification With Broad Potential," Organic & Biomolecular Chemistry 9:3591-3597, Royal Society of Chemistry, United Kingdom (Mar. 2011).
Penn, A. C., et al., "Steric Antisense Inhibition of AMPA Receptor Q/R Editing Reveals Tight Coupling to Intronic Editing Sites and Splicing," Nucleic Acids Research 41(2):1113-1123, Oxford Academic Press, United Kingdom (Jan. 2013).

ProQR Therapeutics, "Axiomer® technology: Therapeutic oligonucleotides for directing site-specific A-to-I editing by endogenous ADAR enzymes," Presentation, accessed at www.proqr.com, 21 pages (Sep. 2021).
Rieder, L. E., et al., "Tertiary Structural Elements Determine the Extent and Specificity of Messenger RNA Editing," Nature Communications 4:2232, Nature Publishing Group, United Kingdom (Aug. 2013).
Saccomanno, L. and Bass, B. L., "A Minor Fraction of Basic Fibroblast Growth Factor mRNA is Deaminated in *Xenopus* Stage VI and Matured Oocytes," RNA 5(1):39-48, Cold Spring Harbor Laboratory Press, United States (1999).
Schade, M., et al., "A 6 bp Z-DNA Hairpin Binds Two Z Alpha Domains From the Human RNA Editing Enzyme ADAR1," FEBS Letters 458(1):27-31, John Wiley & Sons Ltd., United Kingdom (Sep. 1999).
Schweitzer, M., and Engels, J. W., "Sequence Specific Hybridization Properties of Methylphosphonate Oligodeoxynucleotides," Journal of Biomolecular Structure and Dynamics 16(6):1177-1188, Taylor & Francis, United Kingdom (Jun. 1999).
Sheehan, D., et al., "Biochemical Properties of Phosphonoacetate and Thiophosphonoacetate Oligodeoxyribonucleotides," Nucleic Acids Research 31(14):4109-4118, Oxford Academic Press, United Kingdom (Jul. 2003).
Singleton, M., et al., "X-ray Structure of Pyrrolidone Carboxyl Peptidase From the Hyperthermophilic Archacon *Thermococcus litoralis*," Structure 7(3):237-244, Cell Press, United States (Mar. 1999).
Sipova, H., et al., "5'-O-Methylphosphonate Nucleic Acids—new Modified DNAs that Increase the *Escherichia coli* RNase H Cleavage Rate of Hybrid Duplexes," Nucleic Acids Research 42(8):5378-5389, Oxford Academic Press, United Kingdom (Apr. 2014).
Smith, G. A., et al., "Fibroblast Biomarkers of Sporadic Parkinson's Disease and LRRK2 Kinase Inhibition," Molecular Neurobiology 53(8):5161-5177, Humana Press, United States (2016).
Stafforst, T. and Schneider, M. F., "An RNA-deaminase Conjugate Selectively Repairs Point Mutations," Angewandte Chemie 51(44):11166-11169, Wiley-VCH, Germany (2012).
Stefl, R., and Allain, F. H., "A Novel RNA Pentaloop Fold Involved in Targeting ADAR2," RNA 11(5):592-597, Cold Spring Harbor Laboratory, United States (May 2005).
Svoboda, P., and Di Cara, A., "Hairpin RNA: a Secondary Structure of Primary Importance," Cellular and Molecular Life Sciences 63(7):901-908, Birkhauser Verlag, Switzerland (Apr. 2006).
Tian, B., et al., "The Double-stranded-RNA-binding Motif: Interference and Much More," Nature Reviews. Molecular Cell Biology 5(12):1013-1023, Nature Pub. Group, United Kingdom (2004).
Vaish, N., et al., "Improved Specificity of Gene Silencing by siRNAs Containing Unlocked Nucleobase Analogs," Nucleic Acids Research 39(5):1823-1832, Oxford Academic Press, United Kingdom (Mar. 2011).
Veliz, E. A., et al., "Substrate Analogues for an RNA-editing Adenosine Deaminase: Mechanistic Investigation and Inhibitor Design," Journal of the American Chemical Society 125(36):10867-10876, American Chemical Society, United States (Sep. 2003).
Vogel, P., and Stafforst, T., "Site-directed RNA Editing With Antagomir Deaminases—a Tool to Study Protein and RNA Function," ChemMedChem 9(9):2021-2025, Wiley-VCH, Germany (2014).
Wong, S. K., et al., "Substrate Recognition by ADAR1 and ADAR2," RNA 7:846-858, Cold Spring Harbor Laboratory, United States (Jun. 2001).
Zangemeister-Wittke, U., et al., "A Novel Bispecific Antisense Oligonucleotide Inhibiting both bcl-2 and bcl-xL Expression Efficiently Induces Apoptosis in Tumor Cells," Clinical Cancer Research 6(6):2547-2555, The Association of Clinical Cancer Research, United States (Jun. 2000).
Zhou, P., et al., "Geometric Characteristics of Hydrogen Bonds Involving Sulfur Atoms in Proteins," Proteins 76(1):151-163, Wiley-Liss, United States (Jul. 2009).
Savva, Y.A., et al., "The ADAR protein family," Genome Biology 13:252, BioMed Central Ltd., United States (Dec. 2012).

\* cited by examiner

Fig. 1A

AON ADAR60-1 targeting *SERPINA1*

```
3'-gacacgacugguagcuGCUcuuucccugacu-5'  (AON)
5'-AUAAGGCUGUGCUGACCAUCGACAAGAAAGGGACUGAAGCUGCUGGGGCCAUGUUUUAGAG-3'
```

Fig. 1B

AON similar to ADAR60-1 with modified bases targeting *SERPINA1*

```
3'-gacacgacugguagcuZXYcuuucccugacu-5'  (AON)
5'-AUAAGGCUGUGCUGACCAUCGACAAGAAAGGGACUGAAGCUGCUGGGGCCAUGUUUUAGAG-3'
```

*Fig. 2A*

| AON name | Sequence 5' -> 3' | Base modifications |
|---|---|---|
| ADAR60-1 | u*c*a*g*ucccuuucUCGucgauggucagc*a*c*a*g (SEQ ID NO:22) | |
| ADAR60-2 | u*c*a*g*ucccuuucCGucgauggucagc*a*c*a*g | |
| ADAR60-3 | u*c*a*g*ucccuuucCGUcgauggucagc*a*c*a*g | |
| ADAR60-4 | u*c*a*g*ucccuuucucgauggucagc*a*c*a*g | |
| ADAR60-5 | u*c*a*g*ucccuuucU*CGucgauggucagc*a*c*a*g | |
| ADAR60-6 | u*c*a*g*ucccuuuc[TCG]ucgauggucagc*a*c*a*g | |
| ADAR60-7 | u*c*a*g*ucccuuuc(ucg)ucgauggucagc*a*c*a*g | |
| ADAR60-8 | u*c*a*g*ucccuuuc[U]C(G)ucgauggucagc*a*c*a*g | |
| ADAR60-9 | u*c*a*g*ucccuuuc[U]X(G)ucgauggucagc*a*c*a*g | X: 5-Methylcytidine |
| ADAR60-10 | u*c*a*g*ucccuuucUCZucgauggucagc*a*c*a*g | Z: Inosine |
| ADAR60-11 | u*c*a*g*ucccuuucUXZucgauggucagc*a*c*a*g | X: 5-Methylcytidine, Z: Inosine |
| ADAR60-12 | u*c*a*g*ucccuuucYXZucgauggucagc*a*c*a*g | Y: Pseudouridine, X: 5-Methylcytidine, Z: Inosine |
| ADAR60-13 | u*c*a*g*ucccuuucYXZucgauggucagc*a*c*a*g | Y: 4-Thiouridine, X: 5-Methylcytidine, Z: Inosine |
| ADAR60-14 | u*c*a*g*ucccuuucYXZucgauggucagc*a*c*a*g | Y: 5-Methyluridine, X: 5-Methylcytidine, Z: Inosine |
| ADAR60-15 | u*c*a*g*ucccuuucYXZucgauggucagc*a*c*a*g | Y: Thienouridine, X: 5-Methylcytidine, Z: Inosine |
| ADAR60-16 | u*c*a*g*ucccuuucYXZucgauggucagc*a*c*a*g | Y: 2,6-diaminopurine, X: 5-Methylcytidine, Z: Inosine |
| ADAR60-17 | u*c*a*g*ucccuuucUXZucgauggucagc*a*c*a*g | X: Pyrrolocytidine, Z: Inosine |
| ADAR60-18 | u*c*a*g*ucccuuucYXZucgauggucagc*a*c*a*g | Y: Pseudouridine, X: Pyrrolocytidine, Z: Inosine |
| ADAR60-19 | u*c*a*g*ucccuuucYXZucgauggucagc*a*c*a*g | Y: Thienouridine, X: Pyrrolocytidine, Z: Inosine |

Fig. 2B

| AON name | Sequence 5' -> 3' | Base modifications |
|---|---|---|
| ADAR60-20 | u*c*a*g*ucccuuucYXZucgauggucagc*a*c*a*g | Y: Pseudouridine, X: 5-Methylcytidine, Z: Thienoguanosine |
| ADAR60-21 | u*c*a*g*ucccuuucYXZucgauggucagc*a*c*a*g | Y: Pseudouridine, X: Pyrrolocytidine, Z: Thienoguanosine |
| ADAR60-22 | u*c*a*g*ucccuuucU"C"G"ucgauggucagc*a*c*a*g | |
| ADAR60-23 | u*c*a*g*ucccuuucU"C"G"ucgauggucagc*a*c*a*g | |
| ADAR60-24 | u*c*a*g*ucccuuucU^C^G^ucgauggucagc*a*c*a*g | |
| ADAR60-25 | u*c*a*g*ucccuuucU#C#G#ucgauggucagc*a*c*a*g | |
| ADAR60-26 | u*c*a*g*ucccuuucYXZucgauggucagc*a*c*a*g | Y: 5-Methoxyuridine, X: 5-Methylcytidine, Z: Inosine |
| ADAR60-27 | u*c*a*g*ucccuuucYXZucgauggucagc*a*c*a*g | Y: dihydrouridine, X: 5-Methylcytidine, Z: Inosine |
| ADAR60-28 | u*c*a*g*ucccuuucYXZucgauggucagc*a*c*a*g | Y: Pseudouridine, X: 5-Hydroxymethylcytidine, Z: Inosine |
| ADAR60-29 | u*c*a*g*ucccuuucYXZucgauggucagc*a*c*a*g | Y: Pseudouridine, X: 5-Methylcytidine, Z: 7-Methylguanosine |
| ADAR60-30 | u*c*a*g*ucccuuucYXZucgauggucagc*a*c*a*g | Y: Pseudouridine, X: 5-Methylcytidine, Z: 7-deazaguanosine |
| ADAR60-31 | u*c*a*g*ucccuuucYXZucgauggucagc*a*c*a*g | Y: Pseudouridine, X: 5-Methylcytidine, Z: 8-aza-7-deazagunaosine |
| ADAR60-32 | u*c*a*g*ucccuuucYXZucgauggucagc*a*c*a*g | Y: Pseudouridine, X: 5-Methylcytidine, Z: 7-aminomethyl-7-deazaguanosine |
| ADAR68 | c*c*u*g*cgacacuucggcCCAgagcugcucc*u*c*a*u (SEQ ID NO:23) | |
| ADAR68-1 | c*c*u*g*cgacacuucggcXXYgagcugcucc*u*c*a*u | X: 5-Methylcytidine, Y: 7-Methyladenosine |
| ADAR68-2 | c*c*u*g*cgacacuucggcXXYgagcugcucc*u*c*a*u | X: 5-Methylcytidine, Y: 8-Methyladenosine |
| ADAR68-3 | c*c*u*g*cgacacuucggcXXYgagcugcucc*u*c*a*u | X: 5-Methylcytidine, Y: 3-deazaadenosine |
| ADAR68-4 | c*c*u*g*cgacacuucggcXXYgagcugcucc*u*c*a*u | X: 5-Methylcytidine, Y: 7-deazaadenosine |
| ADAR68-5 | c*c*u*g*cgacacuucggcXXYgagcugcucc*u*c*a*u | X: 5-Methylcytidine, Y: 8-azidoadenosine |
| ADAR68-6 | c*c*u*g*cgacacuucggcXXYgagcugcucc*u*c*a*u | X: 5-Methylcytidine, Y: Inosine |

Fig. 2C

| AON name | Sequence 5' -> 3' | Base modifications |
|---|---|---|
| ADAR59-2 | c*a*u*u*gaagaagauaagagaaguacugagaaguguugg CCAuggaacag*g*u*a*g (SEQ ID NO:24) | |
| ADAR59-10 | c*a*u*u*gaagaagauaagagaaguacugagaaguguugg CCZuggaacag*g*u*a*g | Z: 2-aminopurine |
| ADAR59-22 | c*a*u*u*gaagaagauaagagaaguacugagaaguguugg[C[A]uggaacag*g*u*a*g | |
| SON2 | g*a*c*u*gaaguacuccuuagagaaaggug[CCA]cuucuuggcaa*a*g*g*a (SEQ ID NO:25) | |
| ADAR94-1 | a*a*g*a*A*G*U*G*G*C*A*c*u*u (SEQ ID NO:26) | |
| ADAR87-1 | g*u*a*g*gcauggggaggaaaagguCCAcuucuuggcaa*a*g*g*a (SEQ ID NO:27) | |
| ADAR65-1 | c*u*g*u*ccaacacagccccagccuuugagaccucuguCCAgaguuguu*c*u*c*c (SEQ ID NO:28) | |
| ADAR65-13 | c*u*g*u*ccaacacagccccagccuuugagaccucuguCC[A]gaguuguu*c*u*c*c idT | |
| ADAR65-14 | c*u*g*u*ccaacacagccccagccuuugagaccucuguC[A]gaguuguu*c*u*c*c idT | |
| ADAR65-15 | c*u*g*u*ccaacacagccccagccuuugagaccucuguXC[A]gaguuguu*c*u*c*c idT | X: 5-Methylcytidine |
| ADAR65-16 | c*u*g*u*ccaacacagccccagccuuugagaccucuguC[X]gaguuguu*c*u*c*c idT | X: deoxy 2-aminopurine |
| ADAR65-18 | c*u*g*u*ccaacacagccccagccuuugagaccucuguC[A]gaauuguu*c*u*c*c idT (SEQ ID NO:29) | |
| ADAR65-19 | c*u*g*u*ccaacacagccccagccuuugagaccucugu[AGA]gaguuguu*c*u*c*c idT | |
| ADAR65-20 | c*u*g*u*ccaacacagccccagccuuugagaccucuguc*C*[A]*G*A*guuguu*c*u*c*c idT | |
| ADAR65-21 | c*u*g*u*ccaacacagccccagccuuugagaccucuguc*C*[A]*gaguuguu*c*u*c*c idT | |
| ADAR65-22 | c*u*g*u*ccaacacagccccagccuuugagaccucugu*u*C*C*A*g*aguuguu*c*u*c*c idT | |
| ADAR65-23 | c*u*g*u*ccaacacagccccagccuuugagaccucuguc(caga)guuguu*c*u*c*c | |
| ADAR65-24 | c*u*g*u*ccaacacagccccagccuuugagaccucugu[CCA]gaguuguu*c*u*c*c | |
| ADAR65-25 | c*u*g*c*u*c*a*a*g*gcccagcccagccuuugagaccucugu[CCA]gaguuguu*c*u*c*c | |
| ADAR65-26 | c*u*g*u*ccaacacagccc*c*a*g*c*c*u*u*g*a*gaccucugu[CCA]gaguuguu*c*u*c*c | |
| ADAR65-27 | c*u*g*u*c*c*a*a*c*a*g*c*c*c*c*a*g*c*c*u*u*u*g*a*gaccucugu[CCA]gaguuguu*c*u*c*c | |
| ADAR65-28 | c*u*g*u*ccaacacagccccagccuuugagaccucugu[C][c][A]gaguuguu*c*u*c*c | |
| ADAR65-29 | c*u*g*u*ccaacacagccccagccuuugagaccucugu[C][c][A]gaguuguu*c*u*c*c | |
| ADAR65-30 | c*u*g*u*ccaacacagccccagccuuugagaccucugu[C*C*A*]gaguuguu*c*u*c*c | |
| ADAR65-31 | c*u*g*u*ccaacacagccccagccuuugagaccucugu[CCA]gaguuguu*c*u*c*c idT | |

Fig. 2D

| AON name | Sequence 5' -> 3' | Base modifications |
|---|---|---|
| ADAR93-2 | a*c*a*c*a*G*cuc*c*a*g*c*c*u*u*u*G*A*gaccu*c*u*g*cCCAGaguu*g*u*c*u*c*c (SEQ ID NO:30) | |
| ADAR93-6 | c*a*c*a*gcccagccuuugagaccucugu[CCA]gaguuguu*c*u*c*c (SEQ ID NO:31) | |
| ADAR93-8 | c*a*c*a*g*c*c*c*c*a*g*c*c*u*u*u*g*agaccucugu[CCA]gaguuguu*c*u*c*c (SEQ ID NO:32) | |
| ADAR93-9 | c*a*c*3*gccc*c*a*g*c*c*u*u*u*g*a*gaccucugcc*[C*A]*gaauuguu*c*u*c*c (SEQ ID NO:33) | |
| ADAR89-10 | g*a*c*u*gagguacuccauagggaaggcacC[A]cuucuuggcaa*a*g*g*a (SEQ ID NO:34) | |
| ADAR89-15 | g*a*c*u*gagguacuccauagggaaggcacC[ACU]ucuuggcaa*a*g*g*a | |
| ADAR89-20 | g*a*c*u*gagguacuccauagggaaggcacC[A]<cu>ucuuggcaa*a*g*g*a | |

Fig. 4A

**AON ADAR68 targeting *IDUA***

```
           3'-uacuccucgucgagACCcggcuucacagcgucc-5' (AON)
5'-GCCCCGCAGAUGAGGAGCAGCUCUAGGCCGAAGUGUCGCAGGCCGGGACCGUCC3'
```

Fig. 4B

**AON similar to ADAR68 with modified bases targeting *IDUA***

```
           3'-uacuccucgucgagYXXcggcuucacagcgucc-5' (AON)
5'-GCCCCGCAGAUGAGGAGCAGCUCUAGGCCGAAGUGUCGCAGGCCGGGACCGUCC3'
```

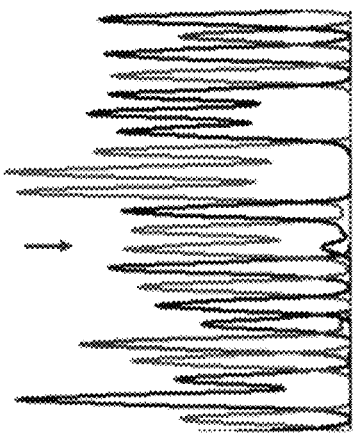
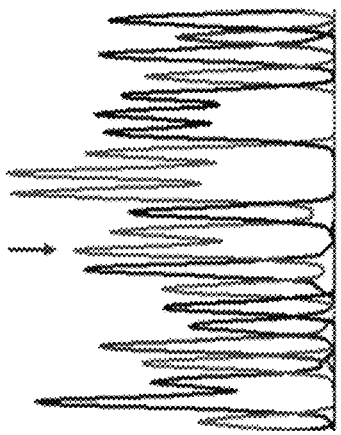
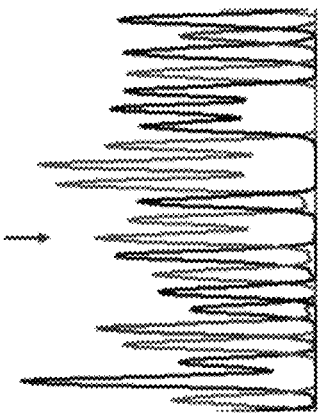
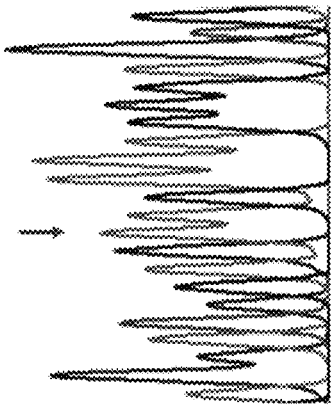

Fig. 9
150nM ADAR59-2
150nM ADAR59-10
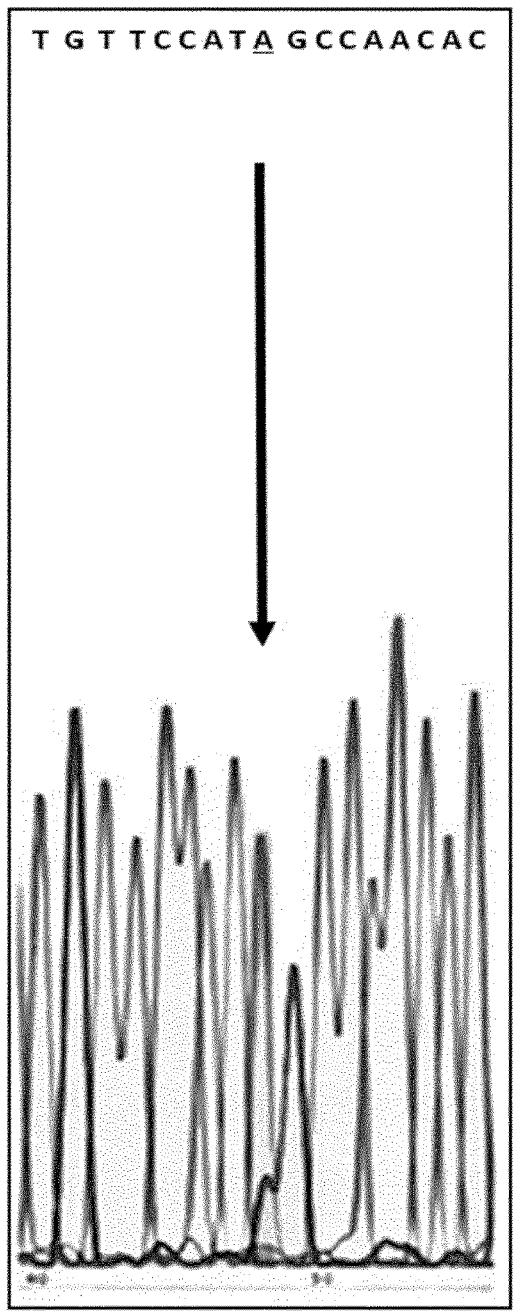
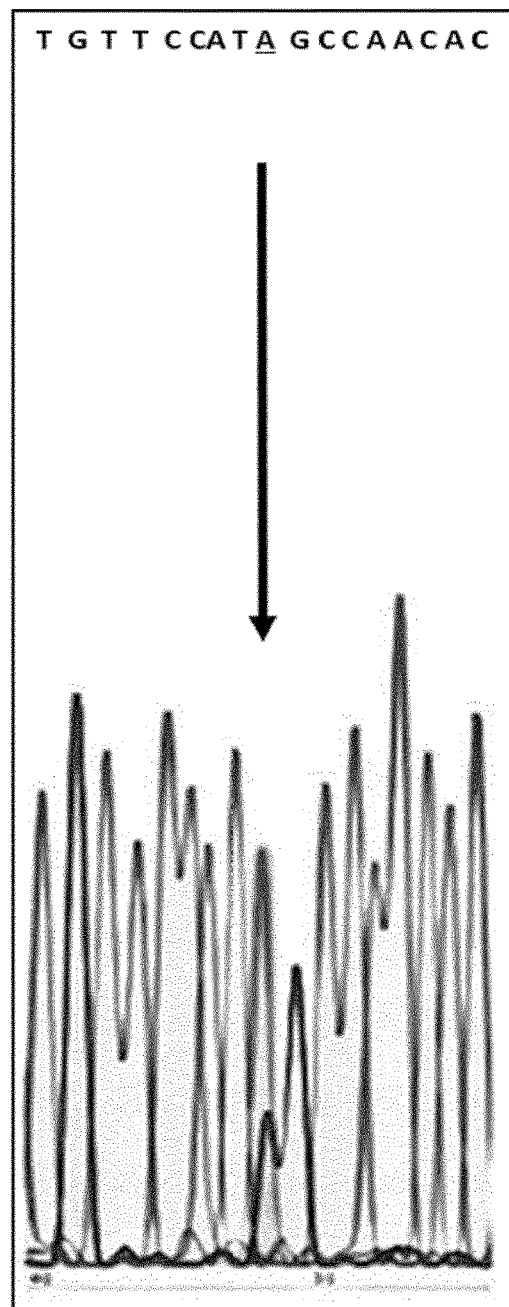

CHEMICALLY MODIFIED SINGLE-STRANDED RNA-EDITING OLIGONUCLEOTIDES

RELATED APPLICATIONS

This application is a continuation of U.S. patent application Ser. No. 16/329,787, filed Mar. 1, 2019, which is a § 371 National Stage Application of PCT/EP2017/071912, filed Aug. 31, 2017, which claims priority to and the benefit of United Kingdom patent application No. 1614858.7, filed Sep. 1, 2016, United Kingdom patent application No. 1616374.3, filed Sep. 27, 2016, United Kingdom patent application No. 1621467.8, filed Dec. 16, 2016, United Kingdom patent application No. 1703034.7, filed Feb. 24, 2017, and United Kingdom patent application No. 1707508.6, filed May 10, 2017, the entire disclosures of each of which are incorporated herein by reference for all purposes.

REFERENCE TO SEQUENCE LISTING SUBMITTED ELECTRONICALLY

The content of the electronically submitted sequence listing in ASCII text file (Name 4430_0030006_Sequence_Listing_ST25.K Size: 9,949 bytes; and Date of Creation: Mar. 7, 2023) filed with the application is incorporated herein by reference in its entirety.

FIELD OF THE INVENTION

The invention relates to the field of medicine. In particular, it relates to the field of RNA editing, whereby an RNA sequence is targeted by a single-stranded antisense oligonucleotide to correct a genetic mutation and/or to alter the sequence of a specific target RNA. More in particular, the invention relates to chemical modifications of the single-stranded RNA-editing oligonucleotides that render the oligonucleotides more stable and increase their RNA-editing efficiency.

BACKGROUND OF THE INVENTION

RNA editing is a natural process through which eukaryotic cells alter the sequence of their RNA molecules, often in a site-specific and precise way, thereby increasing the repertoire of genome encoded RNAs by several orders of magnitude. RNA editing enzymes have been described for eukaryotic species throughout the animal and plant kingdoms, and these processes play an important role in managing cellular homeostasis in metazoans from the simplest life forms such as *Caenorhabditis elegans*, to humans. Examples of RNA editing are adenosine (A) to inosine (I) and cytidine (C) to uridine (U) conversions through enzymes called adenosine deaminase and cytidine deaminase, respectively. The most extensively studied RNA editing system is the adenosine deaminase enzyme.

Adenosine deaminase is a multidomain protein, comprising a recognition domain and a catalytic domain. The recognition domain recognizes a specific double-stranded RNA (dsRNA) sequence and/or conformation, whereas the catalytic domain converts an adenosine into an inosine in a nearby, more or less predefined, position in the target RNA, by deamination of the nucleobase. Inosine is read as guanosine by the translational machinery of the cell, meaning that, if an edited adenosine is in a coding region of an mRNA or pre-mRNA, it can recode the protein sequence.

A-to-I conversions may also occur in 5' non-coding sequences of a target mRNA, creating new translational start sites upstream of the original start site, which gives rise to N-terminally extended proteins. Editing events can also occur at 3' UTRs and affect miRNA-based regulation and polyadenylation. In addition, A-to-I conversions may take place in splice elements in introns or exons in pre-mRNAs, thereby altering the pattern of splicing. As a consequence, exons may be included or skipped. The adenosine deaminases are part of a family of enzymes referred to as Adenosine Deaminases acting on RNA (ADAR), including human deaminases hADAR1, hADAR2 and hADAR3.

The use of oligonucleotides to edit a target RNA applying adenosine deaminase is known in the art. Montiel-Gonzalez et al. (PNAS 2013, 110(45):18285-18290) described the editing of a target RNA using a genetically engineered fusion protein, comprising an adenosine deaminase domain of the hADAR2 protein, fused to a bacteriophage lambda N protein, which recognises the boxB RNA hairpin sequence. The natural dsRNA binding domains of hADAR2 had been removed to eliminate the substrate recognition properties of the natural ADAR and replace it by the boxB recognition domain of lambda N-protein. The authors created an antisense oligonucleotide comprising a 'guide RNA' part that is complementary to the target sequence for editing, fused to a boxB portion for sequence specific recognition by the N-domain-deaminase fusion protein. By doing so, it was elegantly shown that the guide RNA oligonucleotide faithfully directed the adenosine deaminase fusion protein to the target site, resulting in guide RNA-directed site-specific A-to-I editing of the target RNA. The guide RNAs disclosed in Montiel-Gonzalez et al. (2013) are longer than 50 nucleotides in length. A disadvantage of this method in a therapeutic setting is the need for a fusion protein consisting of the boxB recognition domain of bacteriophage lambda N-protein, genetically fused to the adenosine deaminase domain of a truncated natural ADAR protein. It requires target cells to be either transduced with the fusion protein, which is a major hurdle, or that target cells are transfected with a nucleic acid construct encoding the engineered adenosine deaminase fusion protein for expression. The latter requirement constitutes no minor obstacle when editing is to be achieved in a multicellular organism, such as in therapy against human disease to correct a genetic disorder.

Vogel et al. (2014. Angewandte Chemie Int Ed 53:267-271) disclosed editing of RNA coding for eCFP and Factor V Leiden, using a benzylguanosine substituted guide RNA and a genetically engineered fusion protein, comprising the adenosine deaminase domains of ADAR1 or 2 (lacking the dsRNA binding domains) genetically fused to a SNAP-tag domain (an engineered 06-alkylguanosi ne-DNA-alkyl transferase). Although the genetically engineered artificial deaminase fusion protein could be targeted to a desired editing site in the target RNAs in HeLa cells in culture, through its SNAP-tag domain which is covalently linked to a guide RNA through a 5'-terminal 06-benzylguanosine modification, this system suffers from similar drawbacks as the genetically engineered ADARs described by Montiel-Gonzalez et al. (2013), in that it is not clear how to apply the system without having to genetically modify the ADAR first and subsequently transfect or transduct the cells harboring the target RNA, to provide the cells with this genetically engineered protein. Clearly, this system is not readily adaptable for use in humans, e.g. in a therapeutic setting.

Woolf et al. (1995. Proc Natl Acad Sci USA 92:8298-8302) disclosed a simpler approach, using relatively long single-stranded antisense RNA oligonucleotides (25-52 nucleotides in length) wherein the longer oligonucleotides (34-mer and 52 mer) could promote editing of the target RNA by endogenous ADAR because of the double-stranded nature of the target RNA and the hybridizing oligonucleotide. The oligonucleotides of Woolf et al. (1995) that were 100% complementary to the target RNA sequences only appeared to function in cell extracts or in amphibian (*Xenopus*) oocytes by microinjection, and suffered from severe lack of specificity: nearly all adenosines in the target RNA strand that was complementary to the antisense oligonucleotide were edited. An oligonucleotide, 34 nucleotides in length, wherein each nucleotide comprised a 2'-O-methyl modification, was tested and shown to be inactive in Woolf et al. (1995). In order to provide stability against nucleases, a 34-mer RNA, modified with 2'-O-methyl-modified phosphorothioate nucleotides at the 5'- and 3'-terminal 5 nucleotides, was also tested. It was shown that the central unmodified region of this oligonucleotide could promote editing of the target RNA by endogenous ADAR, with the terminal modifications providing protection against exonuclease degradation. Woolf et al. (1995) did not achieve deamination of a specific target adenosine in the target RNA sequence. Nearly all adenosines opposite an unmodified nucleotide in the antisense oligonucleotide were edited (therefore nearly all adenosines opposite nucleotides in the central unmodified region, if the 5'- and 3'-terminal 5 nucleotides of the antisense oligonucleotide were modified, or nearly all adenosines in the target RNA strand if no nucleotides were modified). ADAR acts on any double stranded RNA (dsRNA). Through a process sometimes referred to as 'promiscuous editing', the enzyme will edit multiple adenosines in a dsRNA. Hence, there is a need for methods and means that circumvent such promiscuous editing and that only target specified adenosines in a target RNA sequence. Vogel et al. (2014) showed that such off-target editing can be suppressed by using 2'-O-methyl-modified nucleotides in the oligonucleotide at positions opposite to the adenosines that should not be edited, and use a non-modified nucleotide directly opposite to the specifically targeted adenosine on the target RNA. However, the specific editing effect at the target nucleotide has not been shown to take place in that article without the use of recombinant ADAR enzymes that specifically form covalent bonds with the antisense oligonucleotide.

WO 2016/097212 discloses antisense oligonucleotides (AONs) for the targeted editing of RNA, wherein the AONs are characterized by a sequence that is complementary to a target RNA sequence (therein referred to as the 'targeting portion') and by the presence of a stem-loop structure (therein referred to as the 'recruitment portion'). Such oligonucleotides are referred to as 'axiomer AONs' or 'self-looping AONs'. The recruitment portion acts in recruiting a natural ADAR enzyme present in the cell to the dsRNA formed by hybridization of the target sequence with the targeting portion. Due to the recruitment portion there is no need for conjugated entities or presence of modified recombinant ADAR enzymes. WO 2016/097212 describes the recruitment portion as being a stem-loop structure mimicking either a natural substrate (e.g. the GluB receptor) or a Z-DNA structure known to be recognized by the dsRNA binding regions of ADAR enzymes. A stem-loop structure can be an intermolecular stem-loop structure, formed by two separate nucleic acid strands, or an intramolecular stem loop structure, formed within a single nucleic acid strand. The stem-loop structure of the recruitment portion as described in WO 2016/097212 is an intramolecular stem-loop structure, formed within the AON itself, and able to attract ADAR.

Yet another editing technique which uses oligonucleotides is known as CRISPR/Cas9 system, but this editing complex acts on DNA. The latter method suffers from the same drawback as the engineered ADAR systems described above, as it requires co-delivery to the target cell of the CRISPR/Cas9 enzyme, or an expression construct encoding the same, together with the guide oligonucleotide.

In view of the above, there remains a need for new techniques and compounds that can utilise endogenous cellular pathways and naturally available ADAR enzymes to specifically edit endogenous nucleic acids in mammalian cells, even in whole organisms, without the problems associated with the methods of the prior art.

SUMMARY OF THE INVENTION

The present invention does away with the drawbacks of the methods according to the prior art by providing a targeted approach to RNA editing using, in one embodiment, an antisense oligonucleotide (AON) capable of forming a double stranded complex with a target RNA sequence in a cell, preferably a human cell, for the deamination of a target adenosine in the target RNA sequence by an ADAR enzyme present in the cell, said AON comprising a Central Triplet of 3 sequential nucleotides, wherein the nucleotide directly opposite the target adenosine is the middle nucleotide of the Central Triplet, wherein the middle nucleotide in the Central Triplet does not have a 2'-O-methyl modification; and wherein 1, 2 or 3 nucleotides in said Central Triplet comprise a sugar modification and/or a base modification and/or a phosphodiester modification (such as phoshoro(di)thioate or amidate). The AON of the present invention is preferably in its basic structure a single stranded oligoribonucleotide.

The present invention also relates to the AON according to the invention for use in the treatment or prevention of a genetic disorder, preferably selected from the group consisting of: Cystic fibrosis, Hurler Syndrome, alpha-1-antitrypsin (A1AT) deficiency, Parkinson's disease, Alzheimer's disease, albinism, Amyotrophic lateral sclerosis, Asthma, ß-thalassemia, Cadasil syndrome, Charcot-Marie-Tooth disease, Chronic Obstructive Pulmonary Disease (COPD), Distal Spinal Muscular Atrophy (DSMA), Duchenne/Becker muscular dystrophy, Dystrophic Epidermolysis bullosa, Epidermolysis bullosa, Fabry disease, Factor V Leiden associated disorders, Familial Adenomatous Polyposis, Galactosemia, Gaucher's Disease, Glucose-6-phosphate dehydrogenase deficiency, Haemophilia, Hereditary Hemachromatosis, Hunter Syndrome, Huntington's disease, Inflammatory Bowel Disease (IBD), Inherited polyagglutination syndrome, Leber congenital amaurosis, Lesch-Nyhan syndrome, Lynch syndrome, Marfan syndrome, Mucopolysaccharidosis, Muscular Dystrophy, Myotonic dystrophy types I and II, neurofibromatosis, Niemann-Pick disease type A, B and C, NY-eso1 related cancer, Peutz-Jeghers Syndrome, Phenylketonuria, Pompe's disease, Primary Ciliary Disease, Prothrombin mutation related disorders, such as the Prothrombin G20210A mutation, Pulmonary Hypertension, Retinitis Pigmentosa, Sandhoff Disease, Severe Combined Immune Deficiency Syndrome (SCID), Sickle Cell Anemia, Spinal Muscular Atrophy, Stargardt's Disease, Tay-Sachs Disease, Usher syndrome, X-linked immunodeficiency, Sturge-Weber Syndrome, and cancer.

The invention also relates to a method for the deamination of a specific target adenosine present in a target RNA sequence in a cell, said method comprising the steps of: providing said cell with an AON according to the invention; allowing uptake by the cell of said AON; allowing annealing of said AON to the target RNA sequence; allowing a mammalian ADAR enzyme comprising a natural dsRNA binding domain as found in the wild type enzyme to deaminate said target adenosine in said target RNA sequence to an inosine; and, optionally identifying the presence of said inosine in the RNA sequence.

In preferred embodiments of the present invention the target RNA sequence encodes CFTR (e.g. to edit a 1784G>A mutation), CEP290 (e.g. to edit a c.2991+1655A>G mutation), alpha1-antitrypsin (A1AT; e.g. to edit a 9989G>A mutation; or a 1096G>A mutation), Guanine Nucleotide Binding Protein (GNAQ; e.g. to edit a 548G>A mutation), or LRRK2 (e.g. to edit a G6055 mutation), or wherein the target RNA is encoded by the IDUA gene (e.g. to edit a c.1205G>A (W402X) mutation).

BRIEF DESCRIPTION OF THE DRAWINGS

FIG. 1A and FIG. 1B show the complementarity of an antisense oligonucleotide (AON; upper strand) to the human mutated SERPINA1 target RNA sequence (lower strand; SEQ ID NO: 1), with the target adenosine A in bold. The sequence of the AONs of the ADAR60 series is here shown from 3' to 5' (in contrast to the direction as it is shown in FIGS. 2A-D), with the Central Triplet of the AON underlined. Positions in the Central Triplet that are modified as described in the provided examples are indicated by the letters YXZ.

FIGS. 2A-2D show the antisense oligonucleotides (AONs) and sense oligonucleotide (SON) for testing RNA editing and stability assessment as disclosed herein. Independent sequences have a SEQ ID NO as indicated. Specific YXZ base modifications are mentioned in the third column. Lower case nucleotides are RNA and 2'-O-methyl modified. Upper case nucleotides are RNA, except for bracketed [NNN] nucleotides, which is DNA. Lower case nucleotides depicted as (nnn) are 2'-fluoro RNA modified nucleotides. Lower case nucleotides depicted as <nnn> are 2'-NH$_2$ RNA modified nucleotides. Nucleotides depicted as {N} are *Unlocked Nucleic Acid* (UNA). idT indicates a 3' inverted T modification which enhances the resistance to degradation and also blocks the 3'-terminus of AON from extension during PCR amplification. *=phosphorothioate linkages; = 3'-methylenephosphonate linkages;"=5'-methylenephosphonate linkages; ^=3'-phosphoroamidate linkages; #=2'-5' phosphodiester linkages.

FIG. 4A and FIG. 4B show the complementarity of an AON (upper strand) to the human mutated IDUA target RNA sequence (lower strand; SEQ ID NO: 2), with the target adenosine A in bold. The sequence of the AONs of the ADAR68 series is here shown from 3' to 5' (in contrast to the direction as it is shown in FIGS. 2A-D), with the Central Triplet of the AON underlined. Positions in the Central Triplet that are modified as described in the provided examples are indicated by the letters XXY.

FIGS. 8A-8D show the Sanger sequencing analysis of PCR fragments generated by RT-PCR after in vitro editing assay using HEK293 cell lysate with overexpressed ADAR2 and a SERPINA1 mutant ssRNA target. ADAR60-1 (FIG. 8A) and ADAR60-15 (FIG. 8B) were used, see FIGS. 2A-D. Negative controls were an identical assay with ADAR60-15 but without cell lysate (FIG. 8C), and an identical assay using the HEK293 cell lysate (with ADAR2 overexpression) in the absence of AON (FIG. 8D). The sequence above all panels is SEQ ID NO:35.

FIG. 9 shows the sequencing results of the RT-PCR amplified GFP RNA from cells that stably express the GFP W57X construct and that were transfected with ADAR2 and separately with two oligonucleotides (ADAR59-2 and ADAR59-10), wherein the adenine in the Central Triplet of ADAR59-10 was a 2-aminopurine. ADAR59-2 does not have that modification, see FIGS. 2A-D. It shows the enhancing effect of this particular modification on RNA editing efficiency. The sequence above both panels is SEQ ID NO:36.

FIG. 10B is SEQ ID NO:37.

DETAILED DESCRIPTION OF THE INVENTION

Figure 3A:
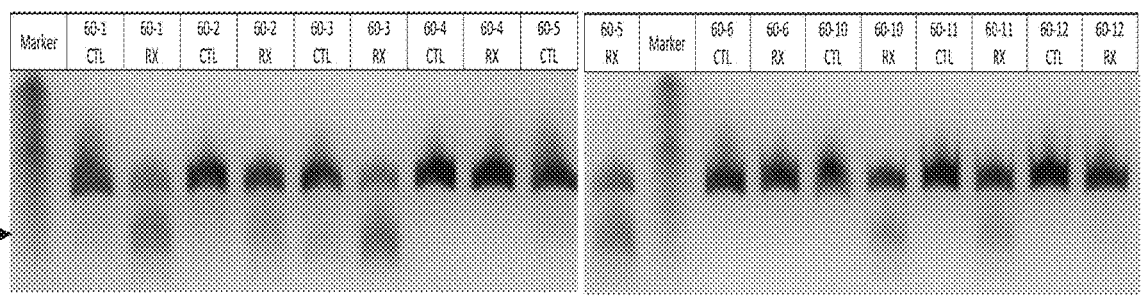
FIGS. 3A-3C show the nuclease resistance of AONs, assayed by denaturing gel electrophoresis after incubation in FBS-containing medium (indicated by RX). Controls were incubated in PBS (CTL). Identities of the AONs (ADAR60-1 through ADAR60-21) are indicated above the panel (abbreviated to 60-1 through 60-21, see also FIGS. 2A-D). The lower bands (indicated by an arrow) are degradation products resulting from cleavage of the AONs, while the upper bands are the full-length AONs. The Marker lanes contain Low Molecular Weight Marker, 10-100 nt (Affymetrix), with 14 oligonucleotide fragments at 5 nt (10 nt-50 nt) and 10 nt (50 nt-100 nt) increments. Susceptibility to degradation is indicated by the ratio of the bands, with a higher prevalence of the lower product suggesting lower stability.

As discussed above, WO 2016/097212 discloses AONs for the targeted editing of RNA, wherein the AONs are characterized by a 'targeting portion' and a 'recruitment portion'. WO 2016/097212 describes the recruitment portion as being a stem-loop structure mimicking either a natural substrate (e.g. the GluB receptor) or a Z-DNA structure known to be recognized by the dsRNA binding regions of ADAR enzymes. The stem-loop structure of the recruitment portion as described in WO 2016/097212 is an intramolecular stem-loop structure, formed within the AON itself, and able to attract ADAR. There are potential disadvantages in having AONs that are very long because of such structures, such as problems with manufacturing, stability, side-effects and they are more expensive to produce than shorter versions.

The AONs of the present invention do not comprise a recruitment portion as described in WO 2016/097212. The AONs of the present invention do not comprise a portion that is capable of forming an intramolecular stem-loop structure. The AONs of the present invention are shorter, which makes them cheaper to produce, easier to use and easier to manufacture. Furthermore, they do not have the disadvantage of potentially sequestering ADAR enzymes from their normal function in the cell. Unexpectedly, it was found that AONs that are complementary to a target RNA for deaminating a target adenosine present in a target RNA sequence to which the AON is complementary, but—importantly—lack a recruitment portion as described above, appeared still capable of harnessing ADAR enzymes present in the cell to edit the target adenosine. In a preferred aspect the AON of the present invention comprises a mismatch at the position of the target adenosine, wherein the opposite nucleotide is a cytidine. Also when a uridine is opposite the target adenosine (which would in fact not be a mismatch), the AON is capable of bringing about deamination of the target adenosine. PCT/EP2017/065467 describes that additional mismatches (resulting in so-called 'bulges' in the formed dsRNA, caused by nucleotides in the AON that do not form perfect base pairs with the target RNA according to the Watson-Crick base pairing rules) are tolerable, in some cases preferable, but not essential for specific targeted editing of the target RNA sequence. The number of bulges in the AON (when it hybridises to its RNA target sequence) may be one (usually the bulge formed at the target adenosine position) or more, depending on the length of the AON. The additional bulge-inducing mismatches may be upstream as well as downstream of the target adenosine. The bulges may be single-mismatch bulges (caused by one mismatching base pair) or multi-mismatch bulges (caused by more than one consecutive mismatching base pairs, preferably two or three consecutive mismatching base pairs).

The AONs according to the present invention have certain advantages over the oligonucleotides described in WO 2016/097212 and PCT/EP2017/065467, in that there is no need for hairpin or stem-loop structures, which allow the AONs of the present invention to be (considerably) shorter. The oligonucleotides described in WO 2016/097212 bear the potential risk of sequestering ADAR enzyme present in the cell. By sequestering in this context it is meant that a natural ADAR protein may bind to the oligonucleotides even in the absence of the formation of a dsRNA complex between the targeting portion of the oligonucleotide and the target RNA. This direct binding of ADAR to the oligonucleotides due to the presence of an intramolecular stem-loop structure, in the absence of target RNA sequences does not take place when using the AONs of the present invention, which do not comprise a portion that is capable of forming an intramolecular stem-loop structure. There are many instances where the presence of the hairpin and/or (stem-) loop structures is preferably avoided.

It is an important aspect of the invention that the AON comprises one or more nucleotides with one or more sugar modifications. Thereby, a single nucleotide of the AON can have one, or more than one sugar modification. Within the AON, one or more nucleotide(s) can have such sugar modification(s).

It is an important aspect of the invention that the nucleotide within the AON of the present invention that is opposite to the nucleotide that needs to be edited does not contain a 2'-O-methyl modification (herein and elsewhere often referred to as a 2'-OMe group, as 2'-O-methylation, or as a 2'-O-methyl group). It is preferred that the nucleotides that are directly 3' and 5' of this nucleotide (the 'neighbouring nucleotides' in the Central Triplet) also lack such a chemical modification, although it is believed that it is tolerated that one or both of the neighbouring nucleotides may contain a 2'-O-alkyl group (such as a 2'-O-methyl group). Either one, or both neighbouring nucleotides or all three nucleotides of the Central Triplet may be 2'-OH or a compatible substitution (as defined herein).

Another important aspect of the AON of the present invention is that it does not have a portion (which is not complementary to the target sequence or the region that comprises the target adenosine) that allows the AON in itself to fold into an intramolecular hairpin or other type of (stem-) loop structure (herein also referred to as "auto-looping" or "self-looping") under physiological conditions, and which may potentially act as a structure that sequesters ADAR. In a preferred aspect, the single stranded AON of the present invention is completely complementary with the target RNA, although it may optionally mismatch at several positions, especially the position at the target adenosine.

Preferred AONs of the present invention do not include a 5'-terminal O6-benzylguanosine or a 5'-terminal amino modification, and are not covalently linked to a SNAP-tag domain (an engineered O6-alkylguanosine-DNA-alkyl transferase) in contrast to Vogel et al. (2014). The SNAP-tag domain is derived from the human DNA repair protein O6-alkylguanosine-DNA-alkyl transferase (AGT) and can be covalently labelled in living cells using O6-benzylguanosine derivatives. Vogel et al. (2014) discloses guide RNAs with a total length of either 20 or 17 nucleotides, wherein the first three nucleotides at the 5' end do not bind to the target RNA sequence, but link the guide RNA to the SNAP-tag domain. The portion of the guide RNA which binds to the target RNA sequence is therefore either 14 or 17 nucleotides in length. Guide RNAs, of the same lengths, with a 5'-terminal amino modification in place of the 5'-terminal O6-benzylguanosine modification are also disclosed in Vogel et al. (2014), however only very little, or no deamination or the target RNA sequence was detected. In one embodiment, the AON of the present invention comprises 0, 1, 2 or 3 mismatches with the target RNA sequence, wherein a single mismatch may comprise multiple sequential nucleotides.

Similarly, a preferred AON of the present invention does not include a boxB RNA hairpin sequence, in contrast to Montiel-Gonzalez et al (2013). The boxB RNA hairpin sequence used in Montiel-Gonzalez et al. (2013) is a short stretch of RNA of 17 nucleotides that is recognized by the bacteriophage lambda N-protein. Transcription of downstream genes in the early operons of bacteriophage requires a promoter-proximal element known as nut. This site acts in cis in the form of RNA to assemble a transcription anti-termination complex which is composed of a bacteriophage lambda N protein and host factors. The nut-site RNA contains a small stem-loop structure called boxB. The boxB RNA hairpin sequence is known in the art as an interrupted palindrome with the potential to form a hairpin (stem-loop) structure. Its sequence varies among relatives of bacteriophage lambda which encode distinct genome specific N homologues.

Neither Vogel et al. (2014), nor Montiel-Gonzalez et al (2013) use a mammalian ADAR enzyme present in the cell, wherein the ADAR enzyme comprises its natural dsRNA binding domain as found in the wild-type enzyme. Vogel et al. (2014) uses a genetically engineered fusion protein comprising the adenosine deaminase domain of ADAR1 or 2 fused to a SNAP-tag domain and Montiel-Gonzalez et al uses a genetically engineered fusion protein comprising the adenosine deaminase domain of the hADAR2 protein, fused to the boxB recognition domain of bacteriophage lambda N protein. In contrast to the prior art, the AONs of the present invention use a mammalian ADAR enzyme present in the cell, wherein the ADAR enzyme comprises its natural dsRNA binding domain as found in the wild type enzyme. There is therefore no need to incorporate a boxB RNA hairpin sequence, a 5'-terminal O6-benzylguanosine, a 5'-terminal amino modification, or a SNAP-tag domain into the AON of the present invention, to allow recruitment of ADAR. The AONs according to the present invention therefore have certain advantages over the oligonucleotides described in Vogel et al. (2014) and Montiel-Gonzalez et al (2013). The AONs according to the present invention can utilise endogenous cellular pathways and naturally available ADAR enzymes to specifically edit a target adenosine in a target RNA sequence. In one embodiment, an AON of the invention is not covalently linked to a human 06-alkylguanosine-DNA-alkyl transferase. Preferably, an AON of the invention is not covalently linked to a polypeptide. In another aspect of the AON of the present invention, the AON does not have a 5' cap. In eukaryotes, the 5' cap consists of a guanosine nucleotide connected to the RNA via a 5' to 5' triphosphate linkage. This guanosine is methylated on the 7 position and is referred to as a 7-methylguanosine.

AONs of the invention are capable of deamination of a specific target adenosine nucleotide in a target RNA sequence. Thus, ideally only one adenosine is deaminated. Alternatively 1, 2, or 3 adenosine nucleotides are deaminated, for instance when target adenosines are in close proximity of each other. It would then require the presence of two or more 'Central Triplets' in a single AON, and depending of the distances, such may be used. However, if the distance is too big to cover multiple target adenosines by a single AON, the AON preferably comprises only one Central Triplet opposite the specified and single target adenosine.

Taking the features of the AONs of the present invention together: there is no need for modified recombinant ADAR expression; there is no need for conjugated entities attached to the AON; or the presence of long recruitment portions that are not complementary to the target RNA sequence. Besides that, the AON of the present invention does allow for the specific deamination of a target adenosine present in the target RNA sequence to an inosine by a natural ADAR enzyme comprising a natural dsRNA binding domain as found in the wild-type enzyme, without the risk of promiscuous editing elsewhere in the dsRNA complex.

The recruitment of cytidine deaminase to a target site works in the same way as for the adenosine deaminases hADAR1 and hADAR2. However, cytidine deaminases have different binding requirements and recognize different structures in their target RNA sequences that determine editing of the cytidine. One particularly well studied cytidine deaminase is human Apobec1. The general principle of RNA editing using an oligonucleotide construct to target an editing site and to recruit a resident, naturally present, editing entity remains the same for cytidine deaminases, and is part of the invention disclosed and claimed herein.

Analysis of natural targets of ADAR enzymes has indicated that these generally include mismatches between the two strands that form the RNA helix edited by ADAR1 or 2. It has been suggested that these mismatches enhance the specificity of the editing reaction (Stefl et al. 2006. Structure 14(2):345-355; Tian et al. 2011. Nucleic Acids Res 39(13): 5669-5681). Characterization of optimal patterns of paired/mismatched nucleotides between the AONs and the target RNA also appears crucial for development of efficient ADAR-based AON therapy.

Another improved feature of the AONs of the present invention is the use of specific nucleotide modifications at predefined spots to ensure stability as well as proper ADAR binding and activity. These changes may vary and may include modifications in the backbone of the AON, in the sugar moiety of the nucleotides as well as in the nucleobases or the phosphodiester linkages. They may also be variably distributed throughout the sequence of the AON. Specific modifications may be needed to support interactions of different amino acid residues within the RNA-binding domains of ADAR enzymes, as well as those in the deaminase domain. For example, phosphorothioate linkages between nucleotides or 2'-O-methyl modifications may be tolerated in some parts of the AON, while in other parts they should be avoided so as not to disrupt crucial interactions of the enzyme with the phosphate and 2'-OH groups. Part of these design rules are guided by the published structures of ADAR2, while others have to be defined empirically. Different preferences may exist for ADAR1 and ADAR2. The modifications should also be selected such that they prevent degradation of the AONs.

Specific nucleotide modifications may also be necessary to enhance the editing activity on substrate RNAs where the target sequence is not optimal for ADAR editing. Previous work has established that certain sequence contexts are more amenable to editing. For example, the target sequence 5'-UAG-3' (with the target A in the middle) contains the most preferred nearest-neighbor nucleotides for ADAR2, whereas a 5'-CAA-3' target sequence is disfavored (Schneider et al. 2014. Nucleic Acids Res 42(10):e87). The recent structural analysis of ADAR2 deaminase domain hints at the possibility of enhancing editing by careful selection of the nucleotides that are opposite to the target trinucleotide. For example, the 5'-CAA-3' target sequence, paired to a 3'-GCU-5' sequence on the opposing strand (with the A-C mismatch formed in the middle), is disfavored because the guanosine base sterically clashes with an amino acid side chain of ADAR2. However, here it is postulated that a smaller nucleobase, such as inosine, could potentially fit better into this position without causing steric clashes, while still retaining the base-pairing potential to the opposing cytosine. Modifications that could enhance activity of suboptimal sequences include the use of backbone modifications that increase the flexibility of the AON or, conversely, force it into a conformation that favors editing.

Definitions of Terms as Used Herein

The 'Central Triplet' as used and defined herein are the three nucleotides opposite the target adenosine in the target RNA, wherein the middle nucleotide in the Central Triplet is directly opposite the target adenosine. The Central Triplet does not have to be in the middle (in the centre) of the AON, it may be located more to the 3' as well as to the 5' end of the AON, whatever is preferred for a certain target. Central in this aspect has therefore more the meaning of the triplet that is in the centre of catalytic activity when it comes to chemical modifications and targeting the target adenosine. It should also be noted that the AONs are sometimes depicted from 3' to 5', especially when the target sequence is shown from 5' to 3'. However, whenever herein the order of nucleotides within the AON is discussed it is always from 5' to 3' of the AON. For example, the first nucleotide of the Central Triplet in ADAR60-1 is the U of the 5'-UCG-3' triplet. The position can also be expressed in terms of a particular nucleotide within the AON while still adhering to the 5' to 3' directionality, in which case other nucleotides 5' of the said nucleotide are marked as negative positions and those 3' of it as positive positions. For example, the C in the Central triplet is the nucleotide (at the 0 position) opposite the targeted adenosine and the U would in this case be the −1 nucleotide and the G would then be the +1 nucleotide, etc.

As outlined herein, and in most examples of AONs disclosed herein, the nucleotides outside the Central triplet are 2'-O-methyl modified. However, this is not a requirement of the AONs of the present invention. The use of 2'-O-methylation in those nucleotides assures a proper stability of those parts of the AON, but other modifications may be applied as well, such as 2'-O-methoxyethyl (2'-O-MOE) modifications.

The terms 'adenine', 'guanine', 'cytosine', 'thymine', 'uracil' and 'hypoxanthine' (the nucleobase in inosine) as used herein refer to the nucleobases as such.

The terms 'adenosine', 'guanosine', 'cytidine', 'thymidine', 'uridine' and 'inosine', refer to the nucleobases linked to the (deoxy)ribosyl sugar.

The term 'nucleoside' refers to the nucleobase linked to the (deoxy)ribosyl sugar.

The term 'nucleotide' refers to the respective nucleobase-(deoxy)ribosyl-phospholinker, as well as any chemical modifications of the ribose moiety or the phospho group. Thus the term would include a nucleotide including a locked ribosyl moiety (comprising a 2'-4' bridge, comprising a methylene group or any other group, well known in the art), a nucleotide including a linker comprising a phosphodiester, phosphotriester, phosphoro(di)thioate, methylphosphonates, phosphoramidate linkers, and the like.

Sometimes the terms adenosine and adenine, guanosine and guanine, cytosine and cytidine, uracil and uridine, thymine and thymidine, inosine and hypo-xanthine, are used interchangeably to refer to the corresponding nucleobase, nucleoside or nucleotide.

Sometimes the terms nucleobase, nucleoside and nucleotide are used interchangeably, unless the context clearly requires differently.

Whenever reference is made to an 'oligonucleotide', both oligoribonucleotides and deoxyoligoribonucleotides are meant unless the context dictates otherwise. Whenever reference is made to an 'oligoribonucleotide' it may comprise the bases A, G, C, U or I. Whenever reference is made to a 'deoxyoligoribonucleotide' it may comprise the bases A, G, C, T or I. In a preferred aspect, the AON of the present invention is an oligoribonucleotide that may comprise chemical modifications.

Whenever reference is made to nucleotides in the oligonucleotide construct, such as cytosine, 5-methylcytosine, 5-hydroxymethylcytosine, Pyrrolocytidine, and β-D-Glucosyl-5-hydroxymethylcytosine are included; when reference is made to adenine, 2-aminopurine, 2,6-diaminopurine, 3-deazaadenosine, 7-deazaadenosine, 8-azidoadenosine, 8-methyladenosine, 7-aminomethyl-7-deazaguanosine, 7-deazaguanosine, N6-Methyladenine and 7-methyladenine are included; when reference is made to uracil, 5-methoxyuracil, 5-methyluracil, dihydrouracil, pseudouracil, and thienouracil, dihydrouracil, 4-thiouracil and 5-hydroxymethyluracil are included; when reference is made to guanosine, 7-methylguanosine, 8-aza-7-deazaguanosine, thienoguanosine and 1-methylguanosine are included.

Whenever reference is made to nucleosides or nucleotides, ribofuranose derivatives, such as 2'-deoxy, 2'-hydroxy, 2-fluororibose and 2'-O-substituted variants, such as 2'-O-methyl, are included, as well as other modifications, including 2'-4' bridged variants.

Whenever reference is made to oligonucleotides, linkages between two mono-nucleotides may be phosphodiester linkages as well as modifications thereof, including, phosphodiester, phosphotriester, phosphoro(di)thioate, methylphosphonate, phosphor-amidate linkers, and the like.

The term 'comprising' encompasses 'including' as well as 'consisting', e.g. a composition 'comprising X' may consist exclusively of X or may include something additional, e.g. X+Y.

The term 'about' in relation to a numerical value x is optional and means, e.g. x±10%.

The word 'substantially' does not exclude 'completely', e.g. a composition which is 'substantially free from Y' may be completely free from Y. Where relevant, the word 'substantially' may be omitted from the definition of the invention.

The term 'downstream' in relation to a nucleic acid sequence means further along the sequence in the 3' direction; the term 'upstream' means the converse. Thus in any sequence encoding a polypeptide, the start codon is upstream of the stop codon in the sense strand, but is downstream of the stop codon in the antisense strand.

References to 'hybridisation' typically refer to specific hybridisation, and exclude non-specific hybridisation. Specific hybridisation can occur under experimental conditions chosen, using techniques well known in the art, to ensure that the majority of stable interactions between probe and target are where the probe and target have at least 70%, preferably at least 80%, more preferably at least 90% sequence identity.

The term 'mismatch' is used herein to refer to opposing nucleotides in a double stranded RNA complex which do not form perfect base pairs according to the Watson-Crick base pairing rules. Mismatch base pairs are G-A, C-A, U-C, A-A, G-G, C-C, U-U base pairs. In some embodiments AONs of the present invention comprise 0, 1, 2 or 3 mismatches, wherein a single mismatch may comprise several sequential nucleotides. Wobble base pairs are: G-U, I-U, I-A, and I-C base pairs.

An AON according to the present invention may be chemically modified almost in its entirety, for example by providing all nucleotides with a 2'-O-methylated sugar moiety (2'-OMe). However, the nucleotide opposite the target adenosine does not comprise the 2'-O-methyl modification, and in yet a further preferred aspect, at least one of the two neighbouring nucleotides flanking the nucleotide opposing the target adenosine does not comprise a 2'-O-methyl modification. Complete modification, wherein all nucleotides in the AON holds a 2'-O-methyl modification (including the Central Triplet) results in a non-functional oligonucleotide as far as RNA editing goes, presumably because it hinders the ADAR activity at the targeted position. In general, an adenosine in a target RNA can be protected from editing by providing an opposing nucleotide with a 2'-O-methyl group, or by providing a guanosine or adenosine as opposing base, as these two nucleobases are also able to reduce editing of the opposing adenosine.

Various chemistries and modification are known in the field of oligonucleotides that can be readily used in accordance with the invention. The regular internucleosidic linkages between the nucleotides may be altered by mono- or di-thioation of the phosphodiester bonds to yield phosphorothioate esters or phosphorodithioate esters, respectively. Other modifications of the internucleosidic linkages are possible, including amidation and peptide linkers. In a preferred aspect the AONs of the present invention have one, two, three, four or more phosphorothioate linkages between the most terminal nucleotides of the AON (hence, preferably at both the 5' and 3' end), which means that in the case of four phosphorothioate linkages, the ultimate 5 nucleotides are linked accordingly. It will be understood by the skilled person that the number of such linkages may vary on each end, depending on the target sequence, or based on other aspects, such as toxicity.

The ribose sugar may be modified by substitution of the 2'-0 moiety with a lower alkyl (C1-4, such as 2'-O-methyl), alkenyl (C2-4), alkynyl (C2-4), methoxyethyl (2'-O-MOE), —H (as in DNA) or other substituent. Preferred substituents of the 2'-OH group are a methyl, methoxyethyl or 3,3'-dimethylallyl group. The latter is known for its property to inhibit nuclease sensitivity due to its bulkiness, while improving efficiency of hybridization (Angus & Sproat. 1993. FEBS Vol. 325, no. 1, 2, 123-7). Alternatively, locked nucleic acid sequences (LNAs), comprising a 2'-4' intramolecular bridge (usually a methylene bridge between the 2' oxygen and 4' carbon) linkage inside the ribose ring, may be applied. Purine nucleobases and/or pyrimidine nucleobases may be modified to alter their properties, for example by amination or deamination of the heterocyclic rings. The exact chemistries and formats may depend from oligonucleotide construct to oligonucleotide construct and from application to application, and may be worked out in accordance with the wishes and preferences of those of skill in the art. It is believed in the art that 4 or more consecutive DNA nucleotides (4 consecutive deoxyriboses) in an oligonucleotide create so-called gapmers that—when annealed to their RNA cognate sequences—induce cleavage of the target RNA by RNaseH. According to the present invention, RNaseH cleavage of the target RNA is generally to be avoided as much as possible.

The AON according to the invention should normally be longer than 10 nucleotides, preferably more than 11, 12, 13, 14, 15, 16, still more preferably more than 17 nucleotides. In one embodiment the AON according to the invention is longer than 20 nucleotides. The oligonucleotide according to the invention is preferably shorter than 100 nucleotides, still more preferably shorter than 60 nucleotides. In one embodiment the AON according to the invention is shorter than 50 nucleotides. In a preferred aspect, the oligonucleotide according to the invention comprises 18 to 70 nucleotides, more preferably comprises 18 to 60 nucleotides, and even more preferably comprises 18 to 50 nucleotides. Hence, in a most preferred aspect, the oligonucleotide of the present invention comprises 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides.

It is known in the art, that RNA editing entities (such as human ADAR enzymes) edit dsRNA structures with varying specificity, depending on a number of factors. One important factor is the degree of complementarity of the two strands making up the dsRNA sequence. Perfect complementarity of the two strands usually causes the catalytic domain of hADAR to deaminate adenosines in a non-discriminative manner, reacting more or less with any adenosine it encounters. The specificity of hADAR1 and 2 can be increased by ensuring a number of mismatches in the dsRNA, which presumably help to position the dsRNA binding domains in a way that has not been clearly defined yet. Additionally, the deamination reaction itself can be enhanced by providing an AON that comprises a mismatch opposite the adenosine to be edited. The mismatch is preferably created by providing a targeting portion having a cytidine opposite the adenosine to be edited. As an alternative, also uridines may be used opposite the adenosine, which, understandably, will not result in a 'mismatch' because U and A pair. Upon deamination of the adenosine in the target strand, the target strand will obtain an inosine which, for most biochemical processes, is "read" by the cell's biochemical machinery as a G. Hence, after A to I conversion, the mismatch has been resolved, because I is perfectly capable of base pairing with the opposite C in the targeting portion of the oligonucleotide construct according to the invention. After the mismatch has been resolved due to editing, the substrate is released and the oligonucleotide construct-editing entity complex is released from the target RNA sequence, which then becomes available for downstream biochemical processes, such as splicing and translation.

The desired level of specificity of editing the target RNA sequence may depend from application to application. Following the instructions in the present patent application, those of skill in the art will be capable of designing the complementary portion of the oligonucleotide according to their needs, and, with some trial and error, obtain the desired result.

The oligonucleotide of the invention will usually comprise the normal nucleotides A, G, U and C, but may also include inosine (I), for example instead of one or more G nucleotides.

To prevent undesired editing of adenosines in the target RNA sequence in the region of overlap with the oligonucleotide construct, the oligonucleotide may be chemically modified. It has been shown in the art, that 2'-O-methylation of the ribosyl-moiety of a nucleoside opposite an adenosine in the target RNA sequence dramatically reduces deamination of that adenosine by ADAR (Vogel et al. 2014). This is a severe drawback for using such AONs in therapeutic settings and it is a purpose of the present invention to solve, at least in part, that problem of having unmodified RNA nucleotides in an AON, which makes it prone to degradation.

RNA editing molecules in the cell will usually be proteinaceous in nature, such as the ADAR enzymes found in metazoans, including mammals. Preferably, the editing entity is an enzyme, more preferably an adenosine deaminase or a cytidine deaminase, still more preferably an adenosine deaminase. The ones of most interest are the human ADARs, hADAR1 and hADAR2, including any isoforms thereof such as hADAR1 p110 and p150. RNA editing enzymes known in the art, for which oligonucleotide constructs according to the invention may conveniently be designed, include the adenosine deaminases acting on RNA (ADARs), such as hADAR1 and hADAR2 in humans or human cells and cytidine deaminases. Human ADAR3 (hADAR3) has been described in the prior art, but reportedly has no deaminase activity. It is known that hADAR1 exists in two isoforms; a long 150 kDa interferon inducible version and a shorter, 100 kDa version, that is produced through alternative splicing from a common pre-mRNA. Consequently, the level of the 150 kDa isoform present in the cell may be influenced by interferon, particularly interferon-gamma (IFN-gamma). hADAR1 is also inducible by TNF-alpha. This provides an opportunity to develop combination therapy, whereby interferon-gamma or TNF-alpha and oligonucleotides according to the invention are administered to a patient either as a combination product, or as separate products, either simultaneously or subsequently, in any order. Certain disease conditions may already coincide with increased IFN-gamma or TNF-alpha levels in certain tissues of a patient, creating further opportunities to make editing more specific for diseased tissues.

Examples of chemical modifications in the AONs of the present invention are modifications of the sugar moiety, including by cross-linking substituents within the sugar (ribose) moiety (e.g. as in locked nucleic acids: LNA), by substitution of the 2'-O atom with alkyl (e.g. 2'-O-methyl), alkynyl (2'-O-alkynyl), alkenyl (2'-O-alkenyl), alkoxyalkyl (e.g. methoxyethyl: 2'-O-MOE) groups, having a length as specified above, and the like. In addition, the phosphodiester group of the backbone may be modified by thioation, dithioation, amidation and the like to yield phosphorothioate, phosphorodithioate, phosphoramidate, etc., internucleosidic linkages. The internucleotidic linkages may be replaced in full or in part by peptidic linkages to yield in peptidonucleic acid sequences and the like. Alternatively, or in addition, the nucleobases may be modified by (de)amination, to yield inosine or 2'6'-diaminopurines and the like. A further modification may be methylation of the C5 in the cytidine moiety of the nucleotide, to reduce potential immunogenic properties known to be associated with CpG sequences.

In case the dsRNA complex recruits ADAR enzymes to deaminate an A to an I in the target RNA sequence, the base-pair, mismatch, bulge or wobble between the adenosine to be edited and the opposite nucleotide may comprise an adenosine, a guanosine, an uridine or a cytidine residue, but preferably a cytidine residue. Except for the potential mismatch opposite the editing site (when no uridine is applied), the remaining portion of the AON may be perfectly complementary to the target RNA. However, as shown herein, in certain aspects the invention relates to AONs that comprise a limited number of imperfect matches. It will be understood by a person having ordinary skill in the art that the extent to which the editing entities inside the cell are redirected to other target sites may be regulated by varying the affinity of the oligonucleotides according to the invention for the recognition domain of the editing molecule. The exact modification may be determined through some trial and error and/or through computational methods based on structural interactions between the oligonucleotide and the recognition domain of the editing molecule.

In addition, or alternatively, the degree of recruiting and redirecting the editing entity resident in the cell may be regulated by the dosing and the dosing regimen of the oligonucleotide. This is something to be determined by the experimenter (in vitro) or the clinician, usually in phase I and/or II clinical trials. The invention concerns the modification of target RNA sequences in eukaryotic, preferably metazoan, more preferably mammalian cells. In principle the invention can be used with cells from any mammalian species, but it is preferably used with a human cell.

The invention can be used with cells from any organ e.g. skin, lung, heart, kidney, liver, pancreas, gut, muscle, gland, eye, brain, blood and the like. The invention is particularly suitable for modifying sequences in cells, tissues or organs implicated in a diseased state of a (human) subject. Such cells include but are not limited to epithelial cells of the lung or the gastrointestinal tract, cells of the reproductive organs, muscle cells, cells of the eye, cells of the skin, cells from tissues and organs such as liver, kidney, pancreas, immune cells, cancerous cells, gland cells, brain cells, and the like. The invention can also be used with mammalian cells which are not naturally present in an organism e.g. with a cell line or with an embryonic stem (ES) cell. The invention can be used with various types of stem cell, including pluripotent stem cells, totipotent stem cells, embryonic stem cells, induced pluripotent stem cells, etc. The cell can be located in vitro or in vivo. One advantage of the invention is that it can be used with cells in situ in a living organism, but it can also be used with cells in culture. In some embodiments cells are treated ex vivo and are then introduced into a living organism (e.g. re-introduced into an organism from whom they were originally derived). The invention can also be used to edit target RNA sequences in cells within a so-called organoid. Organoids can be thought of as three-dimensional in vitro-derived tissues but are driven using specific conditions to generate individual, isolated tissues (e.g. see Lancaster & Knoblich, Science 2014, vol. 345 no. 6194 1247125). In a therapeutic setting they are useful because they can be derived in vitro from a patient's cells, and the organoids can then be re-introduced to the patient as autologous material which is less likely to be rejected than a normal transplant. Thus, according to another preferred embodiment, the invention may be practised on organoids grown from tissue samples taken from a patient (e.g. from their gastrointestinal tract; see Sala et al. J Surg Res. 2009; 156(2):205-12, and also Sato et al. Gastroenterology 2011; 141:1762-72); upon RNA editing in accordance with the invention, the organoids, or stem cells residing within the organoids, may be used to transplant back into the patient to ameliorate organ function.

The cell to be treated will generally have a genetic mutation. The mutation may be heterozygous or homozygous. The invention will typically be used to modify point mutations, such as N to A mutations, wherein N may be G, C, U (on the DNA level T), preferably G to A mutations, or N to C mutations, wherein N may be A, G, U (on the DNA level T), preferably U to C mutations. Genes containing mutations of particular interest are discussed below. In some embodiments, however, the invention is used in the opposite way by introducing a disease-associated mutation into a cell line or an animal, in order to provide a useful research tool for the disease in question. As an example of creating a disease model, one can provide an oligonucleotide sequence that provides for the recruitment of editing activity in a human cell to create a mutation in the CEP290 gene, creating a cryptic splice site that forms the basis for a form of Leber's Congenital Amaurosis, the most common form of congenital child blindness. It can also be envisioned that non-mutated sequences are targeted for RNA editing, for instance to alter the splicing of a particular target RNA, such that a mutant version of that target gene is translated in another fashion, thereby relieving disease. The person skilled in the art is aware of all types of possibilities to modify target RNA for a wide variety of purposes.

A mutation to be reverted through RNA editing may have arisen on the level of the chromosome or some other form of DNA, such as mitochondrial DNA, or RNA, including pre-mRNA, ribosomal RNA or mitochondrial RNA. A change to be made may be in a target RNA of a pathogen, including fungi, yeasts, parasites, kinetoplastids, bacteria, phages, viruses etc, with which the cell or subject has been infected. Subsequently, the editing may take place on the RNA level on a target sequence inside such cell, subject or pathogen. Certain pathogens, such as viruses, release their nucleic acid, DNA or RNA into the cell of the infected host (cell). Other pathogens reside or circulate in the infected host. The oligonucleotide constructs of the invention may be used to edit target RNA sequences residing in a cell of the infected eukaryotic host, or to edit a RNA sequence inside the cell of a pathogen residing or circulating in the eukaryotic host, as long as the cells where the editing is to take place contain an editing entity compatible with the oligonucleotide construct administered thereto.

Without wishing to be bound by theory, the RNA editing through hADAR1 and hADAR2 is thought to take place on primary transcripts in the nucleus, during transcription or splicing, or in the cytoplasm, where e.g. mature mRNA, miRNA or ncRNA can be edited. Different isoforms of the editing enzymes are known to localize differentially, e.g. with hADAR1 p110 found mostly in the nucleus, and hADAR1 p150 in the cytoplasm. The RNA editing by cytidine deaminases is thought to take place on the mRNA level. Editing of mitochondrial RNA codons or non-coding sequences in mature mRNAs is not excluded.

The invention is used to make a change in a target RNA sequence in a eukaryotic cell through the use of an oligonucleotide that is capable of targeting a site to be edited and recruiting RNA editing entities resident in the cell to bring about the editing reaction(s). Preferred editing reactions are adenosine deaminations and cytidine deaminations, converting adenosines into inosines and cytidines into uridines, respectively. The changes may be in 5' or 3' untranslated regions of a target RNA, in (cryptic) splice sites, in exons (changing amino acids in protein translated from the target RNA, codon usage or splicing behaviour by changing exonic splicing silencers or enhancers, by introducing or removing start or stop codons), in introns (changing splicing by altering intronic splicing silencers or intronic splicing enhancers, branch points) and in general in any region affecting RNA stability, structure or functioning. The target RNA sequence may comprise a mutation that one may wish to correct or alter, such as a point mutation (a transition or a transversion). Alternatively, the target RNA sequence is deliberately mutated to create an altered phenotype (or genotype, in case of RNA based organisms, such as RNA viruses), where there was no mutation before. For example cell lines or animals may be made which carry changes (mutations) in a target RNA sequence, which may be used in assays or as (animal, organoid, etcetera) model systems to study disease, test experimental compounds against disease, and the like. The oligonucleotide constructs and methods according to the invention may be used in high throughput screening systems (in arrayed format) for making cell banks with a large variety of target RNAs, for example coding for a large variety of protein isoforms, for further experimentation, including compound screening, protein engineering and the like. The target RNA may be any cellular or viral RNA sequence, but is more usually a pre-mRNA or an mRNA with a protein coding function.

Purely for ease of reference, and without the intention to limit the invention, the following Table 1 is provided to illustrate the potential codon changes that can be brought about by adenosine deaminase editing directed by oligonucleotides of the invention. Table 1 particularly should not be interpreted as a limitation of the applicability of the invention to coding sequences in any RNA; as pointed out already, the invention can be practised on any RNA target comprising an adenosine, whether in a coding region, an intron, a non-coding exon (such as a 5'- or 3' untranslated region), in miRNAs, tRNAs, rRNAs and so on. To avoid any misunderstanding about the width of the applicability, changes that are inconsequential ('silent') from a coding perspective may still alter gene expression of a certain protein as some codons for the same amino acid may be more preferred than others and may lead, for instance, to different transcription stability or translation efficiency, causing the encoded protein to become more or less abundant than without the change.

TABLE 1

| Target codon | Amino acid | Corrected codon | Amino acid |
|---|---|---|---|
| AAA | Lys | GAA | Glu |
|  |  | AGA | Arg |
|  |  | AAG | Lys |
|  |  | GGA | Gly |
|  |  | AGG | Arg |
|  |  | GAG | Glu |
|  |  | GGG | Gly |
| AAC | Asn | GAC | Asp |
|  |  | AGC | Ser |
|  |  | GGC | Gly |
| AAG | Lys | GAG | Glu |
|  |  | AGG | Arg |
|  |  | GGG | Gly |

TABLE 1-continued

| Target codon | Amino acid | Corrected codon | Amino acid |
|---|---|---|---|
| AAU | Arg | GAU | Asp |
|  |  | AGU | Ser |
|  |  | GGU | Gly |
| ACA | Thr | GCA | Ala |
|  |  | ACG | Thr |
|  |  | GCG | Ala |
| ACC | Thr | GCC | Ala |
| ACG | Thr | GCG | Ala |
| ACU | Thr | GCU | Ala |
| AGA | Arg | GGA | Gly |
|  |  | AGG | Arg |
|  |  | GGG | Gly |
| AGC | Ser | GGC | Gly |
| AGG | Arg | GGG | Gly |
| AGU | Ser | GGU | Gly |
| AUA | Ile | GAU | Asp |
|  |  | AUG | Met |
|  |  | GUG | Val |
| AUC | Ile | GUC | Val |
| AUG | Met | GUG | Val |
| AUU | Ile | GUU | Val |
| CAA | Gln | CGA | Arg |
|  |  | CAG | Gln |
|  |  | CGG | Arg |
| CAC | His | CGC | Arg |
| CAG | Gln | CGG | Arg |
| CAU | His | CGU | Arg |
| CCA | Pro | CCG | Pro |
| CGA | Arg | CGG | Arg |
| CUA | Leu | CUG | Leu |
| GAA | Glu | GGA | Gly |
|  |  | GAG | Glu |
|  |  | GGG | Gly |
| GCA | Ala | GCG | Ala |
| GUA | Val | GUG | Val |
| GGA | Gly | GGG | Gly |
| GAC | Asp | GGC | Gly |
| GAG | Glu | GGG | Gly |
| GAU | Asp | GGU | Gly |
| UAA | Stop | UGA | Stop |
|  |  | UAG | Stop |
|  |  | UGG | Trp |
| UCA | Ser | UCG | Ser |
| UGA | Stop | UGG | Trp |
| UUA | Leu | UUG | Leu |
| UAC | Tyr | UGC | Cys |
| UAG | Stop | UGG | Trp |
| UAU | Tyr | UGU | Cys |

Particularly interesting target adenosines for editing using oligonucleotides according to the invention are those that are part of codons for amino acid residues that define key functions, or characteristics, such as catalytic sites, binding sites for other proteins, binding by substrates, localization domains, for co- or post-translational modification, such as glycosylation, hydroxylation, myristoylation, protein cleavage by proteases (to mature the protein and/or as part of the intracellular routing), and so forth.

A host of genetic diseases are caused by G-to-A mutations, and these are preferred target diseases because adenosine deamination at the mutated target adenosine will reverse the mutation to wild-type. However, reversal to wild-type may not always be necessary to obtain a beneficial effect. Modification of an A to a G in a target may also be beneficial if the wild-type nucleotide is other than a G. In certain circumstances this may be predicted to be the case, in others this may require some testing. In certain circumstances, the modification from an A in a target RNA to a G where the wild-type is not a G may be silent (not translated into a different amino acid), or otherwise non-consequential (for example an amino acid is substituted but it constitutes a conservative substitution that does not disrupt protein structure and function), or the amino acid is part of a functional domain that has a certain robustness for change. If the A-to-G transition brought about by editing in accordance with the invention is in a non-coding RNA, or a non-coding part of an RNA, the consequence may also be inconsequential or less severe than the original mutation. Those of ordinary skill in the art will understand that the applicability of the current invention is very wide and is not even limited to preventing or treating disease. The invention may also be used to modify transcripts to study the effect thereof, even if, or particularly when, such modification induces a diseased state, for example in a cell or a non-human animal model.

Preferred examples of genetic diseases that can be prevented and/or treated with oligonucleotides according to the invention are any disease where the modification of one or more adenosines in a target RNA will bring about a (potentially) beneficial change.

Transcribed RNA sequences that are potential target RNA sequences according to the invention, containing mutations of particular interest include, but are not limited to those transcribed from the CFTR gene (the cystic fibrosis transmembrane conductance regulator), dystrophin, huntingtin, neurofibromin 1, neurofibromin 2, the δ-globin chain of haemoglobin, CEP290 (centrosomal protein 290 kDa), the HEXA gene of the δ-hexosaminidase A, and any one of the Usher genes (e.g. USH2B encoding Usherin) responsible for a form of genetic blindness called Usher syndrome. A more extensive list is presented further below. The target sequence will be selected accordingly, and the oligonucleotide construct will include the desired modification in order to correct the mutation.

Those skilled in the art of CF mutations recognise that between 1000 and 2000 mutations are known in the CFTR gene, including R117H, G542X, G551D, R553X, W1282X, and N1303K.

In general, mutations in any target RNA that can be reversed using oligonucleotide constructs according to the invention are G-to-A mutations, in the case of adenosine deaminase recruitment, and U-to-C mutations in the case of cytidine deaminase recruitment, and oligonucleotide constructs can be designed accordingly. Mutations that may be targeted using oligonucleotide constructs according to the invention also include C to A, U to A (T to A on the DNA level) in the case of recruiting adenosine deaminases, and A to C and G to C mutations in the case of recruiting cytidine deaminases. Although RNA editing in the latter circumstances may not necessarily revert the mutation to wild-type, the edited nucleotide may give rise to an improvement over the original mutation. For example, a mutation that causes an in frame stop codon—giving rise to a truncated protein, upon translation—may be changed into a codon coding for an amino acid that may not be the original amino acid in that position, but that gives rise to a (full length) protein with at least some functionality, at least more functionality than the truncated protein.

The target sequence is endogenous to the eukaryotic, preferably mammalian, more preferably human cell. Thus the target sequence is not, for instance, a transgene or a marker gene which has been artificially introduced at some point in the cell's history, but rather is a gene that is naturally present in the cell (whether in mutant or non-mutant form).

The invention is not limited to correcting mutations, as it may instead be useful to change a wild-type sequence into a mutated sequence by applying oligonucleotides according to the invention. One example where it may be advantageous to modify a wild-type adenosine is to bring about skipping of an exon, for example by modifying an adenosine that happens to be a branch site required for splicing of said exon. Another example is where the adenosine defines or is part of a recognition sequence for protein binding, or is involved in secondary structure defining the stability of the RNA. As noted above, therefore, the invention can be used to provide research tools for diseases, to introduce new mutations which are less deleterious than an existing mutation, etc.

The amount of oligonucleotide to be administered, the dosage and the dosing regimen can vary from cell type to cell type, the disease to be treated, the target population, the mode of administration (e.g. systemic versus local), the severity of disease and the acceptable level of side activity, but these can and should be assessed by trial and error during in vitro research, in pre-clinical and clinical trials. The trials are particularly straightforward when the modified sequence leads to an easily-detected phenotypic change. It is possible that higher doses of oligonucleotide could compete for binding to a nucleic acid editing entity (e.g. ADAR) within a cell, thereby depleting the amount of the entity which is free to take part in RNA editing, but routine dosing trials will reveal any such effects for a given oligonucleotide and a given target.

One suitable trial technique involves delivering the oligonucleotide construct to cell lines, or a test organism and then taking biopsy samples at various time points thereafter. The sequence of the target RNA can be assessed in the biopsy sample and the proportion of cells having the modification can easily be followed. After this trial has been performed once then the knowledge can be retained and future delivery can be performed without needing to take biopsy samples.

A method of the invention can thus include a step of identifying the presence of the desired change in the cell's target RNA sequence, thereby verifying that the target RNA sequence has been modified. This step will typically involve sequencing of the relevant part of the target RNA, or a cDNA copy thereof (or a cDNA copy of a splicing product thereof, in case the target RNA is a pre-mRNA), as discussed above, and the sequence change can thus be easily verified. Alternatively the change may be assessed on the level of the protein (length, glycosylation, function or the like), or by some functional read-out, such as a(n) (inducible) current, when the protein encoded by the target RNA sequence is an ion channel, for example. In the case of CFTR function, an Ussing chamber assay or an NPD test in a mammal, including humans, are well known to a person skilled in the art to assess restoration or gain of function.

After RNA editing has occurred in a cell, the modified RNA can become diluted over time, for example due to cell division, limited half-life of the edited RNAs, etc. Thus, in practical therapeutic terms a method of the invention may involve repeated delivery of an oligonucleotide construct until enough target RNAs have been modified to provide a tangible benefit to the patient and/or to maintain the benefits over time.

Oligonucleotides of the invention are particularly suitable for therapeutic use, and so the invention provides a pharmaceutical composition comprising an oligonucleotide of the invention and a pharmaceutically acceptable carrier. In some embodiments of the invention the pharmaceutically acceptable carrier can simply be a saline solution. This can usefully be isotonic or hypotonic, particularly for pulmonary delivery. The invention also provides a delivery device (e.g. syringe, inhaler, nebuliser) which includes a pharmaceutical composition of the invention.

The invention also provides an oligonucleotide of the invention for use in a method for making a change in a target RNA sequence in a mammalian, preferably human cell, as described herein. Similarly, the invention provides the use of an oligonucleotide construct of the invention in the manufacture of a medicament for making a change in a target RNA sequence in a mammalian, preferably human cell, as described herein.

The invention also relates to a method for the deamination of at least one specific target adenosine present in a target RNA sequence in a cell, said method comprising the steps of: providing said cell with an AON according to the invention; allowing uptake by the cell of said AON; allowing annealing of said AON to the target RNA sequence; allowing a mammalian ADAR enzyme comprising a natural dsRNA binding domain as found in the wild type enzyme to deaminate said target adenosine in said target RNA sequence to an inosine; and optionally identifying the presence of said inosine in the RNA sequence. Introduction of the AON according to the present invention into the cell is performed by general methods known to the person skilled in the art. After deamination the read-out of the effect (alteration of the target RNA sequence) can be monitored through different ways. Hence, the identification step of whether the desired deamination of the target adenosine has indeed taken place depends generally on the position of the target adenosine in the target RNA sequence, and the effect that is incurred by the presence of the adenosine (point mutation, early stop codon, aberrant splice site, alternative splice site, misfolding of the resulting protein, etc.). Hence, in a preferred aspect, depending on the ultimate deamination effect of A-to-I conversion, the identification step comprises: sequencing the target RNA; assessing the presence of a functional, elongated, full length and/or wild type protein when said target adenosine is located in a UGA or UAG stop codon, which is edited to a UGG codon through said deamination; assessing the presence of a functional, elongated, full length and/or wild-type protein when two target adenosines are located in a UAA stop codon, which is edited to a UGG codon through the deamination of both target adenosines; assessing whether splicing of the pre-mRNA was altered by said deamination; or using a functional read-out, wherein the target RNA after said deamination encodes a functional, full length, elongated and/or wild type protein. In the event that there is a UAA stop codon it means that both adenosines need to be deaminated. Hence, the invention also relates to oligonucleotides and methods wherein two adenosines that are next to each other are co-deaminated by an RNA editing enzyme such as ADAR. In this particular case, the UAA stop codon is converted into a UGG Trp-encoding codon (see Table 1). Because the deamination of the adenosine to an inosine may result in a protein that is no longer suffering from the mutated A at the target position, the identification of the deamination into inosine may also be a functional read-out, for instance an assessment on whether a functional protein is present, or even the assessment that a disease that is caused by the presence of the adenosine is (partly) reversed. The functional assessment for each of the diseases mentioned herein will generally be according to methods known to the skilled person. When the presence of a target adenosine causes aberrant splicing, the read-out may be the assessment of whether the aberrant splicing is still taking place, or not, or less. On the other hand, when the deamination of a target adenosine is wanted to introduce a splice site, then similar approaches can be used to check whether the required type of splicing is indeed taking place. A very suitable manner to identify the presence of an inosine after deamination of the target adenosine is of course RT-PCR and sequencing, using methods that are well-known to the person skilled in the art.

The present invention relates to an antisense oligonucleotide (AON) capable of forming a double stranded complex with a target RNA sequence in a cell, preferably a human cell, for the deamination of a target adenosine in the target RNA sequence by an ADAR enzyme present in the cell, said AON comprising a Central Triplet of 3 sequential nucleotides, wherein the nucleotide directly opposite the target adenosine is the middle nucleotide of the Central Triplet, wherein 1, 2 or 3 nucleotides in said Central Triplet comprise a sugar modification and/or a base modification; with the proviso that the middle nucleotide does not have a 2'-O-methyl modification. The sugar and/or base modification of the nucleotides of the present invention render the AON more stable and/or cause an improved induction of deamination of the target adenosine as compared to AONs not carrying the sugar and/or base modification. In a preferred embodiment, the non-complementary nucleotide that is directly opposite the target adenosine when the double stranded complex is formed, is a cytidine. This cytidine, together with the nucleotides that are directly 5' and 3' of it in the AON together form the Central Triplet as defined herein. Although there may be additional mismatches between the AON and the target RNA sequence outside the Central Triplet, the cytidine in the centre of the Central Triplet forms at least one mismatch with the target adenosine in the target sequence such that it can be edited by the ADAR present in the cell. The cell is preferably a human cell and the ADAR is preferably a human ADAR, more preferably an endogenous ADAR in said cell without the need to overexpress it by recombinant means. In any event, the middle nucleotide in the Central Triplet does not have a 2'-O-methyl modification, allowing the cellular RNA editing enzyme(s) to act. In one embodiment, 1 or 2 nucleotides in the Central Triplet other than the middle nucleotide are replaced by an inosine. This may be preferred to allow a better fit with the ADAR enzyme. In yet another preferred embodiment, the AON does not comprise a portion that is capable of forming an intramolecular stem-loop structure that is capable of binding a mammalian ADAR enzyme.

As exemplified in FIGS. 1, 2A-D and 4A-B, the Central Triplet is depicted as YXZ or as XXY. Different base modifications are provided. The skilled person understands that these base modifications are to a certain level dependent on the nucleotides opposite the nucleotides in the Central Triplet. Hence, in the example of YXZ, wherein X is the middle nucleotide opposite the target adenosine, the X may be cytidine, 5-methylcytidine, 5-hydroxymethylcytidine, uridine, or pyrrolocytidine, whereas the Y and/or Z may be inosine, 5-methylcytidine, pyrrolocytidine, pseudouridine, 4-thiouridine, thienouridine, 2-aminopurine, 2,6-diaminopurine, thienoguanosine, 5-methoxyuridine, dihydrouridine, 5-hydroxymethylcytidine, 5-methyluridine, 8-aza-7-deazaguanosine, 7-aminomethyl-7-deazaguanosine, 7-methyladenosine, 8-methyladenosine, 3-deazaadenosine, 7-deazaadenosine, 8-azidoadenosine, etc., depending on the nucleotides opposite the Central Triplet; hence depending on the target RNA sequence and disease related to that. Ergo, in a preferred embodiment, said base modification is selected from the group consisting of 2-aminopurine, 2,6-diaminopurine, 3-deazaadenosine, 7-deazaadenosine, 7-methyladenosine, 8-azidoadenosine, 8-methyladenosine, 5-hydroxymethylcytidine, 5-methylcytidine, Pyrrolocytidine, 7-aminomethyl-7-deazaguanosine, 7-deazaguanosine, 7-methylguanosine, 8-aza-7-deazaguanosine, thienoguanosine, inosine, 4-thio-uridine, 5-methoxyuridine, 5-methyluridine, dihydrouridine, pseudouridine, and thienouridine.

In another preferred embodiment, the sugar modification is selected from the group consisting of deoxyribose (i.e. DNA), Unlocked Nucleic Acid (UNA) and 2'-fluororibose. In a particularly preferred aspect, the present invention relates to an AON comprising a Central Triplet of 3 sequential nucleotides, wherein the nucleotide directly opposite the target adenosine is the middle nucleotide of the Central Triplet, and wherein 1, and preferably 2, and even more preferably all 3 nucleotides in said Central Triplet are DNA nucleotides to render the AON more stable and/or more effective in inducing deamination of the target adenosine. In another preferred aspect, the remainder of the AON consists of RNA nucleotides that preferably (but not necessarily) are 2'-O-methyl modified. Other stabilizing modifications may be used outside the Central Triplet. Other ribose modifications that are quite compatible with targeted editing in accordance with the invention are 2'-O-methoxyethyl (2'-O-MOE), LNA, 2'-F and 2'-NH$_2$. Different combinations of sugar modifications (as listed herein) of the nucleotides outside the Central triplet may be applied. In another preferred aspect, the AON according to the invention comprises at least one internucleoside linkage modification selected from the group consisting of phosphorothioate, 3'-methylenephosphonate (i.e. 3'-O-methylphosphonate internucleotide linkage), 5'-methylenephosphonate (i.e. 5'-O-methylphosphonate internucleotide linkage), 3'-phosphoroamidate (i.e. N-3'-phosphoroamidate internucleotide linkage) and 2'-5'-phosphodiester (i.e. 2'-5'-phosphodiester internucleotide linkage). Especially preferred are phosphorothioate linkages. Further preferred AONs according to the invention are AONs wherein the 2, 3, 4, 5, or 6 terminal nucleotides of the 5' and 3' terminus of the AON are linked with phosphorothioate linkages, preferably wherein the terminal 5 nucleotides at the 5' and 3' terminus are linked with phosphorothioate linkages. As disclosed herein, also the nucleotides within the Central Triplet may be connected through phosphorothioate linkages, although it appears that there is preferably more than one such linkage present in the Central Triplet to render the AON stable as well as active in RNA editing. In a further preferred aspect, the AON is annealed to a protecting sense oligonucleotide (SON) for increased stability and, this is hypothesized, prolonged activity due to the more stable character of the double stranded antisense oligonucleotide+SON complex. The SON does not necessarily have to be the same length as the antisense oligonucleotide. It may be longer, the same length or shorter.

In one preferred aspect, all nucleotides in the AON outside the Central Triplet comprise a 2'-O-alkyl group such as a 2'-O-methyl group, or a 2'-O-methoxyethyl group. Nucleotides outside the Central triplet may also be DNA as long as a DNA stretch does not result in a gapmer. Also, the AON is preferably longer than 10, 11, 12, 13, 14, 15, 16 or 17 nucleotides, and preferably shorter than 100 nucleotides, more preferably shorter than 60 nucleotides. In yet another preferred embodiment, the AON comprises 18 to 70 nucleotides, more preferably comprises 18 to 60 nucleotides, and even more preferably comprises 18 to 50 nucleotides. The invention also relates to a pharmaceutical composition comprising the AON according to any one of claims 1 to 12, and a pharmaceutically acceptable carrier.

The oligonucleotide according to the invention is suitably administrated in aqueous solution, e.g. saline, or in suspension, optionally comprising additives, excipients and other ingredients, compatible with pharmaceutical use, at concentrations ranging from 1 ng/ml to 1 g/ml, preferably from 10 ng/ml to 500 mg/ml, more preferably from 100 ng/ml to 100 mg/ml. Dosage may suitably range from between about 1 µg/kg to about 100 mg/kg, preferably from about 10 µg/kg to about 10 mg/kg, more preferably from about 100 µg/kg to about 1 mg/kg. Administration may be by inhalation (e.g. through nebulization), intranasally, orally, by injection or infusion, intravenously, subcutaneously, intra-dermally, intra-cranially, intramuscularly, intra-tracheally, intra-peritoneally, intra-rectally, by direct injection into a tumor, and the like. Administration may be in solid form, in the form of a powder, a pill, or in any other form compatible with pharmaceutical use in humans.

The invention is particularly suitable for treating genetic diseases, such as cystic fibrosis, albinism, alpha-1-antitrypsin (A1AT) deficiency, Alzheimer disease, Amyotrophic lateral sclerosis, Asthma, ß-thalassemia, Cadasil syndrome, Charcot-Marie-Tooth disease, Chronic Obstructive Pulmonary Disease (COPD), Distal Spinal Muscular Atrophy (DSMA), Duchenne/Becker muscular dystrophy, Dystrophic Epidermolysis bullosa, Epidermolysis bullosa, Fabry disease, Factor V Leiden associated disorders, Familial Adenomatous Polyposis, Galactosemia, Gaucher's Disease, Glucose-6-phosphate dehydrogenase deficiency, Haemophilia, Hereditary Hemachromatosis, Hunter Syndrome, Huntington's disease, Hurler Syndrome, Inflammatory Bowel Disease (IBD), Inherited polyagglutination syndrome, Leber congenital amaurosis, Lesch-Nyhan syndrome, Lynch syndrome, Marfan syndrome, Mucopolysaccharidosis, Muscular Dystrophy, Myotonic dystrophy types I and II, neurofibromatosis, Niemann-Pick disease type A, B and C, NY-eso1 related cancer, Parkinson's disease, Peutz-Jeghers Syndrome, Phenylketonuria, Pompe's disease, Primary Ciliary Disease, Prothrombin mutation related disorders, such as the Prothrombin G20210A mutation, Pulmonary Hypertension, Retinitis Pigmentosa, Sandhoff Disease, Severe Combined Immune Deficiency Syndrome (SCID), Sickle Cell Anemia, Spinal Muscular Atrophy, Stargardt's Disease, Tay-Sachs Disease, Usher syndrome, X-linked immunodeficiency, Sturge-Weber Syndrome, various forms of cancer (e.g. BRCA1 and 2 linked breast cancer and ovarian cancer), and the like.

In some embodiments the oligonucleotide construct can be delivered systemically, but it is more typical to deliver an oligonucleotide to cells in which the target sequence's phenotype is seen. For instance, mutations in CFTR cause cystic fibrosis which is primarily seen in lung epithelial tissue, so with a CFTR target sequence it is preferred to deliver the oligonucleotide construct specifically and directly to the lungs. This can be conveniently achieved by inhalation e.g. of a powder or aerosol, typically via the use of a nebuliser. Especially preferred are nebulizers that use a so-called vibrating mesh, including the PARI eFlow (Rapid) or the i-neb from Respironics. The inventors have found that inhaled use of oligonucleotide constructs can lead to systemic distribution of the oligonucleotide construct and uptake by cells in the gut, liver, pancreas, kidney and salivary gland tissues, among others. It is therefore to be expected that inhaled delivery of oligonucleotide constructs according to the invention can also target these cells efficiently, which in the case of CFTR gene targeting could lead to amelioration of gastrointestinal symptoms also associated with cystic fibrosis. For other target sequences, depending on the disease and/or the target organ, administration may be topical (e.g. on the skin), intradermal, subcutaneous, intramuscular, intravenous, oral, ocular injection, etc.

In some diseases the mucus layer shows an increased thickness, leading to a decreased absorption of medicines via the lung. One such a disease is chronical bronchitis, another example is cystic fibrosis. Various forms of mucus normalizers are available, such as DNAses, hypertonic saline or mannitol, which is commercially available under the name of Bronchitol. When mucus normalizers are used in combination with RNA editing oligonucleotide constructs, such as the oligonucleotide constructs according to the invention, they might increase the effectiveness of those medicines. Accordingly, administration of an oligonucleotide construct according to the invention to a subject, preferably a human subject is preferably combined with mucus normalizers, preferably those mucus normalizers described herein. In addition, administration of the oligonucleotide constructs according to the invention can be combined with administration of small molecule for treatment of CF, such as potentiator compounds for example Kalydeco (ivacaftor; VX-770), or corrector compounds, for example VX-809 (lumacaftor) and/or VX-661. Other combination therapies in CF may comprise the use of an oligonucleotide construct according to the invention in combination with an inducer of adenosine deaminase, using IFN-gamma or TNF-alpha.

Alternatively, or in combination with the mucus normalizers, delivery in mucus penetrating particles or nanoparticles can be applied for efficient delivery of RNA editing molecules to epithelial cells of for example lung and intestine. Accordingly, administration of an oligonucleotide construct according to the invention to a subject, preferably a human subject, preferably uses delivery in mucus penetrating particles or nanoparticles.

Chronic and acute lung infections are often present in patients with diseases such as cystic fibrosis. Antibiotic treatments reduce bacterial infections and the symptoms of those such as mucus thickening and/or biofilm formation. The use of antibiotics in combination with oligonucleotide constructs according to the invention could increase effectiveness of the RNA editing due to easier access of the target cells for the oligonucleotide construct. Accordingly, administration of an oligonucleotide construct according to the invention to a subject, preferably a human subject, is preferably combined with antibiotic treatment to reduce bacterial infections and the symptoms of those such as mucus thickening and/or biofilm formation. The antibiotics can be administered systemically or locally or both.

For application in for example cystic fibrosis patients the oligonucleotide constructs according to the invention, or packaged or complexed oligonucleotide constructs according to the invention may be combined with any mucus normalizer such as a DNase, mannitol, hypertonic saline and/or antibiotics and/or a small molecule for treatment of CF, such as potentiator compounds for example ivacaftor, or corrector compounds, for example lumacaftor and/or VX-661.

To increase access to the target cells, Broncheo-Alveolar Lavage (BAL) could be applied to clean the lungs before administration of the oligonucleotide according to the invention.

The inventors of the present invention have shown herein that certain modifications to AONs targeting RNA and recruiting ADAR enzymes yield in increased stability and through this, better applicability in in vivo settings. However, stability is one thing. In addition to stabilizing the AONs by preventing nuclease-mediated degradation, the modified nucleotides are ideally selected so that they support and preferably improve binding and/or catalytic activity of the ADAR enzymes. The known structural features of the interaction between the ADAR2 deaminase domain and a dsRNA substrate (provided in great detail in Matthews et al. 2016. Nat Struct Mol Biol 23:426-433) can be used to rationally select modified AONs that best fit into the catalytic center of the ADAR2 enzyme. From the (colored) structure disclosed in Matthews et al. (2016) it can be seen that ADAR2 contacts the editing site from the minor groove of the dsRNA helix; FIG. 2 therein, Panel A: View of the structure of the complex perpendicular to the dsRNA helical axis. The pink RNA strand is the edited strand, and the blue strand is the complementary strand. The flipped-out target base (N) is shown in red. The protein makes contacts with the helix through its minor groove. Panel B: View of structure along the dsRNA helical axis. Panel C: Summary of the contacts between ADAR2 E488Q deaminase domain and RNA duplex. Red color indicates the edited target strand, and blue color the complementary strand (equivalent to the AONs presented here). Dashed lines indicate interactions of the amino acid side chains (amino acid identity and position indicated) of the deaminase domain with the RNA strands. FIG. 5A of Matthews et al. (2016) shows in detail a space-filling model of the interaction of the nucleotide 5' to the edited site (on the target strand) and the complementary nucleotide on the other strand. In the upper panel, the 5' nucleotide is a uridine, and the interaction to the opposing adenosine is stabilized by the glycine 489 of the ADAR2 deaminase domain. The lower panel shows the modelled interaction of a C (5' to the edited nucleotide) with a complementary G. In this case, interaction with the glycine results in a clash with the 2-amino group, which reduces editing efficiency. Replacement of the guanosine base on the opposing strand (or AON) with an inosine would resolve this steric clash.

For base modifications, the inventors of the present invention deduced that chemical modifications that are projected into the major groove of the helix (Sharma and Watts 2015, Future Med. Chem. 7(16), 2221-2242) would interfere with the function of ADAR2 the least. See FIGS. 2A-2D and examples below for details of the different AONs. For pyrimidine nucleotides, such modifications include substituents at position 4 or 5 of the base, including 4-thiouridine (see e.g. ADAR60-13), 5-methyluridine (see e.g. ADAR60-14), 5-methoxyuridine (see e.g. ADAR60-26), 5-methylcytidine (see e.g. ADAR60-9, -11 through 16, -20, 26, -27 and -29 through -32 and ADAR68-1 through -6) and 5-hydroxymethylcytidine (see e.g. ADAR60-28). For purine nucleotides, substituents in the positions 7 and 8 of the base would similarly be directed into the major groove, including 7-methylguanosine, 7-deazaguanosine, 8-aza-7-deazaguanosine, 7-aminomethyl-7-deazaguanosine, 7-methyladenosine, 8-methyladenosine, 3-deazaadenosine, 7-deazaadenosine, or 8-azidoadenosine (see ADAR60-29, -30, -31, and -32, and ADAR68-1, -2, -3, -4 and -5, respectively).

For modifications of the backbone (i.e. modifications of the ribosyl moiety of the nucleotides or the internucleotide linkages) of the AON, the inventors of the present invention deduced that modifications that do not change the A form structure of the RNA helix would only modestly interfere with the function of ADAR2. The structural information of the ADAR2 deaminase domain also suggests that in certain positions it is important to retain chemical groups that are contacted by amino acid side chains of the enzyme, such as phosphate groups and 2'-hydroxyl groups. Modifications that permit the retention of these features include UNA (see e.g. ADAR60-8 and -9), 3'-methylenephosphonate, 5'-methylenephosphonate, 3'-phosphoroamidate, or 2'-5' phosphodiester modifications (see ADAR60-22, -23, -24 and -25, respectively). In some cases, a direct interaction by ADAR2 is not present for a given substituent on a specific nucleotide. In such cases, other chemical groups can be used that protect the AON from nucleases, but are small enough not to cause steric interference with ADAR2, e.g. a 2'-fluoro modification or 2'-H (deoxy) as it is not larger than the naturally occurring hydroxyl group (see e.g. ADAR60-7).

Modified nucleotides can be selected not only to provide enhanced protection from nucleases and minimal interference to ADAR2 binding, but also to specifically increase functionality of ADAR2. Specific nucleotide modifications may in particular be necessary to enhance the editing activity on substrate RNAs where the target sequence is not optimal for ADAR editing. Previous work has established that certain sequence contexts are more amenable to editing. For example, the target sequence 5'-UAG-3' (with the target A in the middle) contains the most preferred nearest-neighbor nucleotides for ADAR2, whereas a 5'-CAA-3' target sequence is disfavored (Schneider et al. 2014). The structural analysis of ADAR2 deaminase domain hints at the possibility of enhancing editing by careful selection of the nucleotides that are opposite to the target trinucleotide (Matthews et al. 2016). For example, the 5'-CAA-3' target sequence, paired to a 3'-GCU-5' sequence on the opposing strand (with the A-C mismatch formed in the middle), is disfavored because the amino group of the guanosine base sterically clashes with an amino acid side chain of ADAR2. However, it is postulated that a smaller nucleobase lacking the amino group, such as inosine, could fit better into this position without causing steric clashes, while still retaining the base-pairing potential to the opposing cytosine (see e.g. ADAR60-10 through -19, and -26, -27, -28 and -32). An inosine could also be used within a different sequence context. For example, a target sequence 5'-UAG-3' could be paired with the AON Central Triplet sequence 5'-CCI-3', thus forming a U-I wobble base pair that can provide increased flexibility that is needed for the target adenosine to flip out of the helix into the active site of the enzyme (see e.g. ADAR68-6).

Backbone modifications can also have additional benefits beyond nuclease protection, such as providing increased flexibility for the nucleotides surrounding the edited site, which has been suggested as an important factor for correctly positioning the substrate in the active site of the enzyme. UNA is one such backbone modification, as the open structure of the sugar moiety allows increased movement (see ADAR60-8 and -9). Conversely, modifications that could enhance activity of suboptimal sequences also include the use of backbone modifications that force it into a conformation that favors editing.

EXAMPLES

Example 1. Chemical Modifications in AONs Targeting Human SERPINA1 RNA to Increase Stability Unpublished patent application PCT/EP2017/065467 describes a method for targeted A-to-I editing by the use of antisense oligonucleotides (AONs). Whereas most of the nucleotides in these AONs are 2'-O-methylated RNA and have phosphorothioate linkages, they contain a few, usually 3, unmodified RNA nucleotides (the 'Central Triplet') in the portion of the AON with the middle nucleotide directly opposed to the target adenosine and its 2 neighbouring nucleotides. This is because it had previously been shown that A-to-I editing is strongly inhibited when the nucleotides of the Central Triplet are 2'-O-methylated (Vogel et al. 2014). However, AONs containing unmodified RNA nucleotides are inherently biologically unstable due to nucleases that can hydrolyze the residues in these positions. This may be a disadvantage for efficient use of the AONs as e.g. therapeutic agents, as they may be degraded prior to reaching their targets.

The inventors of the present invention investigated the stability of the AONs with unmodified RNA nucleotides at the Central Triplet, and whether the stability of such AONs could be increased by using chemical modifications other than 2'-O-methylation.

Figure 3B:
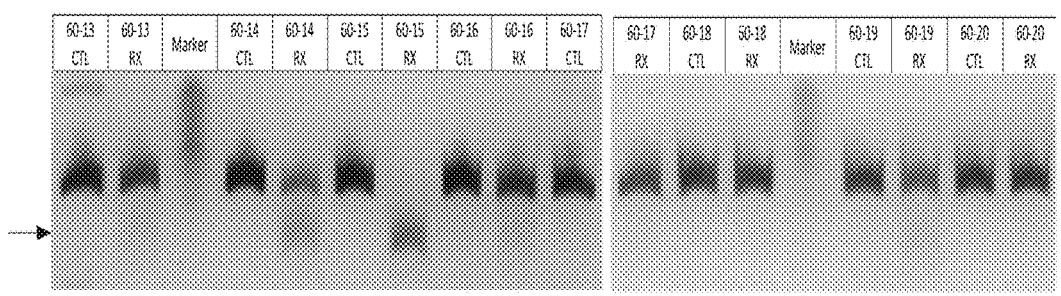
Figure 3C:
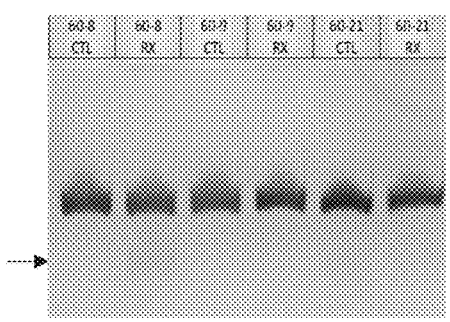

First, as a non-limiting example, the target that was selected for RNA editing was the c.1096G>A mutation in the SERPINA1 RNA, which is the cause of A1AT-deficiency (A1ATD). A1ATD is an example of a disease target for RNA editing using the approach as outlined herein. In FIG. 1A and FIG. 1B, the complementarity of exemplary AONs to the SERPINA1 target is illustrated schematically. The ADAR60-1 complementarity to the target sequence is shown in FIG. 1A, whereas the Central Triplet in the ADAR60 series (5'-YXZ-3') is indicated as such in FIG. 1B. A number of AONs targeting the mutant RNA with varying modifications in the backbone as well as in the bases of the nucleotides of the Central Triplet were tested for stability by incubating them in cell culture medium (MEM) containing 15% Fetal Bovine Serum (FBS) at +37° C. for 30 min (RX). As negative controls, AONs were incubated in Phosphate Buffered Saline (PBS; CTL). The samples were then resolved in denaturing polyacrylamide gels (15% PAGE gel with 8 M urea), which were subsequently stained with toluidine blue to visualize the AONs and fragments thereof. The AONs with their respective sequences and their modifications are indicated in FIGS. 2A-2D. FIGS. 3A-3C show the results of the stability assays using the AONs of the ADAR60 series. ADAR60-1, containing an unmodified 5'-UCG-3' RNA Central Triplet, is efficiently cleaved (~degraded) within 30 min in the presence of FBS (to approximately 50%). Some degradation is even apparent when the AON is incubated in control buffer. The rate of degradation is not reduced when the location of the three RNA nucleotides is shifted (ADAR60-3). Importantly, lowering the number of unmodified RNA nucleotides to 2 (instead of 3) results in a reduction in degradation (ADAR60-2). A fully 2'-O-methylated AON, which here serves as a negative control, remains stable under these conditions (ADAR60-4), as does an AON where the Central Triplet has been changed to DNA nucleotides (ADAR60-6). This shows at least that when the Central Triplet is not 2'-O-methylated, the AON is prone to degradation and that such can be resolved by adding at least one 2'-O-methylated nucleotide to the Central Triplet, or amending the entire Central Triplet to DNA nucleotides. Another modification of the sugar, replacement of RNA by unlocked nucleic acid (UNA) in 2 of the 3 positions of the Central Triplet also results in increased stability (ADAR60-8), and even more so when combined with the base modification 5-methylcytosine in the middle of the triplet (ADAR60-9). Inclusion of one phosphorothioate linkage after the first position of the Central Triplet (5'-U*CG-3' in which the asterisk represents the phosphorothioate linkage) does not increase stability appreciably (ADAR60-5). See example 2 below for further experiments towards increasing numbers of phosphorothioate linkages.

Replacement of guanosine with inosine also results in noticeable reduction in degradation (ADAR60-10). When this modification is combined with the replacement of cytidine for 5-methylcytidine (ADAR60-11), stability remains and is further increased when both modifications are combined with the replacement of uridine for pseudouridine (ADAR60-12).

Replacing all 3 nucleotides of the Central Triplet with modified nucleotides appeared to yield the greatest effect on stability. The exact modifications in each position can be varied, and this greatly affects the stability of the AON. In AONs otherwise similar to ADAR60-12, replacement of the pseudouridine with 4-thiouridine (ADAR60-13) or 2,6-diaminopurine (ADAR60-16) results in AONs of comparable stability, while 5-methyluridine (ADAR60-14) in contrast reduces stability, and thienouridine (ADAR60-15) causes almost complete degradation of the AON, even more so than with the unmodified RNA triplet.

Replacement of the middle C in the Central Triplet with pyrrolocytidine results in an even more significant stabilization than with 5-methylcytidine: AONs with pyrrolocytidine and inosine are nearly fully stable under these conditions regardless of whether they contain a pseudouridine or unmodified uridine in the first position of the triplet (ADAR60-18 and ADAR60-17, respectively). Replacement of the uridine with thienouridine (ADAR60-19) again results in reduced stability also in this context, but not to the same extent as with ADAR60-15.

Similar to the other two positions of the Central Triplet, the last position can also be modified with different base modifications to achieve stabilization. Here, instead of inosine, thienoguanosine was used in combination with pseudouridine and either 5-methylcytidine or pyrrolocytidine (ADAR60-20 and ADAR60-21, respectively). Both AONs are fully stable under these conditions; the increased stability with thienoguanosine is noticeable when comparing with the otherwise similar ADAR60-12 and ADAR60-20.

It is envisioned that additional combinations to achieve a similar effect for increased stabilization are replacement of e.g. guanosine by 7-methylguanosine, 7-deazaguanosine, 8-aza-7-deazaguanosine, or 7-aminomethyl-7-deazaguanosine (see ADAR60-29, -30, -31 and -32, respectively), or that of cytidine by 5-hydroxymethylcytosine (see ADAR60-28), or that of uridine with 5-methoxyuridine or dihydrouridine (see ADAR60-26 and -27, respectively). Stabilization was also achieved by sugar and backbone modifications of the Central Triplet, including 2'-fluoro, 3'-methylenephosphonate, 5'-methylenephosphonate, 3'-phosphoroamidate, or 2'-5' phosphodiester modifications (2' to 5' backbone linkages; see ADAR60-7, -22, -23, -24 and -25, respectively).

The results shown in this example indicate that not every modification is useful for reducing degradation of RNA-editing antisense oligonucleotides but many modifications do add to the stability, and that the modifications in and possibly around the Central Triplet should be carefully selected. Modifying the nucleotides in the Central Triplet with specified chemistries surely increases the stability of the oligonucleotide. All in all, the results presented in this example show that (combinations of) modifications of the nucleotides in the Central Triplet can improve stability, and that modification of several bases at once results in incremental stabilization.

Example 2. Phosphorothioate Linkages in AONs Targeting Mouse Ldua RNA to Increase Stability In the previous example it was shown that inclusion of one phosphorothioate linkage after the first position within the Central Triplet did not increase stability appreciably (FIG. 3A; ADAR60-5). To investigate this in more depth, it was tested whether inclusion of more phosphorothioate linkages within the Central Triplet region could nevertheless have an influence and increase stability.

Figure 5:
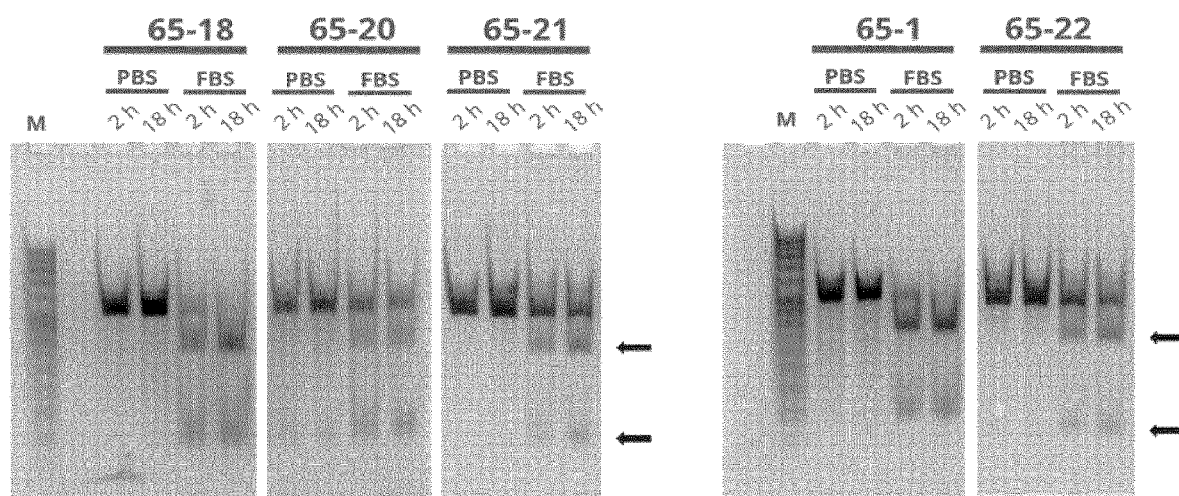
FIG. 5 shows the stability of the oligonucleotides ADAR65-1, -18, -20, -21, and -22 directed against the mutated mouse Idua gene (Hurler model), assayed by denaturing gel electrophoresis after incubation in FBS-containing medium. Controls were incubated in PBS. The arrows point at degradation products. The upper bands are full-length AONs. The Marker lanes (M) contain Low Molecular Weight Marker, 10-100 nt (Affymetrix), with 14 oligonucleotide fragments at 5 nt (10 nt −50 nt) and 10 nt (50 nt-100 nt) increments. AON susceptibility to degradation over two different time incubations (2 h and 18 h) is indicated by the ratio of the bands, with a higher prevalence of the lower product suggesting reduced stability.

For this, the inventors of the present invention selected Hurler syndrome as the model system, also known as mucopolysaccharidosis type I-Hurler (MPS I-H), which in humans is caused by the c.1205G>A (W402X) mutation of the IDUA gene. The target sequence in the mutated human gene would be 5'-UAG-3' (with the target A in the middle, see FIG. 4A), and the Central Triplet of the AON would then be 5'-CCA-3' (including the central, mismatched C; see FIG. 4B for the 5'-XXY-3' notation) or 5'-CUA-3'. A mouse model for this mutation also exists (W392X), wherein the Idua gene is mutated. The Hurler mouse model was also used for additional in vivo experiments (see below). Oligonucleotides having the serial number ADAR65 (see FIGS. 2A-2D) were designed to target the mutated mouse Idua gene. ADAR65-1, ADAR65-18, ADAR65-20, ADAR65-21 and ADAR65-22 were tested to see whether additional phosphorothioate linkages would add to the stability of the oligonucleotide. Surprisingly, inclusion of 3 or more phosphorothioates in the Central Triplet region did give a stability increase of the AON (FIG. 5). ADAR65-1 has no additional phosphorothioate linkages in the Central Triplet region and is clearly degraded, whereas ADAR65-22 has 6 phosphorothioate linkages in and around the Central Triplet region and is clearly more stable, even after incubation of 18 h in FBS. Similarly the stability of ADAR65-20 and ADAR65-21 that respectively have 5 and 3 phosphorothioate linkages in the Central Triplet region, was increased when compared to ADAR65-18 that (like ADAR65-1) has no additional phosphorothioates in the Central Triplet region, except for the terminal linkages of the oligonucleotide.

Figure 6:
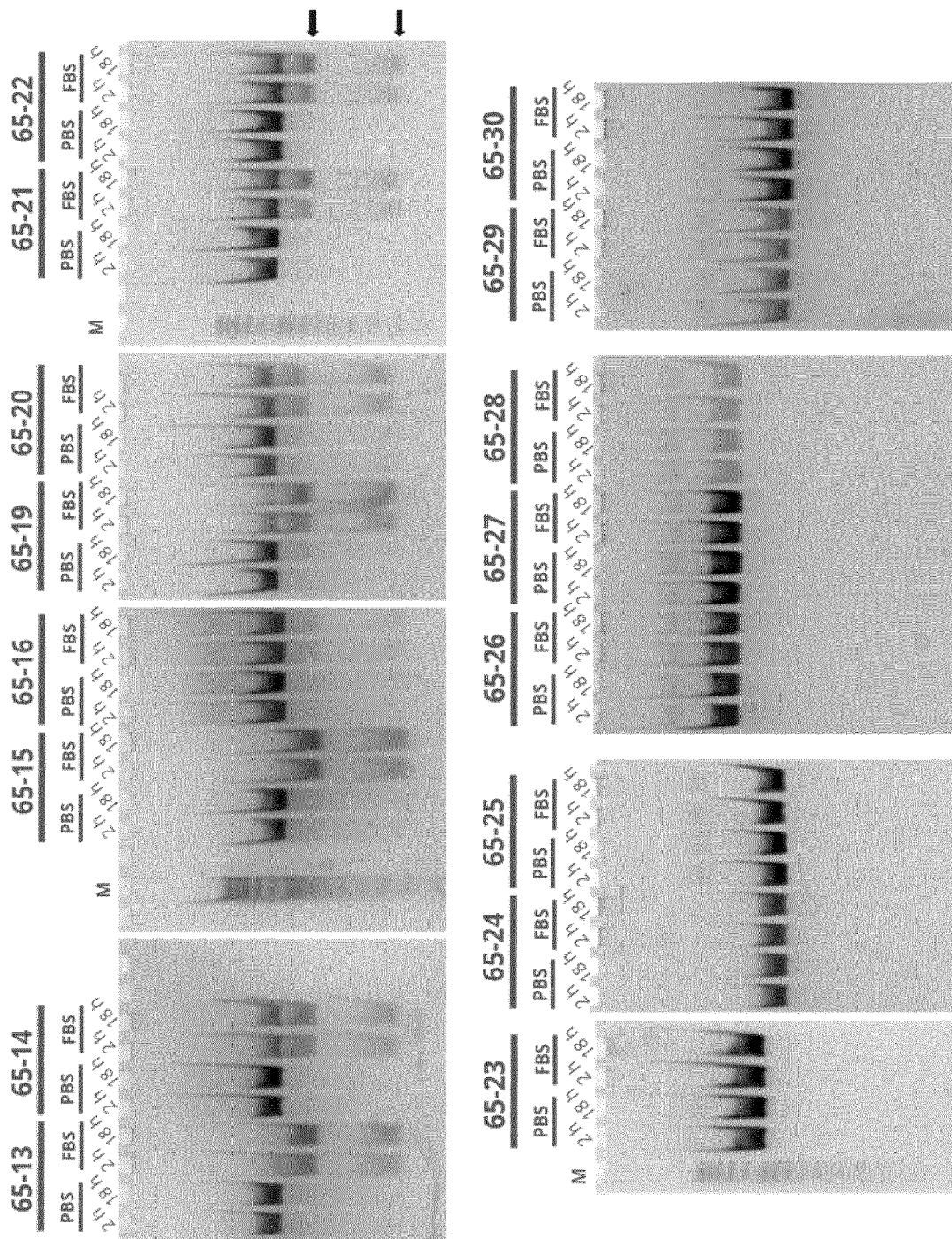
FIG. 6 shows the stability of the additional ADAR65 oligonucleotides, assayed by denaturing gel electrophoresis after incubation for 2 h or 18 h in PBS or FBS, similar to FIG. 5.

Base modifications such as 5-methylcytidine and deoxy 2-aminopurine together with ribose modification such deoxyribose (DNA), 2'-O-methyl, 2'-fluoro and a phosphate backbone (phosphorothioate linkages) were combined. ADAR65-13, -14, -15, -16, -19, -20, -21, -22, -23, -24, -25, -26, -27, -28, -29, and -30 (FIGS. 2A-2D) were tested for stability using the same assay as described above. The results that are depicted in FIG. 6 show that a variety of combinations can be used to obtain stability, even after 18 h incubation in FBS.

Figure 7:
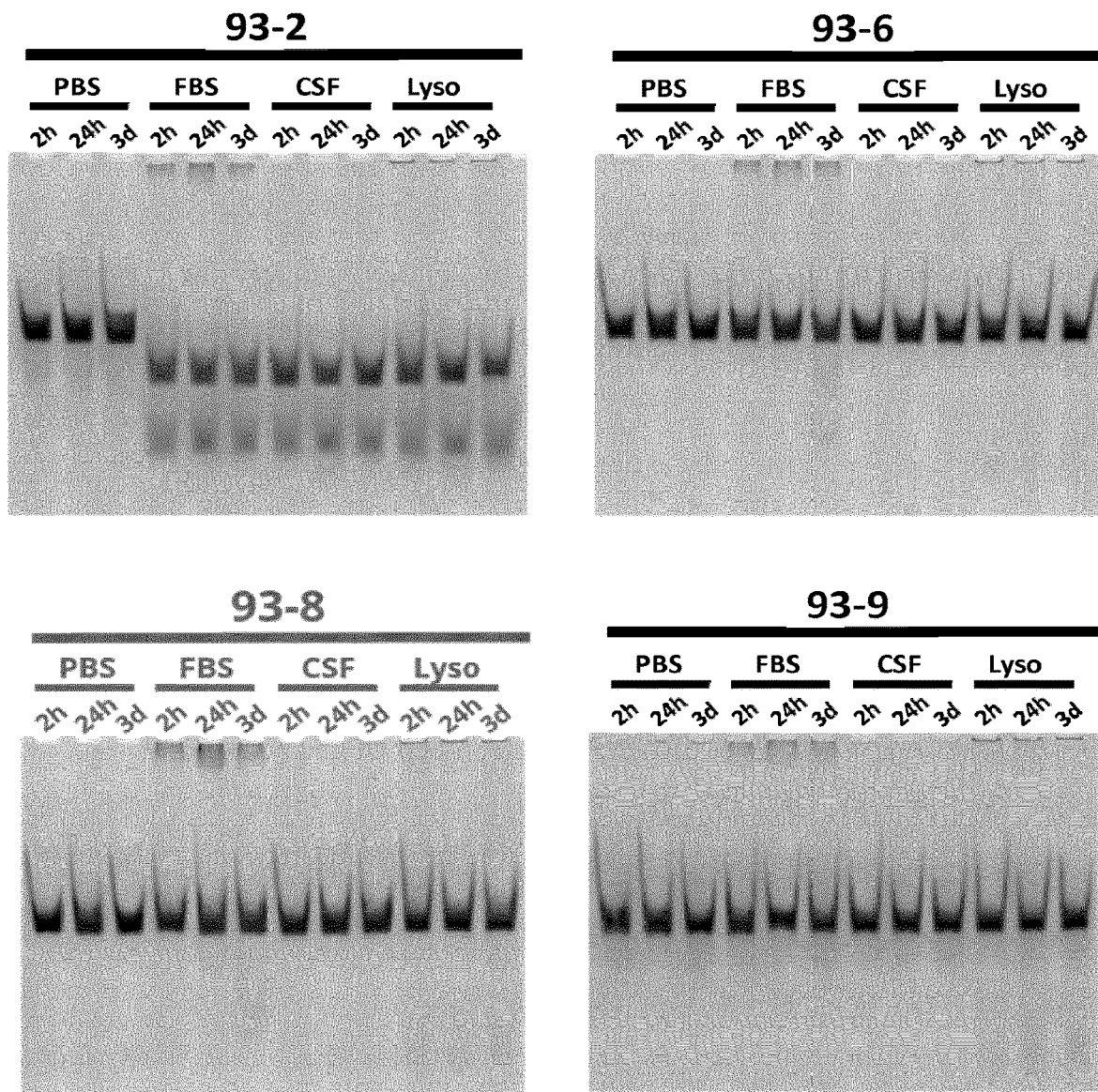
FIG. 7 shows the stability of four ADAR93 oligonucleotides, of which ADAR93-2 contains unmodified RNA in the Central Triplet, while the other three (ADAR93-6, -8, and -9) have two or three DNA nucleotides in the Central Triplet instead. The difference of the additional modifications is as shown in FIGS. 2A-D. The stability was assayed by denaturing gel electrophoresis after incubation for 2 h, 24 h or 3 days in PBS, DMEM+15% FBS, Single Donor Human Cerebrospinal Fluid (CSF) and Mixed Gender Human Liver Lysosomes (Lyso).

Further to this, AONs with either RNA (ADAR93-2) or DNA (ADAR93-6, ADAR93-8, ADAR93-9) in the Central Triplet and varying numbers of phosphorothioate nucleotides (28 in ADAR93-2, 8 in ADAR93-6, 21 in ADAR93-8, 22 in ADAR93-9) were analyzed for stability in various biological solutions. PBS was used as a negative control. To mimic the physiological conditions that the AONs may be subjected to in blood and the central nervous system, the AONs were, respectively, incubated in cell culture medium (DMEM) containing 15% FBS or Single Donor Human Cerebrospinal Fluid (CSF). In order to assess whether the acidic microenvironment of a lysosome and nucleases therein would affect AON stability, oligonucleotides were also incubated in Mixed Gender Human Liver Lysosomes (Lyso). 200 pmol of AON was incubated in each condition for 2 h, 24 h or 3 days, after which the samples were resolved in denaturing polyacrylamide gels (12% PAGE gel with 8 M urea). The gels were stained with toluidine blue solution and destained in water to visualize the AONs and fragments thereof. The results are shown in FIG. 7 and indicate (again) that oligonucleotides that contain RNA without modifications in the Central Triplet (ADAR93-2) are very prone to degradation in FBS, CSF and Lyso because almost all of the oligonucleotides are rapidly digested under these different circumstances, whereas they remain relatively stable in PBS alone. However, changing the Central Triplet to include two or three DNA nucleotides significantly increases the stability of the oligonucleotide in the three different environments, even up to three days.

Antisense oligonucleotides ADAR68, ADAR68-1, -2, -3, -4, and -5 (see FIGS. 2A-2D) potentially targeting the c.1205G>A (W402X) mutation of the human IDUA gene were also designed. The modified Central Triplet can be composed of e.g. two 5-methylcytidines in combination with a nucleotide replacing the adenosine, such as 7-methyladenosine, 8-methyladenosine, 3-deazaadenosine, 7-deazaadenosine, or 8-azidoadenosine (ADAR68-1, -2, -3, -4 and -5 in FIGS. 2A-2D). However, the adenosine can also be replaced by a modified base that can form a wobble base pair with the opposing uridine, such as inosine (ADAR68-6). These AONs are tested for stability as well as for their ability to edit RNA of a target sequence.

Example 3. RNA Editing Activity of AONs with Combined Chemical Base Modifications in the Central Triplet Nucleotide phosphodiester, sugar and base modifications are used to increase the stability of oligonucleotides against nucleases. Importantly, it was envisioned by the inventors of the present invention that such chemical nucleotide modifications may also be used for other purposes such as increased binding of AONs to their target RNA, to get better recognition and/or to increase the enzymatic activity of proteins acting on double-stranded complexes of AONs with their specific target RNA sequences.

The inventors first wanted to know whether a combination of nucleotide base chemical modifications in the Central Triplet of an AON could enhance the editing activity of ADAR2. For this, ADAR60-1 and ADAR60-15 (see FIGS. 2A-2D and 3A-3C) were used to investigate such influence on enhancing editing activity of ADAR2 enzyme on a human mutated SERPINA1 target RNA molecule. These two AONs share the same sequence and length, and both have the chemical phosphorothioate modifications of phosphate groups as well as 2'-O-methyl modifications of ribose sugars outside the Central Triplet. Nucleotides in the Central Triplet of ADAR60-1 are unmodified, whereas the nucleotide bases in the Central Triplet of ADAR60-15 are chemically modified as depicted in FIGS. 2A-2D. The 5-methylcytidine is opposite the target adenosine for editing. Both ADAR60-1 and ADAR60-15 were tested in an in vitro editing assay using HEK293 cell lysates with overexpressed isoform 2 of ADAR2 (ADAR2a), and SERPINA1 target RNA carrying the c.1096G>A mutation. ADAR60-15 without cell lysate, and HEK293 cell lysate with overexpressed ADAR2a but without oligonucleotides were used as negative controls. The SERPINA1 template ssRNA was obtained by in vitro transcription of 500 ng SERPINA1mut DNA sequence (amplified by PCR from SERPINA1mut gBlocks® gene fragments) using a MEGAscript Kit (Life Technology) applying general technologies known to the person skilled in the art and following the manufacturer's protocol, and using the T1promoterF1 forward primer (5'-GCGAAGCTTAATACGACTC-3'; SEQ ID NO:3) and the Serpina1-R2 reverse primer (5'-CCATGAAGAGGGGA-GACTTC-3'; SEQ ID NO:4). The SERPINA1mut DNA template has the following sequence (with the target adenosine in bold and underlined):

(SEQ ID NO: 5)
5'-GCGAAGCTTAATACGACTCACTATAGGGTCAACTGGGCATCACTAAG

GTCTTCAGCAATGGGGCTGACCTCTCCGGGGTCACAGAGGAGGCACCCCT

GAAGCTCTCCAAGGCCGTGCATAAGGCTGTGCTGACCATCGACAAGAAAG

GGACTGAAGCTGCTGGGGCCATGTTTTTAGAGGCCATACCCATGTCTATC

CCCCCCGAGGTCAAGTTCAACAAACCCTTTGTCTTCTTAATGATTGAACA

AAATACCAAGTCTCCCCTCTTCATGG-3'

The target ssRNA has the following sequence (with the target adenosine in bold and underlined):

(SEQ ID NO: 6)
5'-UCAACUGGGCAUCACUAAGGUCUUCAGCAAUGGGGCUGACCUCUCC

GGGGUCACAGAGGAGGCACCCCUGAAGCUCUCCAAGGCCGUGCAUAAGG

CUGUGCUGACCAUCGACAAGAAAGGGACUGAAGCUGCUGGGGCCAUGUU

UUUAGAGGCCAUACCCAUGUCUAUCCCCCCCGAGGUCAAGUUCAACAAA

CCCUUUGUCUUCUUAAUGAUUGAACAAAAUACCAAGUCUCCCCUCUUCA

UGG-3'

The target ssRNA was gel purified using denaturing polyacrylamide gel electrophoresis. To obtain the lysates, HEK293 cells were first transfected overnight with 500 ng ADARB1 expression plasmid (OriGene) using Lipofectamine 3000. Cells were then lysed using Lysis-M reagent. 200 nM AONs and 90 nM SERPINA1 template ssRNA were pre-incubated together in an in vitro editing assay buffer for 30 min at 30° C. After pre-incubation the cell lysates were added (10 µl) and the reaction mix was incubated for 30 min at 30° C. and subsequently for 30 min at 37° C. Targeted RNAs were then extracted by phenol chloroform extraction and reverse transcribed using Maxima RT Reagents, using the protocol of the manufacturer, and using the Serpina1-F2 forward primer (5'-TCAACTGGG-CATCACTAAGG-3'; SEQ ID NO:7) and the Serpina1-R2 reverse primer (see above). Then, cDNAs were amplified by PCR and analysed by Sanger sequencing using the Serpina1-R1 primer (5'-CATGAAGAGGGGAGACTTGG-3'; SEQ ID NO:8).

FIGS. 8A-8D show that when ADAR60-1 is incubated with the SERPINA1mut ssRNA target, no A-to-G change can be detected (FIG. 8A, position indicated by an arrow). In contrast however, the use of ADAR60-15 (FIG. 8B) shows a clearly detectable and significant A-to-G change, confirming editing of the target SERPINA1 RNA. The negative control reactions (FIGS. 8C and 8D) show no A-to-G editing. It is concluded that the nucleotide base chemical modifications in ADAR60-15 can enhance the RNA editing activity of ADAR2 in comparison to an oligonucleotide that has no such modifications (ADAR60-1).

Example 4. RNA Editing of a Non-Sense Mutation in GFP Target RNA Using an AON Comprising a 2-Aminopurine Modification in the Central Triplet RNA editing was also investigated in cells containing an expression construct encoding a Green Fluorescent Protein (GFP), stably integrated into the cellular genome (see WO 2016/097212 for details and constructs). In this construct, a stop codon (TAG) was introduced at codon position 57, resulting in a triplet UAG in the target RNA. Editing of the RNA at the adenosine in the middle of this triplet would eventually result in a Trp encoding codon and then in the expression of a full length protein. The construct and the cell line (cells containing a stably integrated GFP W57X plasmid) were generated using techniques known to the person of ordinary skill in the art. To ensure that no other adenosines in the target RNA are edited, only the three nucleotides in the AON opposite the stop codon (the 5'-CCA-3' in the oligonucleotide, with the mismatched C in the middle, see ADAR59-2 and ADAR59-10, FIGS. 2A-2D) do not contain a 2'-O-methyl modification, whereas all other nucleotides in the antisense oligonucleotide do. Furthermore, the terminal five nucleotides on each side of all tested oligonucleotides are connected by phosphorothioate linkages, whereas the remaining linkages were normal linkages. In ADAR59-10 the A in the Central Triplet of the oligonucleotide is chemically modified to be a 2-aminopurine, whereas ADAR59-2 does not have that particular modification. FIG. 5B in Matthews et al. (2016) shows that a 2-aminopurine modification in this position results in reduced (but not abolished) activation. However, the modification may still enhance RNA editing indirectly, for example by potentially providing enhanced nuclease resistance or enhancing cellular processes.

Stable GFP W57X containing cells were transfected first with 1 µg of ADAR2 overexpression plasmid (see the previous example), followed by transfection of 150 nM of each of the oligo's in separate batches 24 h later (both with Lipofectamine 2000). Then, 24 h after AON transfection, RNA was isolated for cDNA synthesis and subsequent RT-PCR and sequencing was performed to reveal whether RNA editing had occurred.

As shown in FIG. 9, the editing level observed with ADAR59-10 was improved over that of the control without the 2-aminopurine modification (ADAR59-2). This shows that, despite a negative effect on catalytic activity itself, an AON modification can have a positive effect on overall editing levels by indirect means. By combining such a modification with other modified nucleotides that support enhanced stability and/or editing activity (as disclosed herein), it is now possible to produce stable AONs that efficiently activate RNA editing.

Example 5. Editing of a Non-Sense Mutation in GFP Target RNA Using an AON Comprising DNA Modifications in the Central Triplet Similar to what is described in the previous example, a number of other modifications in AONs were investigated for efficient RNA editing using the GFPstop57 plasmid. For this the oligonucleotides ADAR59-2, ADAR59-10 and ADAR59-22 were compared (see FIGS. 2A-2D) with control oligonucleotide ADAR65-1 and a control situation without transfection of any oligonucleotide. In detail, 0.3×10$^6$ MCF-7 cells were seeded per well of 6-well plates in DMEM with 10% FBS. After 24 h, cells were transfected with 50 ng GFPstop57 plasmid using Lipofectamine 2000. After again 24 h, selected cell samples were transfected with 100 nM of each AON using Lipofectamine 2000. After again 24 h, RNA was isolated from lysed cells and used as a template for cDNA synthesis, which was performed using the Maxima cDNA synthesis kit using 500 ng RNA input. These samples were used for quantitative editing analysis using droplet digital PCR (ddPCR). The ddPCR assay for absolute quantification of nucleic acid target sequences was performed using Bio-Rad's QX-200 Droplet Digital PCR system. 1 µl of cDNA obtained from the RT-PCR was used in a total mixture of 20 µl of reaction mix, including the ddPCR Supermix for Probes no dUTP (Bio Rad), a Taqman SNP genotype assay (Thermo Fisher Scientific) with the relevant forward and reverse primers combined with the following gene-specific probes:

```
Forward primer:
                                          (SEQ ID NO: 9)
5'-ACCCTTAAATTTATTTGCACTA-3'

Reverse primer:
                                          (SEQ ID NO: 10)
5'-CACCATAAGAGAAAGTA-3'

Wildtype probe - FAM NFQ labeled:
                                          (SEQ ID NO: 11)
5'-CTGTTCCATGGCCAAC-3'

Mutant probe - VIC NFQ labeled:
                                          (SEQ ID NO: 12)
5'-CTGTTCCATAGCCAAC-3'
```

A total volume of 20 µl PCR mix including cDNA was filled in the middle row of a ddPCR cartridge (Bio Rad) using a multichannel pipette. The replicates were divided by two cartridges. The bottom rows were filled with 70 µl of droplet generation oil for probes (Bio Rad). After the rubber gasket replacement, droplets were generated in the QX200 droplet generator. 40 µl of oil emulsion from the top row of the cartridge was transferred to a 96-wells PCR plate. The PCR plate was sealed with a tin foil for 4 sec at 170° C. using the PX1 plate sealer, followed by the following PCR program: 1 cycle of enzyme activation for 10 min at 95° C., 40 cycles denaturation for 30 sec at 95° C. and annealing/extension for 1 min at 59.7° C., 1 cycle of enzyme deactivation for 10 min at 98° C., followed by a storage at 8° C. After PCR the plate was read and analyzed with the QX200 droplet reader. The results of the ddPCR on cDNA obtained after RNA editing using the different antisense oligonucleotides as discussed above on the GFPstop57 derived RNA are provided in Table 2. This shows that in the population of PCR products, after transfection of the plasmid alone or with the control oligonucleotide, no wt copies could be detected. But, transfections with ADAR59-2, ADAR59-10 and ADAR59-22 did result in significant amounts of wild type copies in the total population. The use of ADAR59-22 (that carries two DNA nucleotides surrounding the C opposite the target adenosine) resulted in RNA editing up to 8.3% wt copies. This indicates that use of DNA nucleotides within the Central Triplet is beneficial for efficient RNA editing using endogenous ADAR enzymes, because no additional RNA editing enzymes were used in this experiment.

TABLE 2

| Sample | Mut copies/µl | WT copies/µl | % WT in total |
|---|---|---|---|
| 50 ng GFPstp + No oligo | 40,2 | 0 | 0,0 |
| 50 ng GFPstp + ADAR65-1 | 42,1 | 0 | 0,0 |
| 50 ng GFPstp + ADAR59-2 | 60,5 | 2,8 | 4,4 |
| 50 ng GFPstp + ADAR59-10 | 121 | 6,8 | 5,3 |
| 50 ng GFPstp + ADAR59-22 | 173 | 15,7 | 8,3 |

The number of mutant (Mut) copies per µl is given as well as the number of wild type (WT) copies per µl. The percentage of WT copies in the entire population is given in the right column.

Hence, in a preferred embodiment, the invention also relates to AONs according to the invention wherein the nucleotides in the Central Triplet are DNA nucleotides, more preferably wherein the two nucleotides on each side of the C opposite the target adenosine in the Central Triplet are DNA nucleotides.

Example 6. RNA Editing with Endogenous ADAR on an Endogenous Target In Vitro

It was then investigated whether it was possible to achieve RNA editing on an endogenous target with endogenous ADAR proteins, hence without over-expression of either one. The RNA encoding the mouse Small Nuclear Ribonucleoprotein Polypeptide A (SNRPA) was chosen as an endogenous target due to its medium abundant and ubiquitous expression. SNRPA associates with stem loop II of the U1 small nuclear ribonucleoprotein, which binds the 5' splice site of precursor mRNAs and is required for splicing. The protein auto-regulates itself by polyadenylation inhibition of its own pre-mRNA via dimerization and has been implicated in the coupling of splicing and polyadenylation. AONs were designed to edit the wild type stop codon (UAG) of mouse Snrpa (pre-)mRNA which would then likely lead to extension of the messenger and resulting in a larger protein with an increase of 25 amino acids encoded by the downstream sequences. The original size of the SNRPA protein is approximately 31.68 kDa and the enlarged protein is calculated to be around 34.43 kDa. FIGS. 2A-2D show the sequence of ADAR94-1 that contains three DNA nucleotides in the Central Triplet, while all other nucleotides are 2'-O-methyl modified RNA. The five terminal nucleotides on either end are connected with phosphorothioate linkages. ADAR94-1 that contains bulges in comparison to the target sequence outside the Central Triplet (see PCT/EP2017/065467) was tested in HEPA1-6 and CMT-64 cell lines. HEPA1-6 is derived from a BW7756 mouse hepatoma that arose in a C57/L mouse. CMT-64 was isolated from a primary alveogenic lung carcinoma tumor mass in C57BL/lcrf mouse. Cells were plated in a 6-well plate 24 h prior to transfection in a density of 1.75×10$^5$ cells/well for HEPA1-6, and 1.5×10$^5$ cells/well for CMT-64. Both cell lines were cultured in regular culture medium (DMEM+10% FBS). Cells were either not transfected (NT control), transfected with an unrelated non-targeting oligo (NTO control; 200 nM of a 50-mer oligonucleotide) or transfected with final concentration of 100 nM ADAR94-1 plus a mouse specific Snrpa-related sense oligonucleotide that is thought to stabilize the AON further (SON2, see FIGS. 2A-2D) using Lipofectamine 2000 (Invitrogen) following the manufacturers protocol. Unpublished patent application GB 1700939.0 describes the use of protecting sense oligonucleotides (SONs) to stabilize antisense oligonucleotides (AONs) in RNA editing further. ADAR94-1 and SON2 were diluted to 100 µM stocks and mixed to a 1:1 ratio and incubated with the following annealing program: 60° C. 5 min, 55° C. 5 min, 50° C. 5 min, 45° C. 5 min, 40° C. 5 min, 35° C. 5 min, 30° C. 5 min, 20° C. 5 min, 10° C. until use. Prior to the transfection, medium was replaced to 1.7 mL/well fresh medium and transfection mix (300 µl) was added, making a total of 2 mL/well. 24 h after transfection 2 mL fresh medium was added to each well. Cells were incubated for another 24 h. Then, medium was removed and cells were washed once with 1×PBS and then 350 µl Trizol was added to each well for cell lysis. The lyzed cells were then collected and RNA was extracted with the Direct-Zol RNA miniprep (Zymo) following the instructions provided by the manufacturer. It was chosen not use the on-column DNAse of this kit, but instead the TURBO DNA-Free™ Kit was used for DNAse treatment of the RNA samples. For this 0.5

µl of RNAse inhibitor was added to each sample, and the rest of the steps were performed according to the manufacturer instructions. RNA concentrations were measured using the Nanodrop and 400 ng RNA was used for cDNA synthesis with the Maxima Reverse Transcriptase kit (ThermoFisher Scientific) using the protocols of the manufacturer. PCR was performed using forward primer Fw1_mSNRPA (5'-GCCTTCGTGGAGTTTGACA-3' SEQ ID NO:13) and reverse primer Rev1_mSNRPA (5'-ACACACGGCTCTGAGAAGGT-3' SEQ ID NO:14) using methods generally known to the person skilled in the art. PCR products were checked on an Agilent 2100 Bioanalyzer and purified with the Nucleo-Spin Gel and PCR clean-up kit (Macherey-Nagel). Purified products were sequenced with the sequencing primer Snrp-1-Fw1 (5'-CGTGGAGTTTGACAATGAAGT-3' SEQ ID NO:15).

Figure 10A:
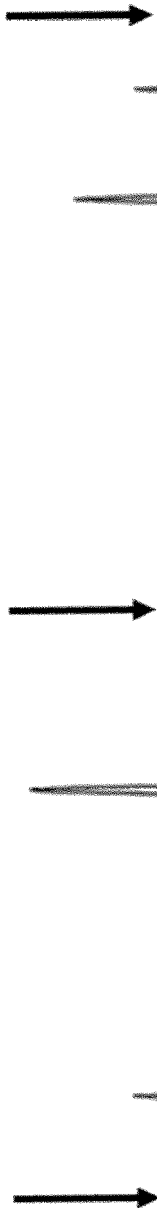
FIG. 10A and FIG. 10B show the sequencing results of a PCR product generated via cDNA from RNA isolated from mouse HEPA1-6 cells (FIG. 10A) and CMT64 cells (FIG. 10B) that were either not-transfected (NT, left panels) or transfected with a non-targeting control oligonucleotide (NTO, middle panels) or with ADAR94-1 (right panels) to edit the stop codon of the mouse Snrpa mRNA. RNA editing that is clearly above background levels is observed at the position indicated by the arrow. The sequence above all three panels in FIG. 10A
Figure 10B:
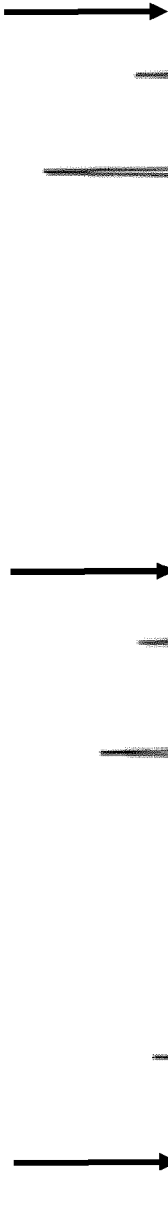
Figure 11:
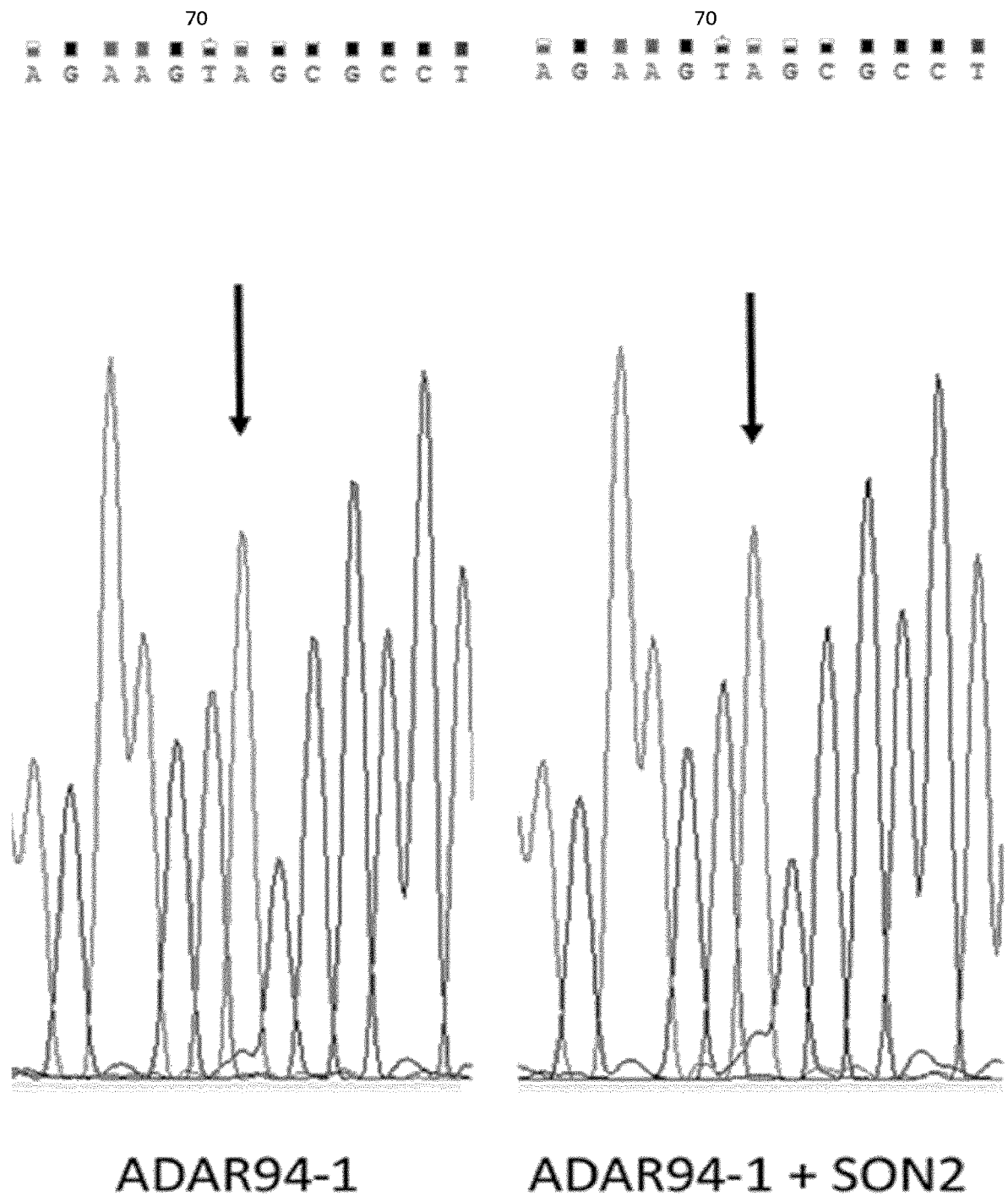
FIG. 11 shows the sequencing results of a PCR product generated via cDNA from RNA isolated from mouse HEPA1-6 cells that were transfected with ADAR94-1 alone or ADAR94-1 in combination with SON2 as described in FIG. 10A and FIG. 10B. The sequence above both panels is SEQ ID NO:38.

Sequencing results for the HEPA1-6 cells are shown in FIG. 10A and the sequencing results for the CMT64 cells are shown in FIG. 10B. Clearly, the non-transfected (NT, left panels) and non-targeting oligonucleotide (NTO, middle panels) controls show no detectable RNA editing at the stop codon (middle position of the stop codon indicated by an arrow). However, as can be clearly seen in the right panels, there is significant RNA editing detectable when the ADAR94-1 oligonucleotide was used (here in combination with the protecting SON2 oligonucleotide), both in HEPA1-6 cells as in CMT64 cells. FIG. 11 shows that this SNRPA RNA editing can also be achieved without the protecting SON, but that the addition of the SON boosted the level of RNA editing. Procedures for this +/−SON experiment were similar to that described above and performed in HEPA1-6 cells.

These results show that RNA editing can be achieved with endogenous ADAR enzymes on an endogenous target RNA sequence, in this non-limiting example using Snrpa target RNA as a model. Importantly, it shows that when the Central Triplet of the AON consists of three sequential DNA nucleotides (while the rest of the AON consists of RNA nucleotides, that are preferably 2'-O-methyl modified, very clear and significant levels of RNA editing can be achieved.

Therefore, in a preferred aspect, the present invention relates to an RNA-editing AON comprising a Central Triplet of 3 sequential nucleotides, wherein the nucleotide directly opposite the target adenosine is the middle nucleotide of the Central Triplet, wherein 1, and preferably 2, and even more preferably all 3 nucleotides in said Central Triplet are DNA nucleotides to render the AON more stable and/or more effective in inducing deamination of the target adenosine. In another preferred aspect, the remainder of the AON consists of RNA nucleotides that preferably are 2'-O-methyl modified.

Example 7. RNA Editing with Endogenous ADAR on an Endogenous Target Ex Vivo

Figure 12:
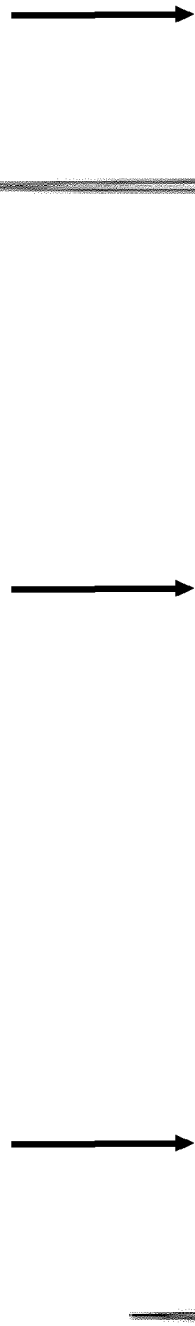
FIG. 12 shows the sequencing results of a PCR product generated via cDNA from RNA isolated from primary mouse lung cells that were either not transfected (NT, left panel), transfected with a control oligonucleotide (ADAR87-1) annealed to a protecting sense oligonucleotide SON2 (middle panel), or with an oligonucleotide targeting the mouse Snrpa RNA (ADAR94-1) annealed to SON2 (right panel). A clear increase in G signal is seen after transfection with ADAR94-1+SON2 (position indicated by an arrow), which shows that highly specific and significant RNA editing can be achieved with endogenous ADAR on an endogenous target in ex vivo primary cells. The sequence above all three panels is SEQ ID NO:37, identical to FIG. 10A and FIG. 10B.

After having found evidence of in vitro ADAR-mediated RNA editing of the Snrpa target sequence as described in the previous example, it was investigated whether it was possible to achieve RNA editing ex vivo with endogenous ADAR proteins in murine wild type primary lung cells using the same ADAR94-1 oligonucleotide (see FIGS. 2A-2D and example 6). Cells were isolated from a mouse with a C57BL/6J background using a mouse lung dissociation kit from Miltenyi Biotec (Article nr. 130-095-927). In short, all reagents were prepared under sterile conditions according to the manufacturer. Mice were sacrificed by $CO_2$ asphyxiation and perfused with PBS. Mouse lungs were then dissected from the body and transferred to a 50 ml tube containing PBS on ice. Mouse lungs were subsequently dissected into single lobes and transferred to a gentleMACS C-tube containing a kit-specific enzyme mix. Tissue was processed using the gentleMACS program 37C_m_LDK_1. After termination of the program, samples were applied to a MACS SmartStrainer (70 µm) and centrifuged at 300×g for 10 min at 4° C. Supernatant was discarded and cells were resuspended in 10 ml DMEM+10% FBS, counted and cultured in an appropriate culture flask until further processing. For transfection, cells were plated at a density of $3.0×10^5$ cells/well. The oligonucleotides were annealed to SON2, as described in example 6. Cells were either not transfected (NT), transfected with final concentration of 100 nM oligo targeting the human SNRPA sequence (ADAR87-1+SON2) or transfected with final concentration of 100 nM oligo targeting the mouse Snrpa sequence (ADAR94-1+SON2) using Turbofect (ThermoFisher Scientific) following the manufacturer's protocol. See FIGS. 2A-2D for the sequence of ADAR87-1 (see also PCT/EP2017/065467). 6 h after transfection, the medium was replaced with fresh DMEM+10% FBS and cells were cultured in total for 48 h after transfection. After these 48 h, cells were washed once with 1×PBS and 350 µl Trizol was added to each well for cell lysis. RNA was extracted with the Direct-Zol RNA miniprep (Zymo) according to the manufacturer's protocol. RNA concentrations were measured using the Nanodrop and 500 ng RNA was used for cDNA synthesis with the Maxima Reverse Transcriptase kit (ThermoFisher Scientific) according to the manufacturer's protocol. PCR was performed using forward primer Fw2_mSNRPA (5'-GCTCTCCATGCTCTTCAACC-3' SEQ ID NO:16) and reverse primer Rev2_mSNRPA (5'-TCAGGGACTGAGCCAAGG-3' SEQ ID NO:17) using methods generally known to the person skilled in the art. PCR products were checked on an Agilent 2100 Bioanalyzer and purified with the Nucleo-Spin Gel and PCR clean-up kit (Macherey-Nagel). Purified products were sequenced with sequencing primer Snrp-1-Fw1 (see above). Sequencing results are shown in FIG. 12. The targeted A in the TAG stop codon is depicted by an arrow. ADAR mediated editing will be visible in DNA sequences as a G peak under the A peak in the TAG codon. The non-transfected (NT, left) and non-targeting control oligonucleotide (ADAR87-1+SON2, middle) show no detectable RNA editing at the TAG stop codon. However, when cells are transfected with ADAR94-1+SON2 (right panel) a clear detectable editing is observed in the TAG stop codon.

It is concluded that RNA editing can be achieved with endogenous ADAR using endogenous Snrpa target RNA as a model. Moreover, as the cells used in this example were directly isolated from mice, it indicates that site-specific RNA editing with endogenous ADAR on an endogenous target using a (therapeutic) oligonucleotide is feasible in vivo. In addition to this, and as already shown in example 6, it indicates that when the Central Triplet of the targeting AON consists of three sequential DNA nucleotides (while the rest of the AON consists of RNA nucleotides that are preferably 2'-O-methyl modified) very clear and significant levels of RNA editing can be achieved with endogenous levels of ADAR.

Example 8. RNA Editing in Murine WT Primary Lung Cells on Snrpa (Pre)mRNA Measured by ddPCR Additionally, chemical modifications of nucleosides in positions outside the so-called Central Triplet were investigated for further improvement of RNA editing ability. Such was also tested in the Snrpa model as described in the previous examples using ADAR89-10, -15, and -20. The ribose of the nucleoside at position −1 was 2'-O-methyl modified, and the nucleosides at positions +2 and +3 it were modified as follows: 2'-O-methyl in ADAR89-10, deoxyribose (DNA) in ADAR89-15, and 2'-NH$_2$ in ADAR89-20 (FIGS. 2A-2D). The editing ability of these AONs were tested in primary lung cells assay as described in the previous example, and analyzed by a ddPCR technique as follows. Absolute quantification of nucleic acid target sequences was performed using BioRad's QX-200 Droplet Digital PCR system. 1 µl of cDNA obtained from the RT-PCR (1/10 diluted) was used in a total mixture of 20 µl of reaction mix, including the ddPCR Supermix for Probes no dUTP (BioRad), a Taqman SNP genotype assay with the relevant forward and reverse primers combined with the following gene-specific probes:

```
Forward primer
                                       (SEQ ID NO: 18)
5'-GCAAGGCTTTAAGATCACACAAA-3'

Reverse primer
                                       (SEQ ID NO: 19)
5'-GGAAGGGACTGGGGTACTC-3' wt probe (HEX IBFQ label)
                                       (SEQ ID NO: 20)
5'-TTTGCCAAGAAGTAGCGCCTTTCCCT-3' mutant probe (FAM IBFQ label)
                                       (SEQ ID NO: 21)
5'-TTTGCCAAGAAGTGGCGCCTTTCCCT-3'
```

Figure 13:
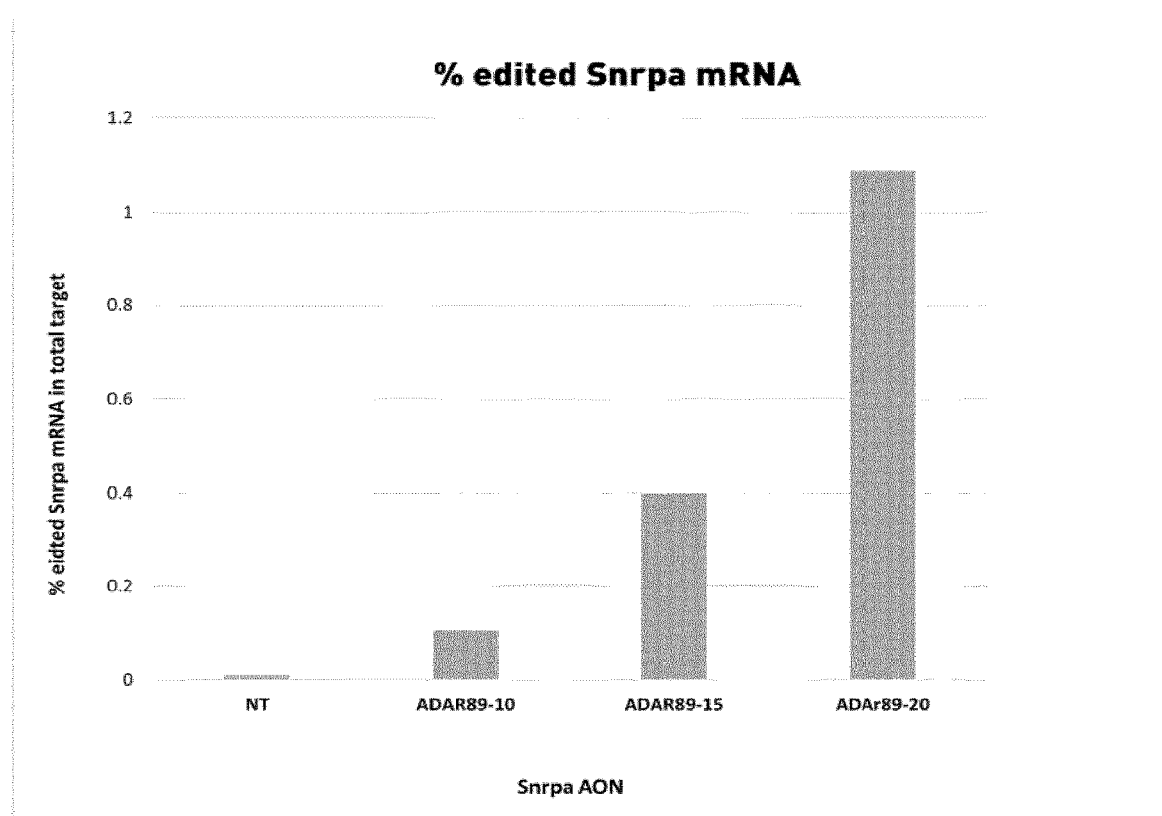
FIG. 13 shows the editing ability of AONs as a percentage of edited mRNA in total target RNA measured by ddPCR. NT: Non-treated.

A total volume of 20 µl PCR mix including cDNA was filled in the middle row of a ddPCR cartridge (Bio Rad) using a multichannel pipette. The replicates were divided by two cartridges. The bottom rows were filled with 70 µl of droplet generation oil for probes (Bio Rad). After the rubber gasket replacement droplets were generated in the QX200 droplet generator. 40 µl of oil emulsion from the top row of the cartridge was transferred to a 96-wells PCR plate. The PCR plate was sealed with a tin foil for 4 sec at 170° C. using the PX1 plate sealer and directly followed by the following PCR program: 1 cycle of enzyme activation for 10 min at 95° C., 40 cycles denaturation for 30 sec at 95° C. and annealing/extension for 1 min at 63.8° C., 1 cycle of enzyme deactivation for 10 min at 98° C., followed by a storage at 8° C. After the PCR program the plate was read out and analyzed with the QX200 droplet reader with the following settings: Absolute quantification, Supermix for probes no dUTP, Ch1 FAM Wildtype and CH2 HEX mutant. The results as provided in FIG. 13 show that significant editing of the target RNA was achieved by all AONs, with ADAR89-20 performing best.

Example 9. Chemical Modifications in AONs Targeting Mouse IDUA RNA for RNA Editing Then, the inventors asked themselves whether the modifications that yielded stabilization could be further combined and whether the AONs with such combinations would be functional in RNA editing in the Hurler model (see also example 2). The effect of these AONs on restoring the wild type sequence was tested in an assay that measures the activity of the α-L-iduronidase enzyme encoded by the mouse ldua gene. For this, immortalized mouse embryonic fibroblast cells (70,000 per sample) derived from a W392X mutant mouse were cultured in growth medium (DMEM/10% FCS), and transfected with 1 µg of an expression plasmid carrying the full length ldua W392X cDNA using Lipofectamine 3000. After 24 h, the cells were similarly transfected with 100 nM (final concentration) of each of the respective AONs of the ADAR65 series (see FIGS. 5 and 6 for stability results), and cultured for an additional 48 h. Cells were then collected and lysed in mPER buffer (Thermo Scientific #78501). The cell fragments were removed from the lysates by centrifugation and 25 µl of the supernatant was used for the enzymatic 5 assay: 25 µl of 360 µM 4-Methylumbelliferyl α-L-iduronide in 0.4 M sodium formate buffer (pH 3.5) was added in the lysate samples, which were then incubated for 2 h at 37° C. Reaction was terminated by addition of 200 µl of 0.17 M glycine buffer (pH 9.9), and the resulting fluorescent intensity was then measured (excitation wavelength 365 nm and emission 450 nm). Results were normalized to total protein concentration of the samples, as 10 measured by BCA assay (Pierce™ BCA Protein Assay Kit, Thermo Scientific).

Figure 14:
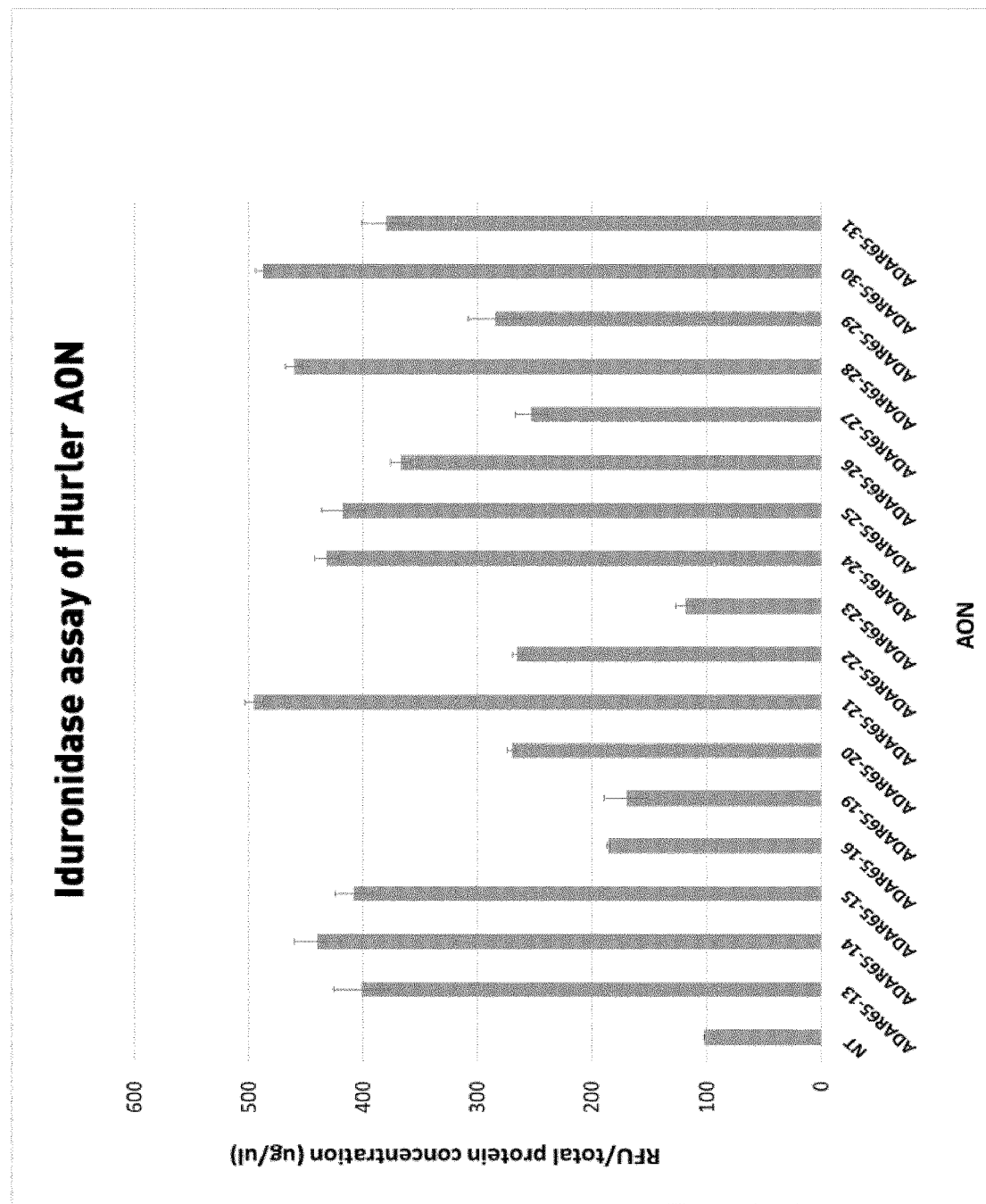
FIG. 14 shows the enzymatic activity (as relative fluorescence units normalized to total protein concentration) measured in an α-L-iduronidase assay which is an indication of the presence of a wt Idua mRNA that is a result of RNA editing upon transfection with RNA-editing AONs. Mouse embryonic fibroblasts carrying the mutated Idua gene were transfected with an expression plasmid also expressing the mouse mutated Idua gene, and subsequently transfected with the AONs as depicted. Average activity and standard deviation from two duplicate measurements is shown for each AON. NT: Non-transfected with AON.

The results provided in FIG. 14 show that all of transfected ADAR65 oligonucleotides were able to increase α-L-iduronidase enzyme activity above non-transfected (NT) levels, indicating that the target (pre-)mRNA was edited. It appears that most of the applied AONs in fact edit the target RNA quite efficiently. As can be seen in a comparison with the stability assay (FIGS. 5 and 6) many of the AONs (especially ADAR65-23 to ADAR65-30) show high stability and also show good ability to restore enzymatic activity of the α-L-iduronidase enzyme, showing that the use of DNA nucleotides, and 2'-fluoro modifications as well as phosphorothioate linkages within the Central Triplet are useful and therefore preferred embodiments of the present invention.

The invention claimed is:

1. An antisense oligonucleotide (AON) comprising a Central Triplet of 3 sequential nucleotides, wherein
   (i) the AON is capable of forming a double stranded complex with a target RNA molecule in a cell comprising a target adenosine;
   (ii) the nucleotide directly opposite the target adenosine is the middle nucleotide of the Central Triplet;
   (iii) 1, 2 or 3 nucleotides in the Central Triplet comprise a sugar modification and/or a base modification to render the AON more stable and/or more effective in inducing deamination of the target adenosine; with the proviso that the middle nucleotide does not have a 2'-O-methyl modification;
   (iv) the AON does not comprise a 5'-terminal O6-benzylguanosine;
   (v) the AON does not comprise a portion that is capable of forming an intramolecular stem-loop structure that is capable of binding a mammalian ADAR enzyme present in the cell; and,
   (vi) the AON can mediate the deamination of the target adenosine by the ADAR enzyme.

2. The AON of claim 1, wherein 2 or 3 nucleotides in the Central Triplet do not have a 2'-O-methyl modification.

3. The AON of claim 1, wherein 2 or 3 nucleotides in the Central Triplet do not have a 2'-O-alkyl modification.

4. The AON of claim 1, wherein 1 or 2 nucleotides in the Central Triplet other than the middle nucleotide are inosine.

5. The AON of claim 4, wherein the 3' nucleotide of the Central Triplet is inosine.

6. The AON of claim 4, wherein 1 nucleotide in the Central Triplet other than the middle nucleotide is inosine.

7. The AON of claim 1, wherein the sugar modification is selected from the group consisting of deoxyribose (DNA), Unlocked Nucleic Acid (UNA) and 2'-fluororibose.

8. The AON of claim 1, wherein the AON comprises at least one internucleoside linkage modification selected from the group consisting of phosphorothioate, 3'-methylenephosphonate, 5'-methylenephosphonate, 3'-phosphoroamidate and 2'-5'-phosphodiester.

9. The AON of claim 8, wherein the 2, 3, 4, 5, or 6 terminal nucleotides of the 5' and 3' terminus of the AON are linked with phosphorothioate linkages.

10. The AON of claim 1, wherein the base modification is selected from the group consisting of 2-aminopurine, 2,6-diaminopurine, 3-deazaadenosine, 7-deazaadenosine, 7-methyladenosine, 8-azidoadenosine, 8-methyladenosine, 5-hydroxymethylcytosine, 5-methylcytidine, pyrrolocytidine, 7-aminomethyl-7-deazaguanosine, 7-deazaguanosine, 7-methylguanosine, 8-aza-7-deazaguanosine, thienoguanosine, inosine, 4-thio-uridine, 5-methoxyuridine, dihydrouridine, and pseudouridine.

11. The AON of claim 1, wherein the middle nucleotide in the Central Triplet is a cytidine or a uridine.

12. The AON of claim 1, wherein one or more nucleotides in the AON outside the Central Triplet comprise a modification selected from the group consisting of DNA, a 2'-O-alkyl group, a 2'-O-methoxyethyl group, a 2'-F group, a 2'-NH$_2$ group, an LNA, and any combinations thereof.

13. The AON of claim 12, wherein the 2'-O-alkyl group is a 2'-O-methyl group.

14. The AON of claim 1, wherein the AON is longer than 10, 11, 12, 13, 14, 15, 16 or 17 nucleotides, and wherein the AON is shorter than 100 nucleotides.

15. The AON of claim 14, wherein the AON comprises 18 to 70 nucleotides.

16. The AON of claim 15, wherein the AON comprises 18 to 60 nucleotides.

17. The AON of claim 16, wherein the AON comprises 18 to 50 nucleotides.

18. The AON of claim 14, wherein the AON is shorter than 60 nucleotides.

19. The AON of claim 18, wherein the AON comprises 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides.

20. The AON of claim 14, wherein the AON is 30 nucleotides long.

21. The AON of claim 1, wherein the target RNA molecule encodes alpha-1-antitrypsin (A1AT) or LRRK2, or wherein the target RNA molecule is encoded by the IDUA gene.

22. The AON of claim 21, wherein the target RNA molecule encodes A1AT to edit a 9989G>A mutation or a 1096G>A mutation, the target RNA molecule encodes LRRK2 to edit a G6055A mutation, or the target RNA molecule is encoded by the IDUA gene to edit a c.1205G>A (W402X) mutation.

23. The AON of claim 1, wherein the cell is a human cell.

24. The AON of claim 1, wherein the 5 terminal nucleotides of the 5' and 3' terminus of the AON are linked with phosphorothioate linkages.

25. The AON of claim 1, wherein at least one nucleotide in the Central Triplet is a modified uridine.

26. The AON of claim 25, wherein the modified uridine is a pseudouridine.

27. The AON of claim 26, wherein the pseudouridine is present at the central position of the Central Triplet.

28. The AON of claim 1, wherein the AON comprises at least one phosphoramidate internucleoside linkage modification.

29. A pharmaceutical composition comprising the AON of claim 1, and a pharmaceutically acceptable carrier.

30. A method of treating a genetic disorder in a human subject in need thereof, the method comprising administering the AON of claim 1 to the subject, wherein the genetic disorder is alpha-1-antitrypsin (A1AT) deficiency, Hurler Syndrome, or Parkinson's disease.

31. The method of claim 30, wherein the AON administration is in vivo or ex vivo.

32. The method of claim 30, wherein the AON is formulated for intravenous administration.

33. A method for the deamination of at least one specific target adenosine present in a target RNA molecule in a cell, the method comprising the steps of:
   (i) providing the cell with the AON of claim 1;
   (ii) allowing uptake by the cell of the AON;
   (iii) allowing annealing of the AON to the target RNA molecule; and,
   (iv) allowing a mammalian ADAR enzyme comprising a natural dsRNA binding domain as found in the wild type enzyme to deaminate the target adenosine in the target RNA molecule to an inosine.

34. The method of claim 33, wherein the method further comprises:
   a) sequencing the target RNA molecule;
   b) assessing the presence of a functional, elongated, full length and/or wild type protein when the target adenosine is located in a UGA or UAG stop codon, which is edited to a UGG codon through the deamination;
   c) assessing the presence of a functional, elongated, full length and/or wild type protein when two target adenosines are located in a UAA stop codon, which is edited to a UGG codon through the deamination of both target adenosines;
   d) assessing whether splicing of the pre-mRNA was altered by the deamination; or
   e) using a functional read-out, wherein the target RNA molecule after the deamination encodes a functional, full length, elongated and/or wild type protein.

35. The method of claim 33, wherein the cell is a skin cell, a lung cell, a heart cell, a kidney cell, a liver cell, a pancreas cell, a gut cell, a muscle cell, a gland cell, an eye cell, a brain cell, or a blood cell.

36. The method of claim 33, wherein the cell is a stem cell.

37. The method of claim 36, wherein the stem cell is an embryonic stem cell, a pluripotent stem cell, a totipotent stem cell, or an induced pluripotent stem cell.

38. The method of claim 33, wherein the target RNA molecule is selected from a messenger RNA (mRNA), a pre-mRNA, a ribosomal RNA (rRNA), a mitochondrial RNA (mtRNA), a transfer RNA (tRNA), noncoding RNA (ncRNA), or a microRNA (miRNA).

39. An AON comprising a Central Triplet of 3 sequential nucleotides, wherein
   (i) the AON is capable of forming a double stranded complex with an A1AT target RNA molecule in a human cell comprising a target adenosine;
   (ii) the nucleotide directly opposite the target adenosine is the middle nucleotide of the Central Triplet;
   (iii) all three nucleotides in the Central Triplet comprise a 2'-deoxyribose modification;
   (iv) one nucleotide in the Central Triplet other than the middle nucleotide is deoxyinosine;
   (v) the AON comprises at least one phosphorothioate internucleoside linkage
   (vi) the AON does not comprise a 5'-terminal O6-benzylguanosine;
   (vii) the AON does not comprise a portion that is capable of forming an intramolecular stem-loop structure that is capable of binding a human ADAR enzyme present in the human cell; and,
   (viii) the AON can mediate the deamination of the target adenosine in the A1AT target RNA molecule by the human ADAR enzyme.

40. A method of treating A1AT deficiency in a human subject in need thereof comprising administering the AON of claim 39 or a pharmaceutical composition comprising said AON to the subject.

* * * * *

SEQUENCE LISTING

<160> NUMBER OF SEQ ID NOS: 38

<210> SEQ ID NO 1
<211> LENGTH: 62
<212> TYPE: RNA
<213> ORGANISM: Homo sapiens

<400> SEQUENCE: 1
auaaggcugu gcugaccauc gacaagaaag ggacugaagc ugcuggggcc auguuuuag      60 ag                                                                    62

<210> SEQ ID NO 2
<211> LENGTH: 54
<212> TYPE: RNA
<213> ORGANISM: Homo sapiens

<400> SEQUENCE: 2
gccccgcaga ugaggagcag cucuaggccg aaguguCgca ggccgggacc gucc        54

<210> SEQ ID NO 3
<211> LENGTH: 19
<212> TYPE: DNA
<213> ORGANISM: Artificial Sequence
<220> FEATURE:
<223> OTHER INFORMATION: T1promoterF1 forward primer

<400> SEQUENCE: 3
gcgaagctta atacgactc                                                19

<210> SEQ ID NO 4
<211> LENGTH: 20
<212> TYPE: DNA
<213> ORGANISM: Artificial sequence
<220> FEATURE:
<223> OTHER INFORMATION: Serpina1-R2 reverse primer

<400> SEQUENCE: 4
ccatgaagag gggagacttc                                               20

<210> SEQ ID NO 5
<211> LENGTH: 273
<212> TYPE: DNA
<213> ORGANISM: Homo sapiens

<400> SEQUENCE: 5
gcgaagctta atacgactca ctatagggtc aactgggcat cactaaggtc ttcagcaatg   60
gggctgacct ctccggggtc acagaggagg caccCctgaa gctctccaag gccgtgcata  120
aggctgtgct gaccatcgac aagaaaggga ctgaagctgc tggggccatg ttttttagagg  180 ccatacccat gtctatcccc cccgaggtca agttcaacaa acccttgtgt ttcttaatga   240
ttgaacaaaa taccaagtct cccctcttca tgg                                273

<210> SEQ ID NO 6
<211> LENGTH: 245
<212> TYPE: RNA
<213> ORGANISM: Homo sapiens

<400> SEQUENCE: 6
ucaacugggc aucacuaagg ucuucagcaa uggggcugac cucuccgggg ucacagagga   60
ggcaccccug aagcucucca aggccgugca uaaggcugug cugaccaucg acaagaaagg  120
gacugaagcu gcuggggcca uguuuuuaga ggccauaccc augucuaucc ccccgaggu   180 caaguucaac aaacccuuug ucuucuuaau gauugaacaa aauaccaagu cuccccucuu   240
caugg                                                               245

<210> SEQ ID NO 7
<211> LENGTH: 20
<212> TYPE: DNA
<213> ORGANISM: Artificial sequences
<220> FEATURE:
<223> OTHER INFORMATION: Serpina1-F2 forward primer

<400> SEQUENCE: 7

```
tcaactgggc atcactaagg                                               20

<210> SEQ ID NO 8
<211> LENGTH: 20
<212> TYPE: DNA
<213> ORGANISM: Artificial sequence
<220> FEATURE:
<223> OTHER INFORMATION: Serpina1-R1 primer

<400> SEQUENCE: 8
catgaagagg ggagacttgg                                               20

<210> SEQ ID NO 9
<211> LENGTH: 22
<212> TYPE: DNA
<213> ORGANISM: Artificial sequence
<220> FEATURE:
<223> OTHER INFORMATION: Forward primer

<400> SEQUENCE: 9
acccttaaat ttatttgcac ta                                            22

<210> SEQ ID NO 10
<211> LENGTH: 17
<212> TYPE: DNA
<213> ORGANISM: Artificial sequence
<220> FEATURE:
<223> OTHER INFORMATION: Reverse primer

<400> SEQUENCE: 10
caccataaga gaaagta                                                  17

<210> SEQ ID NO 11
<211> LENGTH: 16
<212> TYPE: DNA
<213> ORGANISM: Artificial sequence
<220> FEATURE:
<223> OTHER INFORMATION: Wildtype probe

<400> SEQUENCE: 11
ctgttccatg gccaac                                                   16

<210> SEQ ID NO 12
<211> LENGTH: 16
<212> TYPE: DNA
<213> ORGANISM: Artificial sequence
<220> FEATURE:
<223> OTHER INFORMATION: Mutant probe

<400> SEQUENCE: 12
ctgttccata gccaac                                                   16

<210> SEQ ID NO 13
<211> LENGTH: 19
<212> TYPE: DNA
<213> ORGANISM: Artificial sequence
<220> FEATURE:
<223> OTHER INFORMATION: Fw1_mSNRPA

<400> SEQUENCE: 13
gccttcgtgg agtttgaca                                                19

<210> SEQ ID NO 14
<211> LENGTH: 20
<212> TYPE: DNA
<213> ORGANISM: Artificial sequence
```

```
<220> FEATURE:
<223> OTHER INFORMATION: Rev1_mSNRPA

<400> SEQUENCE: 14
acacacggct ctgagaaggt                                               20

<210> SEQ ID NO 15
<211> LENGTH: 21
<212> TYPE: DNA
<213> ORGANISM: Artificial sequence
<220> FEATURE:
<223> OTHER INFORMATION: Snrp-1-Fw1

<400> SEQUENCE: 15
cgtggagttt gacaatgaag t                                             21

<210> SEQ ID NO 16
<211> LENGTH: 20
<212> TYPE: DNA
<213> ORGANISM: Artificial sequence
<220> FEATURE:
<223> OTHER INFORMATION: Fw2_mSNRPA

<400> SEQUENCE: 16
gctctccatg ctcttcaacc                                               20

<210> SEQ ID NO 17
<211> LENGTH: 18
<212> TYPE: DNA
<213> ORGANISM: Artificial sequence
<220> FEATURE:
<223> OTHER INFORMATION: Rev2_mSNRPA

<400> SEQUENCE: 17
tcagggactg agccaagg                                                 18

<210> SEQ ID NO 18
<211> LENGTH: 23
<212> TYPE: DNA
<213> ORGANISM: Artificial sequence
<220> FEATURE:
<223> OTHER INFORMATION: Forward primer

<400> SEQUENCE: 18
gcaaggcttt aagatcacac aaa                                           23

<210> SEQ ID NO 19
<211> LENGTH: 19
<212> TYPE: DNA
<213> ORGANISM: Artificial sequence
<220> FEATURE:
<223> OTHER INFORMATION: Reverse primer

<400> SEQUENCE: 19
ggaagggact ggggtactc                                                19

<210> SEQ ID NO 20
<211> LENGTH: 26
<212> TYPE: DNA
<213> ORGANISM: Artificial sequence
<220> FEATURE:
<223> OTHER INFORMATION: wt probe

<400> SEQUENCE: 20
tttgccaaga agtagcgcct ttccct                                        26
```

<210> SEQ ID NO 21
<211> LENGTH: 26
<212> TYPE: DNA
<213> ORGANISM: Artificial sequence
<220> FEATURE:
<223> OTHER INFORMATION: mutant probe

<400> SEQUENCE: 21
tttgccaaga agtggcgcct ttccct                                              26

<210> SEQ ID NO 22
<211> LENGTH: 31
<212> TYPE: DNA
<213> ORGANISM: Artificial sequence
<220> FEATURE:
<223> OTHER INFORMATION: ADAR60-1
<220> FEATURE:
<221> NAME/KEY: modified_base
<222> LOCATION: (13)..(13)
<223> OTHER INFORMATION: p
<220> FEATURE:
<221> NAME/KEY: modified_base
<222> LOCATION: (13)..(13)
<223> OTHER INFORMATION: s4u
<220> FEATURE:
<221> NAME/KEY: modified_base
<222> LOCATION: (13)..(13)
<223> OTHER INFORMATION: t
<220> FEATURE:
<221> NAME/KEY: misc_feature
<222> LOCATION: (13)..(13)
<223> OTHER INFORMATION: thienouridine
<220> FEATURE:
<221> NAME/KEY: misc_feature
<222> LOCATION: (13)..(13)
<223> OTHER INFORMATION: 2,6-diaminopurine
<220> FEATURE:
<221> NAME/KEY: modified_base
<222> LOCATION: (13)..(13)
<223> OTHER INFORMATION: mo5u
<220> FEATURE:
<221> NAME/KEY: modified_base
<222> LOCATION: (13)..(13)
<223> OTHER INFORMATION: d
<220> FEATURE:
<221> NAME/KEY: misc_feature
<222> LOCATION: (14)..(14)
<223> OTHER INFORMATION: 5-methylcytidine
<220> FEATURE:
<221> NAME/KEY: misc_feature
<222> LOCATION: (14)..(14)
<223> OTHER INFORMATION: pyrrolocytidine
<220> FEATURE:
<221> NAME/KEY: misc_feature
<222> LOCATION: (14)..(14)
<223> OTHER INFORMATION: hydroxymethylcytidine
<220> FEATURE:
<221> NAME/KEY: modified_base
<222> LOCATION: (15)..(15)
<223> OTHER INFORMATION: I
<220> FEATURE:
<221> NAME/KEY: misc_feature
<222> LOCATION: (15)..(15)
<223> OTHER INFORMATION: thienoguanosine
<220> FEATURE:
<221> NAME/KEY: misc_feature
<222> LOCATION: (15)..(15)
<223> OTHER INFORMATION: 7-methylguanosine
<220> FEATURE:
<221> NAME/KEY: misc_feature
<222> LOCATION: (15)..(15)
<223> OTHER INFORMATION: 7-deazaguanosine
<220> FEATURE:
<221> NAME/KEY: misc_feature
<222> LOCATION: (15)..(15)
<223> OTHER INFORMATION: 8-aza-7-deazaguanosine

```
<220> FEATURE:
<221> NAME/KEY: misc_feature
<222> LOCATION: (15)..(15)
<223> OTHER INFORMATION: 7-aminomethyl-7-deazaguanosine

<400> SEQUENCE: 22
ucagucccuu ucucgucgau ggucagcaca g                              31

<210> SEQ ID NO 23
<211> LENGTH: 33
<212> TYPE: DNA
<213> ORGANISM: Artificial sequence
<220> FEATURE:
<223> OTHER INFORMATION: ADAR68
<220> FEATURE:
<221> NAME/KEY: misc_feature
<222> LOCATION: (17)..(17)
<223> OTHER INFORMATION: 5-methylcytidine
<220> FEATURE:
<221> NAME/KEY: misc_feature
<222> LOCATION: (18)..(18)
<223> OTHER INFORMATION: 5-methylcytidine
<220> FEATURE:
<221> NAME/KEY: misc_feature
<222> LOCATION: (19)..(19)
<223> OTHER INFORMATION: 7-methyladenosine
<220> FEATURE:
<221> NAME/KEY: misc_feature
<222> LOCATION: (19)..(19)
<223> OTHER INFORMATION: 8-methyladenosine
<220> FEATURE:
<221> NAME/KEY: misc_feature
<222> LOCATION: (19)..(19)
<223> OTHER INFORMATION: 3-deazaadenosine
<220> FEATURE:
<221> NAME/KEY: misc_feature
<222> LOCATION: (19)..(19)
<223> OTHER INFORMATION: 7-deazaadenosine
<220> FEATURE:
<221> NAME/KEY: misc_feature
<222> LOCATION: (19)..(19)
<223> OTHER INFORMATION: 8-azidoadenosine
<220> FEATURE:
<221> NAME/KEY: modified_base
<222> LOCATION: (19)..(19)
<223> OTHER INFORMATION: I

<400> SEQUENCE: 23
ccugcgacac uucggcccag agcugcuccu cau                            33

<210> SEQ ID NO 24
<211> LENGTH: 53
<212> TYPE: DNA
<213> ORGANISM: Artificial sequence
<220> FEATURE:
<223> OTHER INFORMATION: ADAR59
<220> FEATURE:
<221> NAME/KEY: misc_feature
<222> LOCATION: (41)..(41)
<223> OTHER INFORMATION: 2-aminopurine

<400> SEQUENCE: 24
cauugaagaa gauaagagaa aguacugaga aguguuggcc auggaacagg uag       53

<210> SEQ ID NO 25
<211> LENGTH: 45
<212> TYPE: DNA
<213> ORGANISM: Artificial sequence
<220> FEATURE:
<223> OTHER INFORMATION: ADAR94-1

<400> SEQUENCE: 25
```

```
gacugaggua cuccuuagag aaaggugcca cuucuuggca aagga            45

<210> SEQ ID NO 26
<211> LENGTH: 15
<212> TYPE: RNA
<213> ORGANISM: Artificial sequence
<220> FEATURE:
<223> OTHER INFORMATION: SON2

<400> SEQUENCE: 26
aagaaguggc accuu                                            15

<210> SEQ ID NO 27
<211> LENGTH: 40
<212> TYPE: RNA
<213> ORGANISM: Artificial sequence
<220> FEATURE:
<223> OTHER INFORMATION: ADAR87-1

<400> SEQUENCE: 27
guaggcaugg gaggaaaagg ugccacuucu uggcaaagga                 40

<210> SEQ ID NO 28
<211> LENGTH: 50
<212> TYPE: DNA
<213> ORGANISM: Artificial sequence
<220> FEATURE:
<223> OTHER INFORMATION: ADAR65
<220> FEATURE:
<221> NAME/KEY: misc_feature
<222> LOCATION: (36)..(36)
<223> OTHER INFORMATION: 5-methylcytidine
<220> FEATURE:
<221> NAME/KEY: misc_feature
<222> LOCATION: (38)..(38)
<223> OTHER INFORMATION: deoxy 2-aminopurine

<400> SEQUENCE: 28 cguccaaca cagccccagc cuuugagacc ucugcccaga guuguucuc        50

<210> SEQ ID NO 29
<211> LENGTH: 50
<212> TYPE: DNA
<213> ORGANISM: Artificial sequence
<220> FEATURE:
<223> OTHER INFORMATION: ADAR65-18

<400> SEQUENCE: 29 cguccaaca cagccccagc cuuugagacc ucuguccaga auuguucuc        50

<210> SEQ ID NO 30
<211> LENGTH: 43
<212> TYPE: DNA
<213> ORGANISM: Artificial sequence
<220> FEATURE:
<223> OTHER INFORMATION: ADAR93-2

<400> SEQUENCE: 30
acacagcucc agccuuugag accucugccc agaguuguuc ucc             43

<210> SEQ ID NO 31
<211> LENGTH: 42
<212> TYPE: DNA
<213> ORGANISM: Artificial sequence
<220> FEATURE:
<223> OTHER INFORMATION: ADAR93-6

<400> SEQUENCE: 31
```
cacagcccca gccuuugaga ccucugucca gaguuguucu cc    42

<210> SEQ ID NO 32
<211> LENGTH: 42
<212> TYPE: DNA
<213> ORGANISM: Artificial sequence
<220> FEATURE:
<223> OTHER INFORMATION: ADAR93-8

<400> SEQUENCE: 32
cacagcccca gccuuugaga ccucugucca gaguuguucu cc    42

<210> SEQ ID NO 33
<211> LENGTH: 42
<212> TYPE: DNA
<213> ORGANISM: Artificial sequence
<220> FEATURE:
<223> OTHER INFORMATION: ADAR93-9

<400> SEQUENCE: 33
cacagcccca gccuuugaga ccucugccca gaauuguucu cc    42

<210> SEQ ID NO 34
<211> LENGTH: 45
<212> TYPE: DNA
<213> ORGANISM: Artificial sequence
<220> FEATURE:
<223> OTHER INFORMATION: ADAR89

<400> SEQUENCE: 34
gacugaggua cuccauaggg aaaggcacca cuucuuggca aagga    45

<210> SEQ ID NO 35
<211> LENGTH: 22
<212> TYPE: DNA
<213> ORGANISM: Homo sapiens

<400> SEQUENCE: 35
accatcgaca agaaagggac tg    22

<210> SEQ ID NO 36
<211> LENGTH: 17
<212> TYPE: DNA
<213> ORGANISM: Artificial sequence
<220> FEATURE:
<223> OTHER INFORMATION: Mutant GFP

<400> SEQUENCE: 36
tgttccatag ccaacac    17

<210> SEQ ID NO 37
<211> LENGTH: 29
<212> TYPE: DNA
<213> ORGANISM: Mus musculus

<400> SEQUENCE: 37
ttttgccaag aagtagcgcc tttccctat    29

```
<210> SEQ ID NO 38
<211> LENGTH: 13
<212> TYPE: DNA
<213> ORGANISM: Mus musculus

<400> SEQUENCE: 38
agaagtagcg cct                                                          13
```